United States Patent
Knox et al.

(10) Patent No.: US 9,007,223 B2
(45) Date of Patent: *Apr. 14, 2015

(54) PARTICLE DETECTOR, SYSTEM AND METHOD

(71) Applicant: Xtralis Technologies Ltd, Nassau, NP (BS)

(72) Inventors: Ron Knox, Mount Eliza (AU); Karl Boettger, Glen Waverley (AU); Kemal Ajay, Mount Waverley (AU)

(73) Assignee: Xtralis Technologies Ltd., Nassau (BS)

( * ) Notice: Subject to any disclaimer, the term of this patent is extended or adjusted under 35 U.S.C. 154(b) by 0 days.

This patent is subject to a terminal disclaimer.

(21) Appl. No.: 13/936,418

(22) Filed: Jul. 8, 2013

(65) Prior Publication Data

US 2014/0022547 A1    Jan. 23, 2014

Related U.S. Application Data

(63) Continuation of application No. 11/719,226, filed as application No. PCT/AU2005/001723 on Nov. 14, 2005, now Pat. No. 8,508,376.

(60) Provisional application No. 60/626,960, filed on Nov. 12, 2004.

(30) Foreign Application Priority Data

Nov. 12, 2004    (AU) ................................ 2004906488

(51) Int. Cl.
*G08B 17/10* (2006.01)
*G01N 21/49* (2006.01)
(Continued)

(52) U.S. Cl.
CPC .............. *G01N 21/49* (2013.01); *G01S 17/026* (2013.01); *G01S 17/87* (2013.01); *G08B 17/107* (2013.01); *G08B 17/125* (2013.01); *G08B 29/24* (2013.01); *G08B 25/10* (2013.01); *G08B 17/103* (2013.01); *G01S 7/4873* (2013.01); *G01S 7/4876* (2013.01);
(Continued)

(58) Field of Classification Search
USPC ............... 340/628, 629, 630, 693.6; 382/218, 382/128, 103; 386/227; 356/5.04, 5.03, 356/438; 235/454
See application file for complete search history.

(56) References Cited

U.S. PATENT DOCUMENTS 3,429,243 A    2/1969    Boyle
3,688,298 A    8/1972    Miller et al.
(Continued)

FOREIGN PATENT DOCUMENTS

DE    3641716 A1    6/1988
JP    S5387283 A    8/1978
(Continued)

OTHER PUBLICATIONS

European Search Report issued in European Patent Application No. 12183106.9 dated May 15, 2013.
(Continued)

*Primary Examiner* — Hoi Lau
(74) *Attorney, Agent, or Firm* — Sughrue Mion, PLLC

(57) ABSTRACT

The invention provides use of one or more emitted beams of radiation (16), for example, laser beam(s), in combination with an image capturing means (14), for example, one or more video cameras and/or optical elements to detect particles (30), for example, smoke particles, located in an open space (12).

19 Claims, 42 Drawing Sheets

(51) Int. Cl.
| | |
|---|---|
| *G01S 17/02* | (2006.01) |
| *G01S 17/87* | (2006.01) |
| *G08B 17/107* | (2006.01) |
| *G08B 17/12* | (2006.01) |
| *G08B 29/24* | (2006.01) |
| *G08B 25/10* | (2006.01) |
| *G08B 17/103* | (2006.01) |
| *G01S 7/487* | (2006.01) |
| *G08B 29/04* | (2006.01) |
| *G01N 21/53* | (2006.01) |
| *G01S 17/95* | (2006.01) |

(52) U.S. Cl.
CPC ............ *G08B 29/043* (2013.01); *G01N 21/532* (2013.01); *G01S 17/95* (2013.01)

(56) References Cited

U.S. PATENT DOCUMENTS

| | | |
|---|---|---|
| 3,727,056 A | 4/1973 | Enemark |
| 3,737,858 A | 6/1973 | Turner et al. |
| 3,788,742 A | 1/1974 | Garbuny |
| 3,901,602 A | 8/1975 | Gravatt, Jr. |
| 3,915,575 A | 10/1975 | Sick |
| 3,924,252 A | 12/1975 | Duston |
| 4,594,581 A | 6/1986 | Matoba |
| 5,189,631 A | 2/1993 | Suzuki |
| 5,225,810 A | 7/1993 | Inoue et al. |
| 5,266,798 A | 11/1993 | Borden et al. |
| 5,381,130 A | 1/1995 | Thuillard et al. |
| 5,502,434 A | 3/1996 | Minowa et al. |
| 5,530,433 A | 6/1996 | Morita |
| 5,576,697 A | 11/1996 | Nagashima et al. |
| 5,646,390 A | 7/1997 | Wang et al. |
| 5,696,379 A | 12/1997 | Stock |
| 5,751,785 A | 5/1998 | Moorman et al. |
| 5,861,951 A | 1/1999 | Uesugi et al. |
| 5,912,619 A | 6/1999 | Vogt |
| 5,923,260 A | 7/1999 | Endo et al. |
| 6,091,345 A | 7/2000 | Howard et al. |
| 6,119,055 A | 9/2000 | Richman |
| 6,204,768 B1 | 3/2001 | Kosugi et al. |
| 6,292,683 B1 | 9/2001 | Gupta et al. |
| 6,509,832 B1 | 1/2003 | Bauer et al. |
| 6,658,203 B1 | 12/2003 | Oster et al. |
| 6,813,303 B2 | 11/2004 | Matsuda et al. |
| 7,983,445 B2 * | 7/2011 | Knox et al. .................. 382/103 |
| 8,154,724 B2 * | 4/2012 | Mitchell et al. ............... 356/343 |
| 8,406,471 B2 * | 3/2013 | Knox et al. .................. 382/103 |
| 8,427,642 B2 * | 4/2013 | Mitchell et al. ............... 356/343 |
| 8,508,376 B2 * | 8/2013 | Knox et al. .................. 340/628 |
| 8,620,031 B2 * | 12/2013 | Knox et al. .................. 382/103 |
| 2002/0070854 A1 | 6/2002 | Bartholomew et al. |
| 2002/0080040 A1 | 6/2002 | Schneider et al. |
| 2002/0118352 A1 | 8/2002 | Ohzu et al. |
| 2002/0135490 A1 | 9/2002 | Opitz et al. |
| 2002/0153499 A1 | 10/2002 | Oppelt et al. |
| 2003/0189487 A1 | 10/2003 | Mathews et al. |
| 2004/0017505 A1 | 1/2004 | Yamauchi |
| 2004/0051791 A1 | 3/2004 | Hashimoto |
| 2004/0056765 A1 | 3/2004 | Anderson et al. |
| 2004/0080618 A1 | 4/2004 | Norris |
| 2004/0085448 A1 | 5/2004 | Goto et al. |
| 2005/0207655 A1 | 9/2005 | Chopra et al. |
| 2006/0170787 A1 * | 8/2006 | Bentkovski ................ 348/222.1 |
| 2006/0202847 A1 | 9/2006 | Oppelt et al. |
| 2007/0024459 A1 | 2/2007 | Cole |
| 2007/0064980 A1 | 3/2007 | Knox et al. |
| 2008/0061250 A1 * | 3/2008 | Perel et al. ............... 250/492.21 |
| 2008/0297360 A1 * | 12/2008 | Knox et al. .................. 340/628 |
| 2011/0058167 A1 * | 3/2011 | Knox et al. .................. 356/338 |
| 2011/0221889 A1 * | 9/2011 | Knox et al. .................. 348/135 |
| 2011/0243389 A1 * | 10/2011 | Knox et al. .................. 382/103 |
| 2012/0038768 A1 * | 2/2012 | Fujimori ..................... 348/143 |
| 2012/0140231 A1 * | 6/2012 | Knox et al. .................. 356/442 |
| 2013/0121546 A1 * | 5/2013 | Guissin ........................ 382/128 |
| 2013/0170705 A1 * | 7/2013 | Knox et al. .................. 382/103 |
| 2014/0022547 A1 * | 1/2014 | Knox et al. .................. 356/338 |
| 2014/0028989 A1 * | 1/2014 | Butscher et al. ................ 355/67 |

FOREIGN PATENT DOCUMENTS

| | | |
|---|---|---|
| JP | S5622932 A | 3/1981 |
| JP | 62-153780 A | 7/1987 |
| JP | H03245296 A | 10/1991 |
| JP | H06109631 A | 4/1994 |
| JP | H0712724 A | 1/1995 |
| JP | 10154284 | 6/1998 |
| JP | H10232196 A | 9/1998 |
| JP | H11503236 A | 3/1999 |
| JP | 11339150 | 12/1999 |
| JP | 2000-19112 A | 1/2000 |
| JP | 2000019112 A | 1/2000 |
| JP | 2000180349 A | 6/2000 |
| JP | 2002250769 A | 9/2002 |
| JP | 2004257876 A | 9/2004 |
| JP | 5020563 B2 | 9/2012 |
| JP | 5288668 B2 | 9/2013 |
| WO | 2004102498 A1 | 11/2004 |
| WO | 2006/050570 A1 | 5/2006 |

OTHER PUBLICATIONS

European Search Report issued in European Patent Application No. 12183185.3 dated Jun. 20, 2013.
European Search Report issued in European Patent Application No. 12183207.5 dated Jul. 2, 2013.
European Search Report issued in European Patent Application No. 12183148.1 dated Jun. 5, 2013.
European Search Report issued in European Patent Application No. 12183197.8 dated May 10, 2013.
Search Report dated Jan. 24, 2013 issued by the European Patent Office in European Patent Application No. 12182832.1.
Search Report dated Nov. 1, 2011 issued by the European Patent Office in European Patent Application No. 08849716.9.
Office Action dated Jan. 7, 2010 issued in U.S. Appl. No. 10/556,807.
Office Action dated Mar. 17, 2009 issued in U.S. Appl. No. 10/556,807.
Office Action dated Aug. 8, 2010 issued in U.S. Appl. No. 10/556,807.
Allowance dated Mar. 15, 2011 issued in U.S. Appl. No. 10/556,807.
Restriction dated Oct. 19, 2011 issued in U.S. Appl. No. 13/164,123.
Office Action dated May 14, 2012 issue din U.S. Appl. No. 13/164,123.
Allowance dated Nov. 23, 2012 issued in U.S. Appl. No. 13/164,123.
Office Action dated May 8, 2013 issued in U.S. Appl. No. 13/775,577.
Allowance dated Aug. 23, 2013 issued in U.S. Appl. No. 13/775,577.
Office Action dated Jan. 27, 2012 issued in U.S. Appl. No. 11/719,226.
Office Action dated May 29, 2012 issued in U.S. Appl. No. 11/719,226.
Allowance dated Apr. 8, 2013 issued in U.S. Appl. No. 11/719,226.
Restriction dated Feb. 15, 2012 issued in U.S. Appl. No. 12/743,171.
Office Action dated Jan. 14, 2014 issued in U.S. Appl. No. 12/743,171.
Office Action dated May 19, 2014 issued in U.S. Appl. No. 12/743,171.
Communication dated Jun. 3, 2014 from The Japanese Patent Office in counterpart Japanese Patent Application No. 2013-055559.
Communication dated Jun. 10, 2014 from The Japanese Patent Office in counterpart Japanese Patent Application No. 2013-096833.
Communication dated Jun. 3, 2014 from The Japanese Patent Office in counterpart Japanese patent Application No. 2010-196936.

* cited by examiner

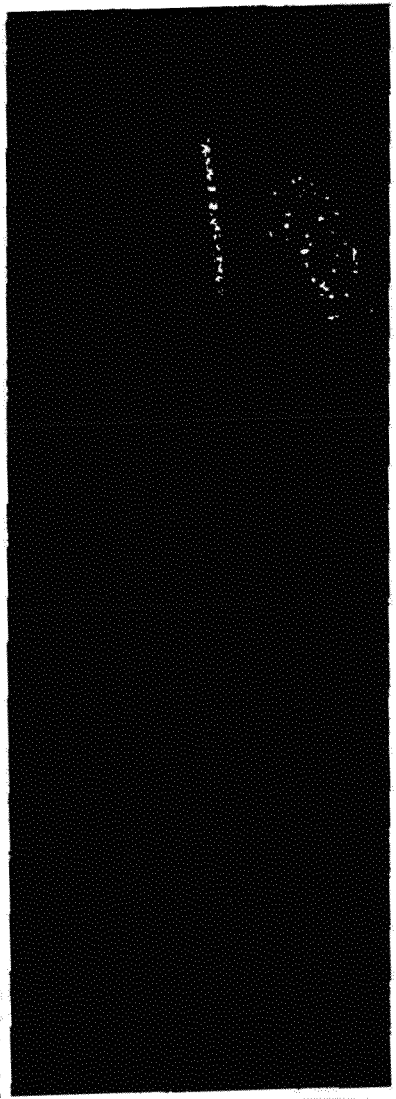

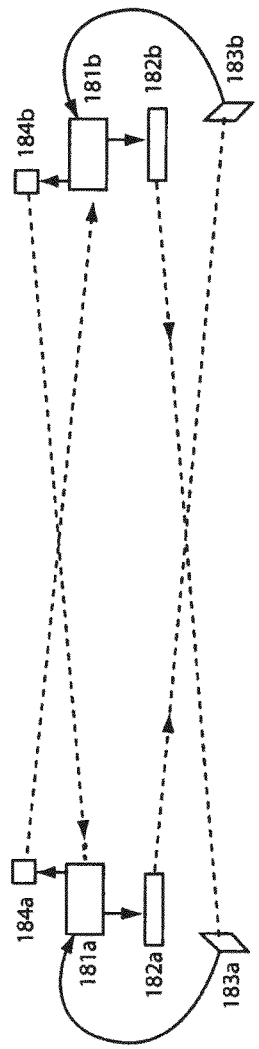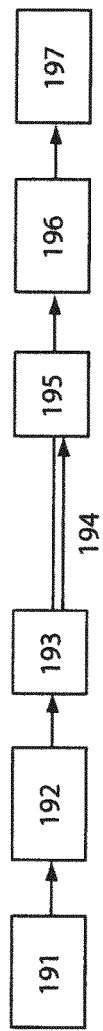
FIG 18
FIG 19

PARTICLE DETECTOR, SYSTEM AND METHOD

RELATED APPLICATIONS

This application is a continuation application of U.S. patent application Ser. No. 11/719,226, filed Sep. 11, 2007, which claims priority to PCT/AU2005/001723, filed Nov. 14, 2005, Australian Provisional Patent Application No. 2004906488, filed 12 Nov. 2004 and entitled "Particle Detector, System and Method" and, U.S. Provisional Application 60/626,960, filed Nov. 12, 2004, the specification thereof is incorporated herein by reference in its entirety and for all purposes.

FIELD OF INVENTION

The present invention relates to an improved sensor apparatus and improved method of sensing. In particular the present invention relates to an improved particle detector and method of detecting particles. It will be convenient to hereinafter describe the invention in relation to the use of one or more emitted beams of radiation, for example, laser beam(s), to detect particles located in an open space, however, it should be appreciated that the present invention is not limited to that use, only.

BACKGROUND OF THE INVENTION

Throughout this specification the use of the word "Inventor" in singular form may be taken as reference to one (singular) or all (plural) inventors of the present invention. The inventor has identified the following related art. There are a number of ways of detecting particles in a region, such as a room, building, enclosure, or open space. Some methods involve sampling air from the region and passing the sampled air through a detection chamber, whereby particles are detected and estimation is made of the amount of smoke, for example, in the region of interest. Such an apparatus is exemplified in aspirated smoke detectors like VESDA® Laser-PLUS™ smoke detectors sold by the applicant.

Other detectors are placed in the region of interest, and use a sensor to detect particles adjacent the sensor. An example of such a detector is a point detector, in which air passes between an emitter and a sensor, and the particles are detected directly in the region of interest.

In both cases if the particles do not enter a sampling point (of the aspirated detector) or pass between the sensor and emitter of the point detector, no particles will be detected. As many buildings employ air handling means for extracting air from a region, such as air-conditioning, there is no guarantee that suspended particles will be detected rather than pass out of the region via the air handling ducts. It can be very difficult to use the aforementioned methods of detecting particles in outdoor areas or very large indoor arenas where there may not be appropriate locations to place a point detector or a sample point and connecting tubing.

Other devices used to detect, for example, smoke include the detector disclosed in U.S. Pat. No. 3,924,252, (Duston) which uses a laser and a photodiode to detect light scattered from particles. This device uses a corner reflector to reflect the light back at the emitter. Duston requires a feedback circuit to detect whether the beam is emitted or blocked.

Another type of detector is known as a "Beam Detector", which measures the attenuation of the intensity of a signal from a projected light source caused by smoke particles suspended in the projected light. These detectors, namely beam detectors and the detector disclosed in Duston, have relatively low sensitivity and are only capable of measuring the total attenuation within the illuminated region.

The above noted detectors may need to address a number of difficulties that are faced when attempting to detect particles by use of emitted radiation in a monitored area that may comprise, for example, indoor rooms, large indoor arenas and outdoor areas. Some of these difficulties comprise the following. The installation and commissioning of equipment to provide emitted radiation and means for detecting the emitted radiation and/or scattered radiation may be onerous. In particular, such equipment may be intrusive to the monitored environment and may require complex connections, for example, wiring or otherwise to supply control, communications and power to the equipment. Additionally, a number of technical personnel with particular skills may be required to install and/or commission the equipment. Once installed and/or commissioned such equipment may be susceptible to environmental conditions that form part of the monitored environment that contribute to drift, misalignment and the like to cause inaccuracies of measurement. Furthermore, there are environmental conditions and events unrelated to alarm conditions that may commonly occur in the monitored environment and may contribute to false alarms when detecting particles. It is desirable to detect particles in large rooms and areas and the physical distances that are involved may contribute to increasing the likelihood of the above noted environmental conditions and events having an effect on the efficiency of detecting particles and also, the distances involved relate to the path length to be travelled by radiation, which of itself requires equipment with high sensitivity and error tolerance.

Nuisance particles such as airborne dust, for example, may be present in the monitored environment and cause false alarms to be raised when there is no actual threat of fire outbreak. For instance, smoke particles are those generated as a result of thermal decomposition, such as in a smouldering fire, whereas nuisance particles may be generated without an underlying fire threat by, for example, mechanical or biological processes. Light scattering characteristics are related to particle size distribution; and there are many types of smoke and many types of nuisance particles and their particle size distributions often overlap. A light scattering method and apparatus using a light scattering cell for chemically identifying individual particles of matter or multiple particles of matter, such as found in aerosols, without collecting and chemically analysing the material is disclosed in U.S. Pat. No. 3,901,602 (Gravatt Jr). According to Gravatt, in the case of single particle analysis, plane-polarized light is impinged on the particle and the intensity of the light scattered into the plane of polarization over a specified angular range is measured. The intensity is related to the particle's coefficient of absorption and its size. In multiple particle analysis, the intensity of the light scattered into a plane perpendicular to the plane of polarization is also measured to determine the total number of particles of matter. This information may be used to normalize the intensity measurement of the first scattered light beam. A smoke detector is presented by Gravatt as an apparatus embodying the multiple particle analysis technique whereby fire-produced aerosols may be detected without interference from non-fire-produced aerosols of similar density.

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

SUMMARY OF INVENTION

It is an object of the present invention to provide a method and apparatus for alleviating at least one drawback of the prior art arrangements.

In one aspect the present invention provides a method of detecting particles comprising:
emitting a beam of radiation into a monitored region, and;
detecting a variation in images of the region with image capturing means such that the variation in images indicates the presence of the particles wherein the steps of emitting and detecting comprise:
determining an ON period of the beam of radiation and an exposure period of the image capturing means in accordance with an indirectly proportional relationship with a power level of the emitted beam.

In another aspect the present invention provides a method of detecting particles comprising:
emitting a beam of radiation into a monitored region, and;
detecting a variation in images of the region with an image capturing means such that the variation in images indicates the presence of the particles wherein the method further comprises the step of:
alleviating one or more of variations and the causes of variations in the detected images that correspond to events other than the presence of particles of interest.

In a further aspect the present invention provides a method of detecting particles comprising:
emitting a beam of radiation into a monitored region, and;
detecting a variation in images of the region with an image capturing means such that the variation in images indicates the presence of the particles wherein the method further comprises the step of:
probing the emitted beam with a probe for commissioning the step of detecting.

In yet another aspect the present invention provides a method of detecting particles comprising:
emitting a beam of radiation into a monitored region, and;
detecting a variation in images of the region with an image capturing means such that the variation in images indicates the presence of the particles wherein the method further comprises the step of:
dividing the beam into a plurality of segments;
determining a variation in images for each beam segment;
providing the determined variation in images for each segment to a control point so as to simulate a plurality of point particle detectors.

In yet a further aspect the present invention provides a method of detecting particles comprising:
emitting a beam of radiation into a monitored region, and;
detecting a variation in images of the region with an image capturing means such that the variation in images indicates the presence of the particles wherein the method further comprises the step of:
determining the position of a predetermined geometric point in space within the monitored region.

In still another aspect the present invention provides a method for synchronising between a light source and an image capturing means comprising:
allowing the source to oscillate on and off at a pre-determined rate;
identifying the source in one or more video images captured by the image capturing means and;
continually modifying the image capturing means frame rate to remain in synchronisation.

In yet another aspect the present invention provides a method of detecting particles comprising:
emitting a first beam of radiation into a monitored region, and;
detecting a variation in images of the region with a first image capturing device such that the variation in images indicates the presence of the particles and wherein the variation in images corresponds to backscattered radiation.

In still another aspect the present invention provides a method of detecting particles comprising:
emitting a first beam of radiation into a monitored region and;
detecting a variation in images of the region with an image capturing means such that the variation in images indicates the presence of the particles wherein the method further comprises:
providing at least one additional beam adjacent the first beam for detecting an imminent intrusion into the beam.

In still a further aspect the present invention provides a method of detecting particles comprising:
emitting a beam of radiation into a monitored region;
detecting a variation in images of the region indicating the presence of the particles wherein at least one of the beam of radiation and a means of detecting the variation in images is adapted to communicate data.

In yet another aspect the present invention provides a method of detecting particles comprising:
emitting a beam of radiation into a monitored region;
detecting a variation in images of the region indicating the presence of the particles;
compensating for distortions in detected images.

In yet a further aspect the present invention provides a method of detecting particles comprising:
emitting a beam of radiation into a monitored region;
detecting a variation in images of the region indicating the presence of the particles;
applying a weighting function to detected images for selectively resolving image portions.

In still a further aspect the present invention provides a method of detecting particles comprising:
emitting a plurality of beams of radiation into a monitored region;
detecting a variation in images of the region indicating the presence of the particles;
adapting the beams to be sequenced in operation.

In still another aspect the present invention provides a method of detecting particles comprising:
emitting a beam of radiation into a monitored region;
detecting a variation in images of the region indicating the presence of the particles;
adapting at least one of a radiation source and a means for detecting the images to be positioned in a controlled manner.

In yet a further aspect the present invention provides a method of detecting particles comprising:
emitting a beam of radiation into a monitored region;
detecting a variation in images of the region indicating the presence of the particles;
wherein the images are detected by image detectors located in at least two positions.

In still a further aspect the present invention provides a method of detecting particles comprising:
emitting a beam of radiation into a monitored region;
detecting a variation in images of the region indicating the presence of the particles;
supervising the beam of radiation.

In still a further aspect the present invention provides a method of detecting particles comprising:

emitting a beam of radiation into a monitored region;

detecting a variation in images of the region indicating the presence of the particles masking a central portion of the detected beam so as to enhance the detection of variations in the images.

In still a further aspect the present invention provides a method of detecting particles comprising:

emitting a beam of radiation into a monitored region;

detecting a variation in images of the region indicating the presence of the particles checking the operation of an image capture means adapted for capturing the images of the monitored region.

In yet another aspect the present invention provides a method of detecting particles comprising:

emitting a beam of radiation into a monitored region;

detecting a variation in images of the region indicating the presence of the particles evaluating the detected images to compensate for interference with the detected variation in images.

In other aspects the present invention provides apparatus adapted to detect particles, said apparatus comprising:

processor means adapted to operate in accordance with a predetermined instruction set, said apparatus, in conjunction with said instruction set, being adapted to perform one or more of the methods as disclosed herein.

Other aspects, preferred features and advantages of the present invention are disclosed in the specification and/or defined in the appended claims, forming a part of the description of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, improvements, advantages, features and aspects of the present invention may be better understood by those skilled in the relevant art by reference to the following description of preferred embodiments taken in conjunction with the accompanying drawings, which are given by way of illustration only, and thus are not limiting to the scope of the present invention, and in which:

FIG. 7a-c shows images illustrating background cancellation performed by the detection system of FIG. 1 in accordance with a preferred embodiment;

FIG. 18 is a top plan view of a further embodiment of the detector system in accordance with the present invention;

FIG. 19 is a block system diagram of a further embodiment of the detector system in accordance with the present invention;

DETAILED DESCRIPTION

Figure 1:
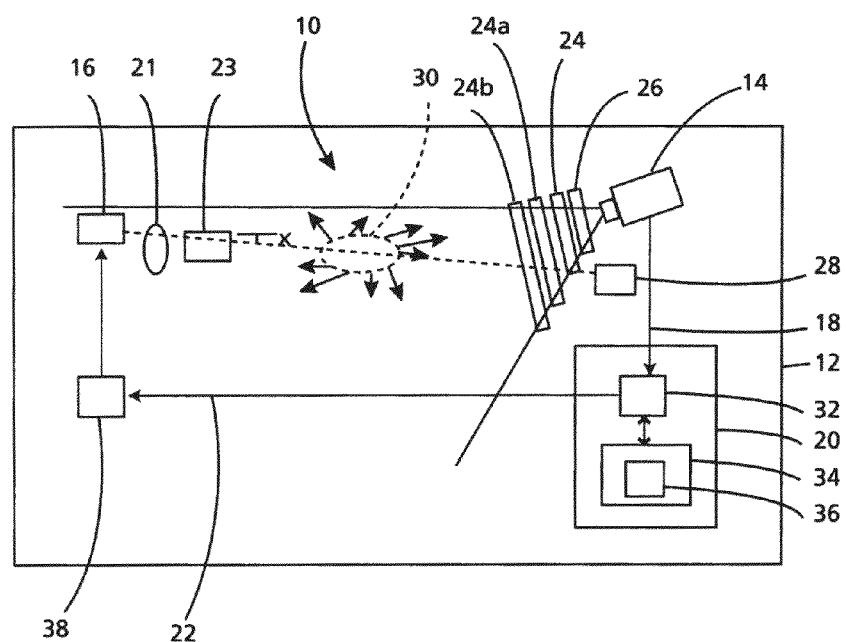
FIG. 1 shows a schematic representation of an embodiment of a detector system from a side view.

In preferred embodiments of the invention, there is provided a method and apparatus for detecting particles comprising emitting a beam of radiation into a monitored region and detecting a variation in images of the region indicating the presence of the particles. More particularly, embodiments of the present invention provide an indication of the location of the particles. In essence, embodiments of the present invention provide a particle detection system, which provides for addressability of detected particles, namely, their location by direct detection without the need for sampling the monitored environment or having to place a detector(s) in a useful location within the environment for particle detection. The beam of radiation may comprise one or more light beams emitted from one or more light source(s) and, variation of images of the monitored region or zone may be detected by one or more image capture devices such as cameras.

In further preferred embodiments of the present invention there is provided a computer program product comprising:
 a computer usable medium having computer readable program code and computer readable system code embodied on said medium for detecting particles within a data processing system, said computer program product comprising:
 computer readable code within said computer usable medium for performing the method steps as disclosed herein.

In a particular form the present invention provides a method of detecting particles comprising emitting a beam of radiation into a monitored region and detecting a variation in images of the region indicating the presence of the particles wherein the method further comprises the step of modulating the beam of radiation. Further steps embodying the method and features of preferred embodiments may include identifying an area of interest in the images, which represents a corresponding zone of the monitored region. Scattered radiation within the zone may be represented in one or more segments of a corresponding image, which allows for the location of the particles in the region to be identified. The location of the particles may be determined in accordance with a geometric relationship between the locations of a source of emitted radiation, a direction of the emitted radiation and a point of image detection wherein, the geometric relationship is determined from the images. The detected variation may be an increase in scattered radiation intensity. The increase in scattered radiation intensity may be assessed with reference to a threshold value. The increase in scattered radiation intensity may be calculated by averaging integrated intensity values from the images. The method may comprise assigning different threshold values for different spatial positions within the region. The method may comprise directing the radiation along a path and identifying a target in the images, the target representing a position at which the radiation is incident on an objective surface within the region. A location of the target in the images may be monitored and the emission of radiation may be ceased in response to a change in the location of the target. The method may further comprise identifying a location of an emitter in the images. Further, the method may comprise determining an operating condition of the emitter based on radiation intensity at the identified location of the emitter. The images may be processed as frames, which are divided into sections, which represent spatial positions within the monitored region. Also, the method may comprise monitoring intensity levels in associated sections of the images and assigning different threshold values for different spatial positions within the region, which correspond to the associated sections.

In another embodied form, the present invention may provide apparatus for monitoring a region, comprising:
 an emitter for directing a beam of radiation comprising at least one predetermined characteristic into the region;
 an image capture device for obtaining at least one image of the region; and
 a processor for analysing the at least one image to detect the presence of, or variation of the at least one characteristic between the images, indicating presence of particles within the region.

The processor may be adapted to determine the location of particles in accordance with a geometric relationship between the locations of the emitter, the directed beam of radiation and the image capture device wherein, the geometric relationship is determined from the analysed images. The apparatus may comprise a plurality of emitters, arranged to direct radiation along different respective beam paths. The apparatus may further comprise one or more filters for adapting the image capture device to capture radiation from the emitter in preference to radiation from other sources. The filters may be one or more or a combination of:
 a temporal fitter.
 a spatial filter.
 a band-pass filter.
 a polarising filter.

The image capture device preferably comprises an attenuator. The attenuator may comprise a variable aperture device.

A plurality of image-capturing devices may be used. Preferably, the image capture device comprises a camera. It is also preferable that the emitter comprises a laser.

In a further preferred form, the present invention provides a method of detecting particles comprising the steps of: determining a path of a beam of radiation comprising placing a first image capturing device to view a source of the radiation and at least a part of the path of the beam of radiation; communicating the position of the source to a processor; placing a second image capturing device to view an impact point of the beam of radiation; communicating related position information of the impact point to the processor; determining the path of the beam in accordance with a geometric relationship between the position of the source and the position information of the impact point.

In yet another preferred form, the present invention provides a method of detecting particles comprising the steps of: determining a region of interest containing a path of a beam of radiation comprising locating a first point, being the position of a source of the beam, using an image capturing device; locating a second point being the intersection of the beam of radiation with a field of view of the image capturing device, determining the path of the beam in accordance with the first and second point; calculating a region of interest containing the determined beam path. The step of locating a second point may be performed with at least one substantially or partially transparent probe and the probe is preferably removed from the beam path once located.

In still another preferred form, the present invention provides a method of determining the level of particles or, in particular, smoke particles at one or more subregions in a region of interest comprising: directing a beam of radiation within the region, selecting a view of at least a portion of a path of the beam with an image capture device, determining the location of the source of the radiation relative to the image capture device, determining the direction of the beam relative to the image capture device, dividing the beam of radiation into segments, determining a geometric relationship between the segments and the image capture device, adjusting a level of light received by the image capture device of each segment so as to allow for the geometric relationship. The segments may comprise at least one pixel and the segments are preferably grouped to form the subregions for particle detection.

In a preferred form, the present invention provides apparatus adapted to detect particles, said apparatus comprising processor means adapted to operate in accordance with a predetermined instruction set, said apparatus, in conjunction with said instruction set, being adapted to perform the method steps as disclosed herein.

In embodiments of the present invention there is provided a computer program product comprising; a computer usable medium having computer readable program code and computer readable system code embodied on said medium for detecting particles within a data processing system, said computer program product comprising; computer readable code within said computer usable medium for performing the method steps of the methods as described herein.

In FIG. 1, an embodiment of a particle detector 10 is shown. The detector 10 is located in a region 12 to be monitored. The region could be a room, stadium, hallway, or other area. It is not necessary for the region to be enclosed or indoor.

An image capture device 14 views at least a portion of the region 12, comprising a portion that contains electromagnetic radiation from emitter 16. The image capture device 14 may be a camera or one or more devices forming a directionally sensitive electromagnetic receiver such as photodiodes or CCD's, for example. In the preferred embodiment, the image capture device 14 is a camera. In the present embodiment, the camera 14 uses full frame capture to capture the images to send analogue video information along communications link 18 to a processor 20. It is not necessary to use full frame capture. However, it is preferable to use full frame capture for engineering simplicity in obtaining images, performance, and minimising installation restrictions. As would be understood by the person skilled in the art, other image capture devices 14 such as fine transfer cameras may be used and methods to compensate for the efficiency of full frame capture that is otherwise not available in line transfer cameras, may be employed. Another communication link 22 provides a connection between the emitter 16 and the processor 20. The processor 20 controls the output of emitter 16, and/or receives information about the output of emitter 16 through the communications link 22. Alternatively, the state of the emitter 16 may be sensed by the camera 14 or determined automatically as disclosed below thus obviating the need for communications link 22. In the preferred embodiment, the emitter 16 is a laser producing visible, infra-red or other suitable radiation. The laser 16 may incorporate a lens 21 and spatial fitter such as a field of view restrictor 23. When a beam of light travels through a homogeneous medium there is no scattering, only when irregularities are present does the beam scatter. Therefore, in the presence of particles such as smoke particles the laser beam will scatter. Furthermore, in accordance with the preferred embodiment, the laser 16 may be modulated, eg "laser on", laser "off" in a given sequence. When no smoke is present, the intensity of pixels in a captured image including the laser beam is the same regardless of the state of the laser. When smoke is present, there is a difference between the intensity of a captured image when the laser 16 is on (due to scattering), compared to the intensity when the laser 16 is turned off.

Optional filters are shown in FIG. 1 in the form of a polarizing filter 24 and a band pass filter 26. The polarising filter 24 is adapted to allow electromagnetic radiation emitted from the emitter 16 to pass through, while preventing some of the background light from entering the camera 14. This is useful if the emitter 16 is a laser emitting polarised light, then the polarising filter 24 can be aligned with the polarisation angle of the laser beam to allow maximum transmission of laser light, while removing some background light, which typically is from randomly or non polarised light sources. It is to be noted that the light source does not need to be a laser for this to be achieved. The second filter 26 is a band pass filter, which attempts to only allow light within a predetermined frequency range (i.e. the frequency of the electromagnetic radiation from the emitter 16). For example, an interference filter or coloured gel may be used as the band pass filter 26. By using a band pass filter (for example allowing substantially only light around 640 nm if a red laser of that frequency is used), significant background light will be removed, increasing the relative intensity of light scattered from particles suspended in the air in the region 12.

Other filtering methods comprise modulation of the laser and use of positional information with regard to the systems components as described below.

The image capture device may employ an attenuator for controlling the radiation received. A controllable neutral density filter arrangement may be used. Alternatively, the attenuator could be in the form of controlling the intensity with a variable aperture. An optional, adjustable, iris 24a may be used to control exposure levels. It can be manually set at the time of installation, or the system could automatically set the exposure according to incident light levels. The reason for this is to minimise or avoid camera saturation, at least in the parts of the field of view that are used in subsequent processing. The iris 24*a* may be a mechanical iris or an LCD iris or any other means to reduce the amount of light entering the camera. Some electronic cameras incorporate an electronic shutter, and in this case the shutter time may be used to control exposure instead of an iris 24*a*. A spatial filter 24*b* is also shown, which may for example comprise a slit for effectively masking the incident light to the camera 14. For example, a slit may mask the incident received light at the camera 14 to conform generally to the shape of the laser beam as it would be projected in the plane of the camera 14 lens. Items 26, 24*a*, 24*b* & 24 may be physically located in a variety of orders or combinations.

In use, electromagnetic radiation, such as a red laser light from emitter 16, passes through the region 12 and impacts on a wall or an absorber 28. The field of view of the camera 14 comprises at least part of the path of the laser, and optionally, the impact point of the laser on a wall or other object in the region 12 that is a permanent structure, which in this case impacts on an absorber 28. Particles in the air in the region that intersect the laser, in this case represented by particle cloud 30, will cause laser light to scatter. Some of the light scattered from particles will fall on the sensor of the camera 14, and be detected.

In the embodiment shown in FIG. 1 the camera 14 outputs analogue information to a video capture card 32 of the processor 20. The video capture card 32 converts the analogue information to digital information, which is then further, processed by computer 34. The processing is undertaken by software 36 running on the computer 34. In the preferred embodiment, the processing is carried out in order to interpret the captured image(s) such that an image plane corresponds to or is mapped to corresponding positions on the laser beam. This may be achieved by relatively straightforward geometry and trigonometry once predetermined location or position information of the system's components is obtained.

In other embodiments it is possible to use a camera 14 which would capture the data and transmit it digitally to the processor 20 without the need for a video capture card 32. Further, the camera 14, filters 24, 26, processor 20 and light source 16 may be integrated into a single unit or units. Also, embedded systems may be employed to provide the functions of at least the processor 20.

A number of camera 14 configurations may be used in this embodiment provided image information in the form of data can be supplied to the processor 20.

In the example shown in FIG. 1, a laser modulator 38 is used to vary the power of the emitter 16. The power level may be changed to suit lighting conditions, meet eye safety requirements and provide on/off modulation. In a preferred embodiment a high power laser to overcome ambient lighting may be used with short pulses to satisfy eye safety requirements. In particular, the effect of ambient lighting may be reduced by combining a higher power pulsed laser and a correspondingly shortened shutter time on the camera. For example, assume that given a laser power of 1 mW and a normal laser pulse rate of 40 msec ON 40 msec msec OFF and that an F number of F5.6 is sufficient to give a required sensitivity indoors with a camera exposure time per frame of 40 msec. The difficulty is that bright sunlight of brightness N times the indoor brightness requires the camera to be stopped down to avoid saturation which reduces sensitivity. In one form the invention provides an embodiment in which an approach is to reduce camera exposure time by a factor of N and reduce laser ON time by same factor of N while increasing laser power by same factor N. The laser may still be pulsed at the same frequency of say 12.5 Hz so the average laser power is the same. The camera frame rate may also still be 25 frames per sec. Equally, the beam may be pulsed up to about 50 Hz and the frame rate may be varied to about 100 frames per sec. The result is that the reduced exposure time of the camera allows the aperture to remain at the indoor setting while bringing the intensity of sunlight ambient lighting back to the same level as indoor lighting. The higher power of the laser during the reduced exposure time means that particle detection sensitivity stays the same as indoors. With respect to eye safety standards, the question may still remain whether a higher power pulsed laser is acceptable. In answer to this, one preferred aspect of the invention provides that the primary light beam may beneficially be pulsed ON, in synchronisation with the camera shutter-open period, for a duration shorter than normal camera frame duration. This gives the benefit that a higher output light power level may be used, and an increased camera aperture, whilst still avoiding saturation of the camera by high ambient lighting. This allows the system to function satisfactorily in high ambient lighting conditions, whilst also remaining conformant with eye safety standards proscribed in various regions of the world. These eye safety standards define the laser power that may be used in a populated open area in a manner that allows the peak laser power to be increased at reduced duty cycles. For example, industry standards permit a Class 2 visible laser operating at 12.5 Hz (half the standard 25 Hz camera frame rate) with an ON period of 40 ms, to have a peak output power of 1.18 mW. In one embodiment the same laser is operated at a reduced ON period of 0.1 ms and may then operate at 5.26 mW. Under these circumstances the sensitivity of the system may be maintained with a more than four-fold tolerance to increased ambient lighting. Likewise it is envisioned that the ON period may be extended to 100 ms or in fact to a duration of about a few seconds for much lower peak output power and alternatively the peak output power may extend up to 500 mW with a correspondingly shorter duration of the ON period, in an alternate form, the ON period of the beam may be greater than or equal to the exposure period of the camera.

The camera 14 shown in FIG. 1 may capture 30 frames every second, the emitter 16 is cycled on for one frame and off for the next. The amount of light in a region is sensed for each frame, and the sum of the light in a region when the laser is off is subtracted from the sum of light received while the laser is on. The sums may be over several frames. The difference between the sum of light received when the laser is on compared to the light received when the laser is off is taken as a measure of the amount of scattering in that region. To act as an alarm, a threshold difference is set and should the difference be exceeded, the alarm may be activated. In this way the detector 10 may act as a particle detector. As measuring the scattered light from particles is known to be a method of determining whether there is smoke in a region, the detector 10 may be used as a smoke detector.

The detector 10 may be set to wait until the measured scattering exceeds a given threshold for a predetermined period of time, before indicating an alarm or pre-alarm condition. The manner for determining an alarm or pre-alarm condition for the detector 10 may be similar to the methods used in aspirated smoke detectors using a laser in a chamber, such as the VESDA™ LaserPLUS™ smoke detector sold by Vision Fire and Security Pty Ltd.

Figure 2:
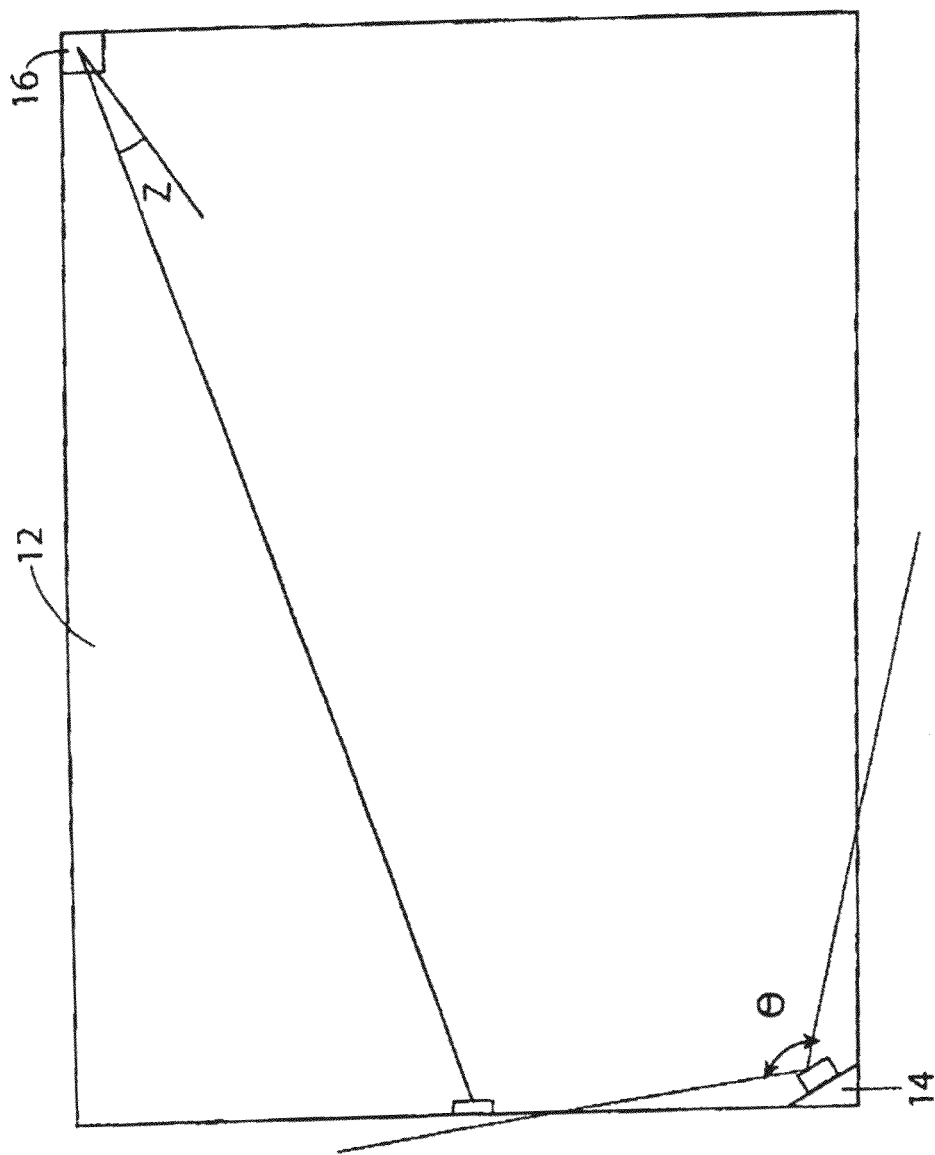
FIG. 2 shows a top plan view of an embodiment of an image capture device and emitter position of the detector system of FIG. 1.
Figure 3:
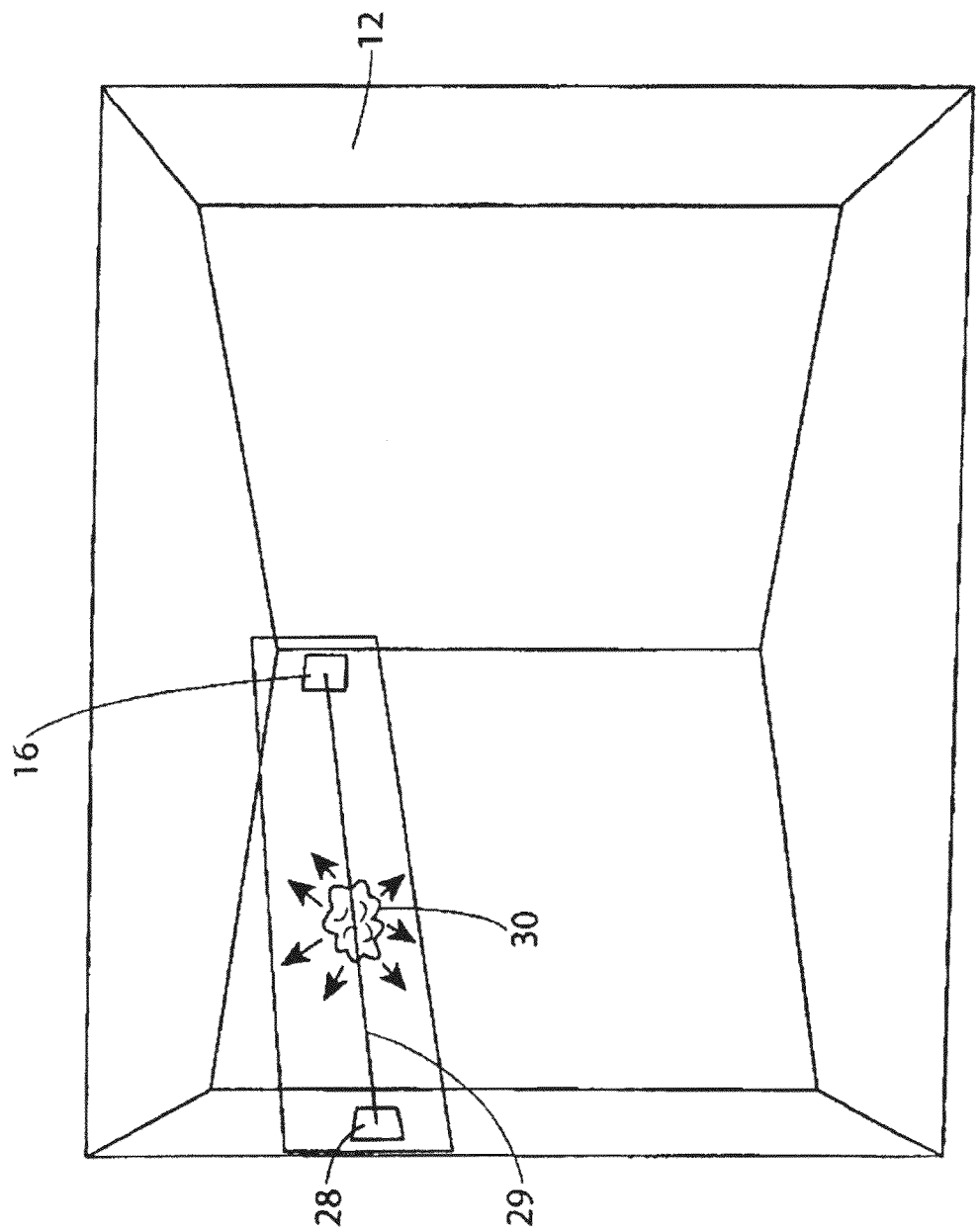
FIG. 3 shows a schematic perspective representation of an image taken by an image capture device of FIG. 2 in accordance with a preferred embodiment.

FIG. 2 shows a top view of the embodiment in FIG. 1. The camera 14 has a field of view θ, which in this case covers substantially all the region 12, which may be a room in a building. The light from emitter 16 is directed generally towards the camera 14, but not directly at the lens. There is therefore an angle subtended by an imaginary line between the camera 14 and the emitter 16, and the direction of the laser beam. The angle may be in the horizontal plane as shown by angle z in FIG. 2, and/or the vertical plane as shown by angle x in FIG. 1. The laser beam does not impact on the camera lens directly. Nonetheless, the laser beam path will be in the field of view of the camera 14, as shown in FIG. 3.

Physical System Variations

It is desirable in some circumstances to use a number of emitters in a system. This may be to comply with regulations, provide back up, or to assist in covering a larger area than could be covered with a single emitter.

Figure 9:
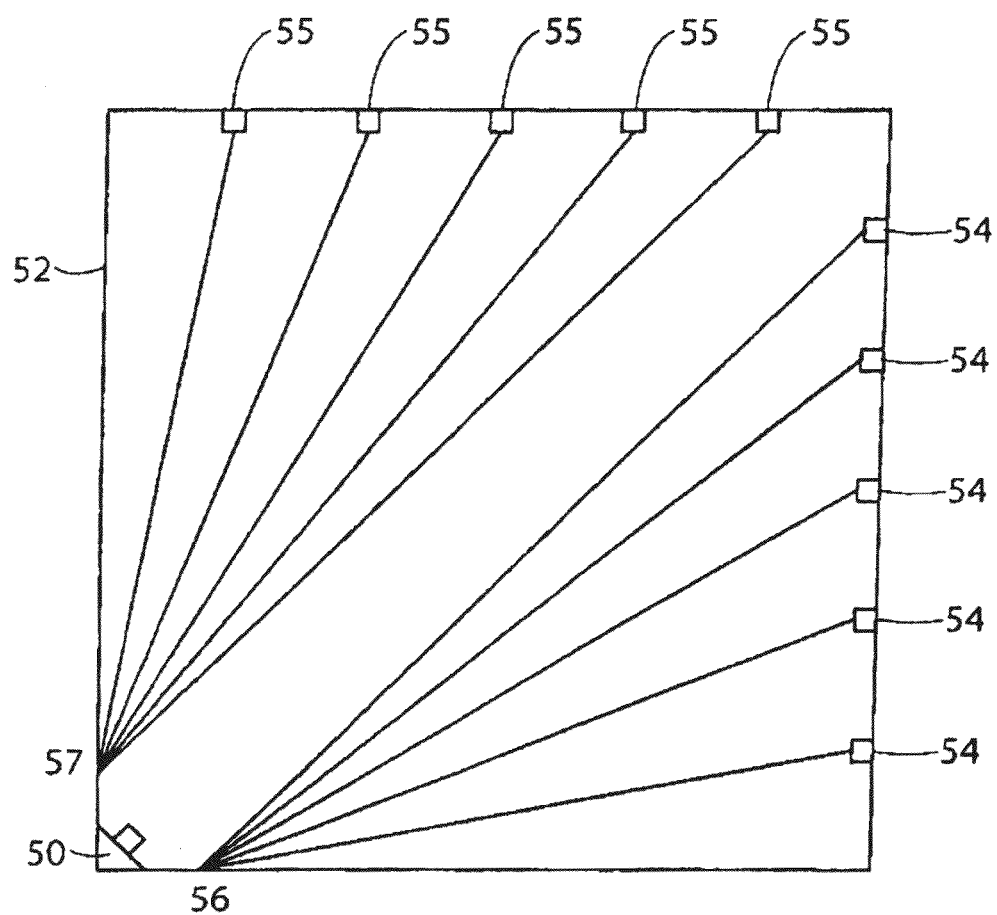
FIG. 9 is a top plan schematic view of a further embodiment of a detector system in accordance with the present invention.

If coverage of a large area is required, it is possible to employ a number of emitters so that smoke may be detected in a number of different locations within a region. FIG. 9 shows an arrangement whereby camera 50 is located within a region such a room 52. If detection was required across a large area, multiple lasers 54 and 55 could be spread around the room to provide coverage. FIG. 9 shows the emitters grouped into two groups, with emitters from group 54 targeted at point 56 and emitters 55 targeted at point 57. The camera 50 may have the points 56 and 57 in view, or may not see the points 56 and 57. Camera 50 may have points 56 and 57 in view by way of an optical arrangement to project an image of points 56 and 57 into the field of view of camera 50, for example, rear view mirrors (not shown in FIG. 9) placed forward of camera 50. Likewise a prism or some other optical system could achieve this result. Further, the emitters 54 and 55 may all be on simultaneously, or may be cycled, so that if the camera 50 can detect the point at which the radiation lands, the radiation detected in the camera can be used to verify that the emitter is operating and not blocked. Detection of individual emitters is possible if they were switched on and off sequentially, or in any sequence of patterns that are not linearly dependant, so that using timing information, it is possible to detect which emitter is on at any one time. Further, knowing which emitter was firing would allow the detector to localise sub regions in the area to be protected and ascertain where any detected particles were located with respect to the sub regions. In effect the beam or beams that have been scattered by particles may be determined.

The emitters 54 and 55 do not all need to intersect on targets 56 and 57, and may be distributed along a number of targets, or cross over each other onto other targets.

Figure 10:
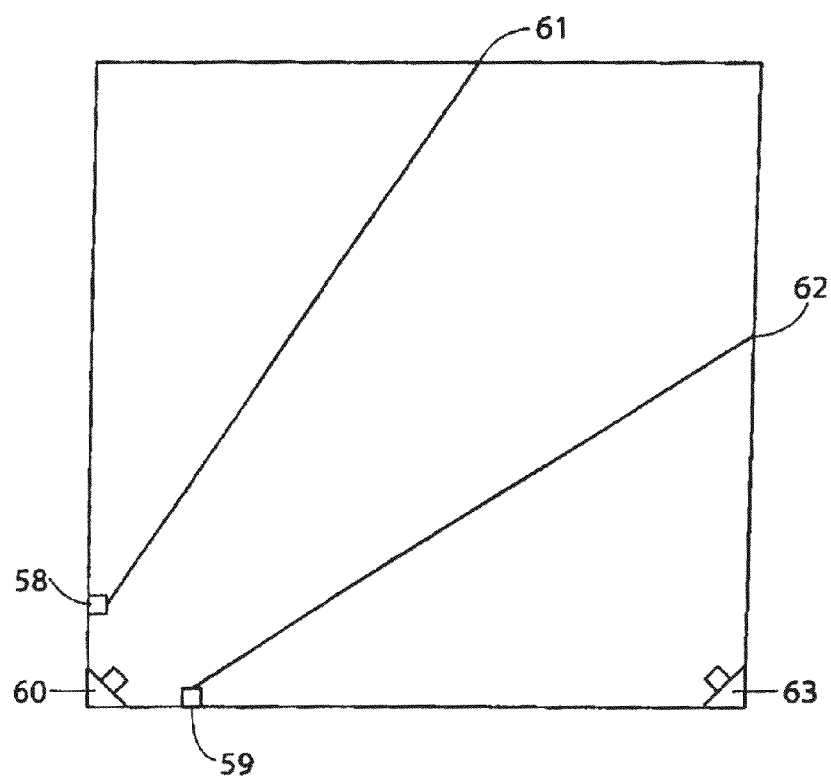
FIG. 10 is a top plan schematic view of another embodiment of a detector system in accordance with the present invention.

An alternative is shown in FIG. 10, where the lasers 58 and 59 are aimed away from the camera 60. The camera 60 can detect a light from the laser light hitting the wall at point 61 and 62. If either of these points disappears, then the detector system knows that either a laser is faulty or something is blocking the path of the laser light. If the laser is blocked, generally the object blocking the laser light will also reflect the light, and therefore the laser spot will shift from the known target area, that is original point 61 or 62. The camera can detect the shift in the spot and may sound an alarm or turn the laser off. This may be important, especially if the laser is not considered eye safe. Another means by which faults may be detected is when a spurious object such as a spider web intersects with a beam causing scattering of the emitted radiation. The silk thread commonly left dangling by spiders when they descend from ceiling to floor level is an example of nuisance objects that although often nearly invisible to the human eye under normal lighting conditions, may be readily detected by the system of the present invention and can easily generate a signal equivalent to a particle density that requires an alarm response. Other nuisance material that may remain suspended in the beam may comprise the nylon line often used to suspend signs and warning notices from ceilings in applications such as retail or decorations such as Christmas decorations. If the sign or decoration itself were suspended at the height of the beam this would necessarily cause an alarm or a fault to be identified and reported, but it is undesirable to report an alarm merely because of the supporting thread.

Any signal from scattering off an object such as a spider's web or other like material may suffer sharper spatial transitions than particles of interest such as smoke. It is also noted that fine objects such as a spider's web are sensitive to polarization rotation. While in operation, it is possible that small amounts of solid material will enter the laser beam and remain effectively fixed, causing a significant amount of light scattering that could be falsely identified as being due to smoke and so cause a false alarm. Several methods may be used to address this problem:

In one embodiment, the laser beam diameter may be made wide in order that the thin fibre intersects only a small fraction of the beam cross-sectional area, and so produces only a small signal, below the alarm threshold. If this small signal remains constant over time (e.g. with a time-constant of 2 hours or more), then it may be subtracted from the reading obtained from that location so as to maintain long-term calibration accuracy.

In another embodiment, occasional movement of the emitted beam, for example by translating the emitter in a lateral direction, may obviate such false detections of scattered radiation. The emitted beam or beams may be translated in directions perpendicular to the beams' direction of propagation. In particular, the laser beam(s) may be momentarily panned so as to give a lateral displacement at the location of the nuisance signal of, say, 50 mm. If the scattering is being caused by smoke then the signal will vary very little as the beam is moved. If a dangling thread, or the like causes the signal, then it will vary sharply.

In FIG. 10 a second camera 63 is shown which may be connected to the system to provide additional views. Using two cameras may allow a more accurate means of locating the area of smoke than using a single camera. Also, the additional view will provide scattering information for different scattering angles for the same particulate material. This data can be used to discriminate between materials with different particle size distributions or scattering properties. This in turn can be used to reduce the system sensitivity to nuisance particles that might otherwise cause false alarms such as dust, for example. With the use of one or more emitters, variation in scattering angle; wavelength of emitted radiation; polarisation rotation; plane of polarisation of viewed scattering and varying the timing of emission and detection all provide means for discriminating between different types of particles.

Given that large particles (often associated with dust) forward scatter more than smaller particles (commonly caused by fire), a determination of particle type can be made. If there is significantly more forward scatter than side scatter for a particular segment of the emitted radiation path, then it may be interpreted that the particle density at that particular segment consists of a proportion of large particles. It may be useful to compare this to other segments or other times, in order to ascertain characteristics of the event that caused the particles to be present in the first place. In a particular embodiment, dust rejection may be achieved by exploiting scattering angle. In this aspect two cameras per laser beam may be used, one at a very shallow angle (say 1 degree), the other at a larger angle (say 30 degrees). The first camera will have much greater sensitivity to large particles (dust). A proportion of its reading may be subtracted from the other camera to reduce sensitivity to dust. The incidence of false alarms may be usefully reduced if the characteristics of the light scattered from the airborne particles is analysed and compared to the known scattering characteristics for a range of smoke types and nuisance particles. The present invention provides a method of determining these characteristics comprising measurement of the scattered light signal strength at varying angles, planes of polarisation and wavelength.

Figure 11B:
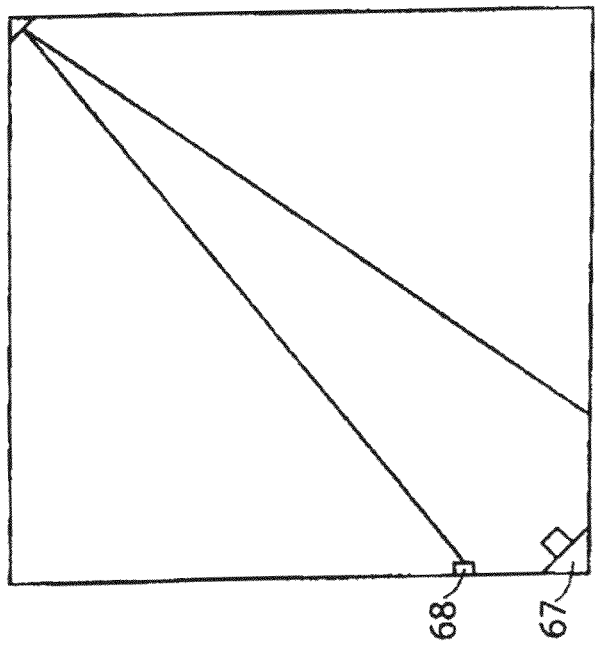
FIGS. 11a-c are top plan schematic views of other embodiments of the detector system in accordance with the present invention.
Figure 11A:
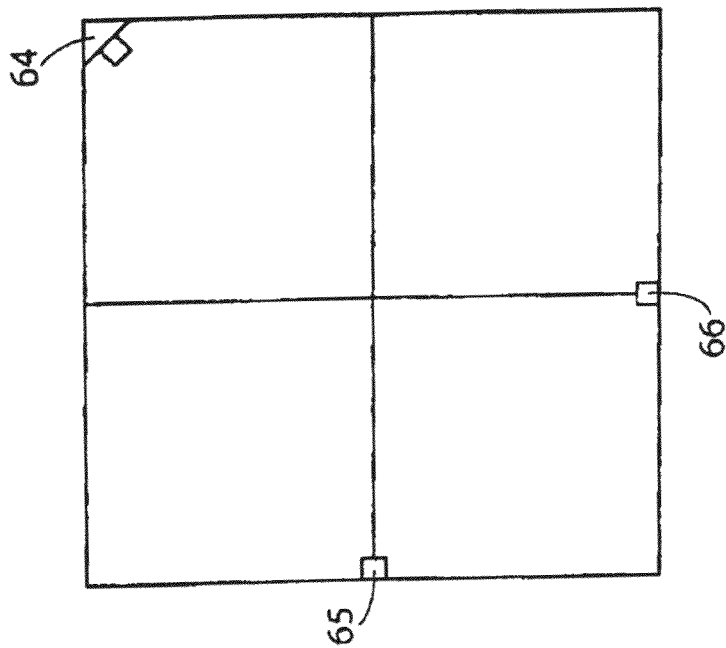

In FIG. 11a camera 64 views two lasers 65 and 66 that cross the room. FIG. 11b uses a laser that is reflected back towards the camera 67, to provide better room coverage and capture both forward and backward scattered light.

In the present embodiment, the processor 10 comprises a personal computer running a Pentium 4 chip, Windows 2000 operating system.

An aspect of the present embodiments is signal processing discussed in detail below with reference to FIG. 4 which is a data flow diagram, the layout of which, would be understood by the person skilled in the art. For ease of reference, the signal processing in this embodiment is conducted using software for the detector 10, referred to generally as the software. It is to be noted with reference to FIG. 4 that the data flow lines indicate image data flow (2-dimensional array data), array data flow (1-dimensional array data) and simple numeric or structured data flow at different stages of the processing. Thus, some of the processing functions described may handle the more intensive image data or optionally, the less intensive numeric data, for example. As would be understood by the person skilled in the art, engineering efficiencies may be attained by choice of the components and software entities used to carry out the processing functions at these respective stages.

Laser State Determination

Figure 4:
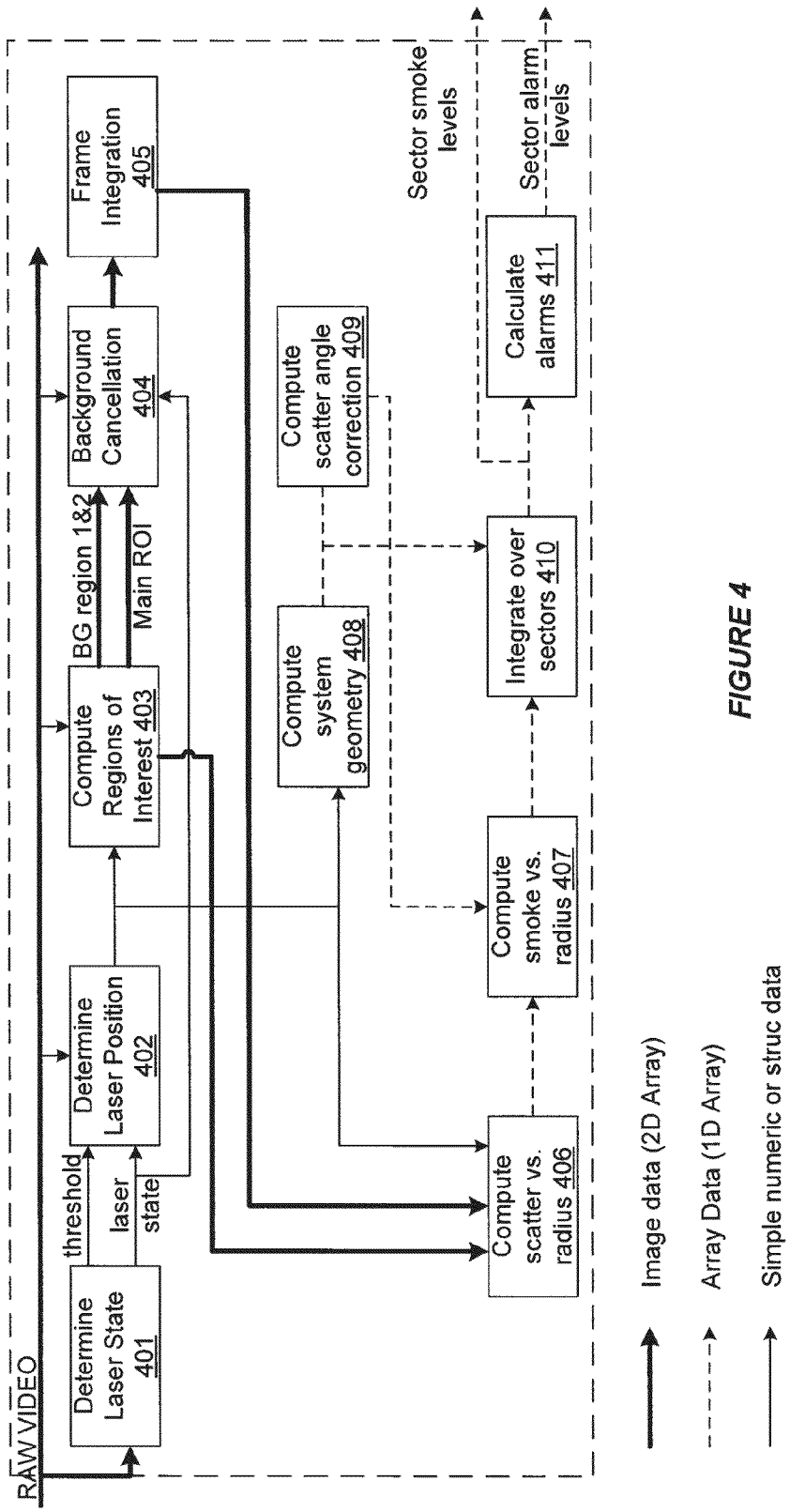
FIG. 4 shows a system overview workflow for signal processing for the detector system of FIG. 1 in accordance with a preferred embodiment.

At step 401 of FIG. 4 a determination of the laser state is performed. The software in this embodiment relies on having the laser source within the field of view of the camera in order to determine the state of the laser for a particular frame.

A small region of interest is assigned that includes the laser source radiation. The centre of the region is set to an initial position of the laser source spot. The average pixel value in the region is computed. It is then compared with a threshold value to make the decision of whether the image records the laser on or off.

The threshold value is the average of the outputs of a peak detector and a trough detector that are fed by the average. Each detector executes an exponential decay back to the current average in the case that a new peak or trough has not been made. The time constant is set in terms of frames, preferably with values of about 10.

This technique has proven to be fairly robust. An alternative method is to look for one or more pixels that exceeded the average in the rectangle by a fixed threshold.

In an implementation where the laser on/off switching is more closely coupled to frame acquisition this function may not be required. However, it can still serve a double check that the laser source is not obscured and is of the correct intensity.

Laser Position

At step 401 of FIG. 4, a centre of gravity algorithm estimates the pixel coordinates of the laser source within the area being monitored. This positional information is optionally updated at every "laser on" image to allow for drift in either the laser source or camera location due to movement of the mounts and/or building over time. The factors affecting the stability comprise movement of walls within the building, mounting point rigidity etc.

More precisely, the threshold established in the previous step (laser state determination) is subtracted from the image and negatives are clipped to zero. The centre of gravity of the same rectangle used in the state determination then yields (x,y) co-ordinates of the laser spot In this calculation, the pixel values are treated as weight.

An alternative technique is to treat the previously described area as an image and calculate an average of a large number (~50) of known "emitter off state" images, then subtract the average from the latest image that is known to have been captured with the emitter on. The previously described centre of gravity algorithm is then applied to the image data to estimate the position of the spot.

Compute Regions of Interest & Background Cancellation

Figure 5:
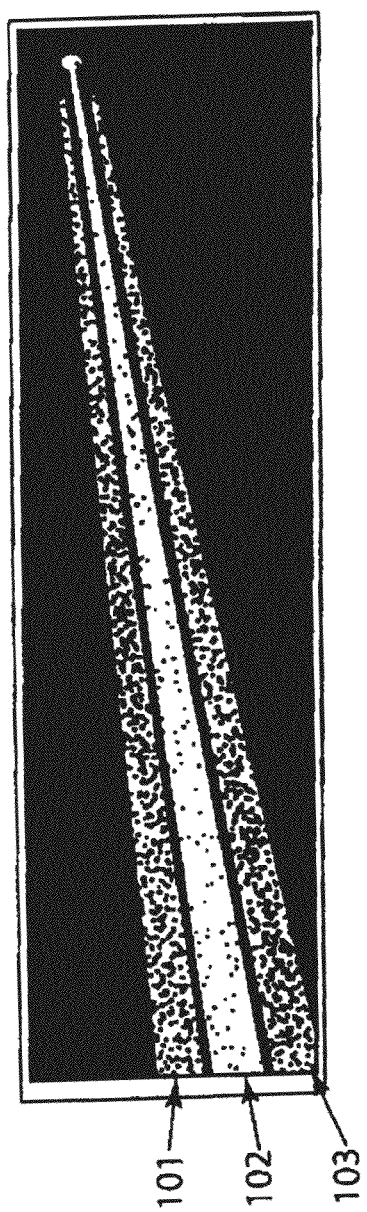
FIG. 5 shows a graphical representation of segmentation of data captured by the image capture device in the embodiment of FIG. 1.

At step 403 of FIG. 4, regions of interest are calculated. At step 404 of FIG. 4, background cancellation is performed. A combination of interpolation and frame subtraction is used during background cancellation to reduce interfering temporally variant and invariant information from the image. The image is segmented into three regions of interest as shown in FIG. 5. The background is segmented into background regions 101 and 103, and there is an integration region 102. These regions are updated periodically to reflect any detected changes in the laser source location. The choice of shape of the regions of interest reflects the uncertainty in the precise position in the image of the scattered radiation. In FIG. 5 the camera cannot see the point where the emitted radiation hits the wall (which occurs beyond the left hand edge of FIG. 5), and therefore the exact path of the emitted radiation is unknown. This produces a region of interest 102 that expands as the distance from the emitter increases. A method of determining the path of the emitted radiation manually is to test the location of the emitted radiation by blocking the radiation temporarily and checking its position, then entering the data manually into the processor. Alternatively, one or more substantially transparent probes, which may be in the form of articles such as plates, may be inserted into the beam. Some scattering wilt occur on entry and exit from the plate providing a reference point or points in the image from which the required integration area and background areas may be computed. In applications where the detector may be used for detecting particles in, for example, clean room or hazardous environments, the windows of such enclosures may act as the substantially transparent plates and, these therefore may establish the path of the beam without the need to intrude into the environments to install the detector system components.

In general a probe or probes that are useful in commissioning the detector use a light-scattering translucent body to indicate to the system the path of the laser beam at one or more points along the beam. As noted, this is to verify that the beam passes where it is intended and that the locations along the beam are being correctly mapped. It is also useful to demonstrate the correct response of the system, without needing to generate smoke in the area, which is often highly undesirable. In applications where the position of the beam may be accessed from ground level using a pole (which may be telescopic or multi-part) it is convenient to attach a sheet of (preferably stiff) translucent material to such a pole. For example, for the purposes of simply intercepting the beam and confirming that the system identifies the correct location of the interception a piece of plain white paper, of for example A4 or letter size, supported on a wire frame may be adequate. In a preferred embodiment, a more sophisticated and useful approach is to use a piece of material with light scattering characteristics that approximately match that of smoke at a known density. For example, a thin sheet of glass loaded with smalt particles of aluminium oxide may be used to scatter approximately 1% of the incident light, which also permits measurement of the effective sensitivity of the detector at that point, and by inference, at all other points in the beam. A three dimensional object rather than a flat sheet may also be used, and may be preferred in some circumstances since maintaining orientation is not then a problem. An example would be a glass bulb, or an inflated balloon of a suitable wall colour and thickness. The latter may even be helium filled and introduced into the beam on a tether from below. Where the laser beam passes through a space that cannot be readily accessed from ground level (for example a sports stadium, or a building atria, some of which are 50 meters and more above ground level) other methods to place the scattering medium into the beam may be required. For example, a small radio-controlled flying device may be used, preferably a rechargeable electric helicopter suitable for indoor use. It is not necessary for this device to be held stationary in the beam for a significant period of time (eg >50 msecs), but merely to cross it on at least one occasion while the laser is on. A suitable example helicopter is the Sky Hawk RIC Mini Helicopter model HP4034, manufactured by Toy Yard Industrial Corporation of Shantou City, China.

The purpose of a narrow integration area is to reduce the noise contributions from pixels that are not contributing a scattering signal and also to allow the background regions to be closer to the integration region thus allowing a better estimate of the correction factor that is used for correcting the illumination level in the laser off images.

The integration region 102 contains the emitted radiation path, while the areas to each side, background region 101 and 103, are used during background cancellation. The regions are generally triangular, that is wider further away from the laser source. This is necessary because while the exact location of the radiation spot is known, the exact angle of the path is not so a greater tolerance is needed at the other end of the path when the camera cannot see where the radiation terminates. There is more noise in a fatter section of integration region due to more pixels, fortunately, each pixel represents a shorter length of the path, so the larger number of samples per unit length allows more averaging. If the camera can see the radiation termination point, there would be less uncertainty of its position and the regions of interest would not need to diverge as much as shown in FIG. 5.

Two background regions 101, 103 are chosen for interpolation of the brightness compensation factor for correcting temporal variations in background lighting on either side of the radiation path in the laser off images. For example, changes in lighting due to two different, independent temporally varying light sources on either side of the radiation path. This principle could be further extended to allow for variations along the path, not just to either side of the path by subdividing the three areas 101, 102, 103 into segments along the length of the radiation path and performing the calculations for each subdivision.

Figure 6:
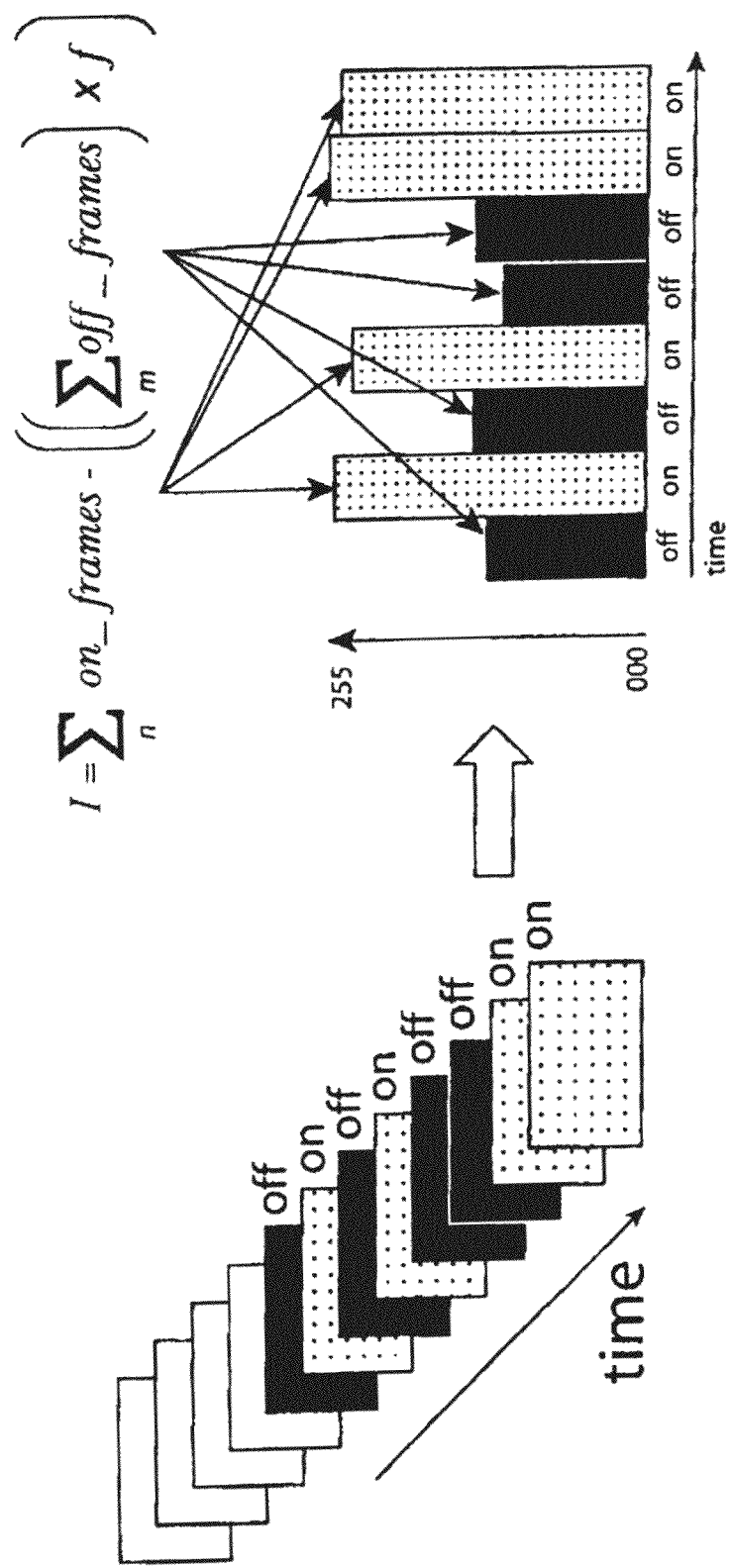
FIG. 6 shows a graphical representation of the integration of the data captured by the image capture device of the embodiment of FIG. 1.

The background cancelling algorithm sums n "on frames" and m "off frames"–the sequence of these frames is arbitrary. Prior to the subtraction of the "emitter off frames from the "emitter on" frames, the "emitter off frames are scaled by a factor, f, to compensate for variance in lumination levels of the images. This may be useful with artificial lighting, the intensity of which varies rapidly. The resultant image contains any differences between the n "emitter on" and m "emitter off" images. This is shown graphically in FIG. 6.

The scaling factor f is determined by interpolation, using the ratios of background variation between the laser on and laser off frames.

$$f = \frac{\left(\frac{\mu_{on1}}{\mu_{off1}} + \frac{\mu_{on2}}{\mu_{off2}}\right)}{2}$$

where:

μ is the average value of pixel intensity in a given background region in either a laser on or laser off frame as designated by the subscripts.

If the processor is not fast enough to keep up with the full frame rate, there needs to be a scheme to allow a random selection of frames to be processed. Since n laser on and m laser off frames are used for the background cancellation, while waiting to accumulate this number of frames, any excess laser on or laser off frames can be discarded.

Alternatively a lock step synchronisation technique could be used so that the computer was fed information about the state of the laser with respect to the captured image. In any case, a minimum of one on frame and one off frame is required for the technique to work.

An alternative to the cancellation scheme described above is to simply subtract laser on and laser off frames. Many on frames and off frames can be summed or averaged or low pass filtered, with the summing, averaging or filtering performed before and/or after the subtraction.

The result of the background cancellation is an image that is predominantly composed of scattered light from the emitter, and some residual background light and noise.

Frame Integration

At step 405 of FIG. 4 frame integration is performed. A number of background cancelled frames are summed, averaged or otherwise tow pass filtered to obtain a scattered light image with reduced noise. By averaging a number of frames, interference that is not correlated with the laser on/off switching is reduced and the wanted (correlated) scattering information is retained. Typically the total number of frames used in the background cancellation and frame integration steps is approximately 100 (i.e. approximately 3 seconds of video). Longer periods of integration or lower filter cut-off frequencies may yield an improved signal to noise ratio, and allow a higher sensitivity system at the expense of response time.

Figure 7A:
Figure 7B:
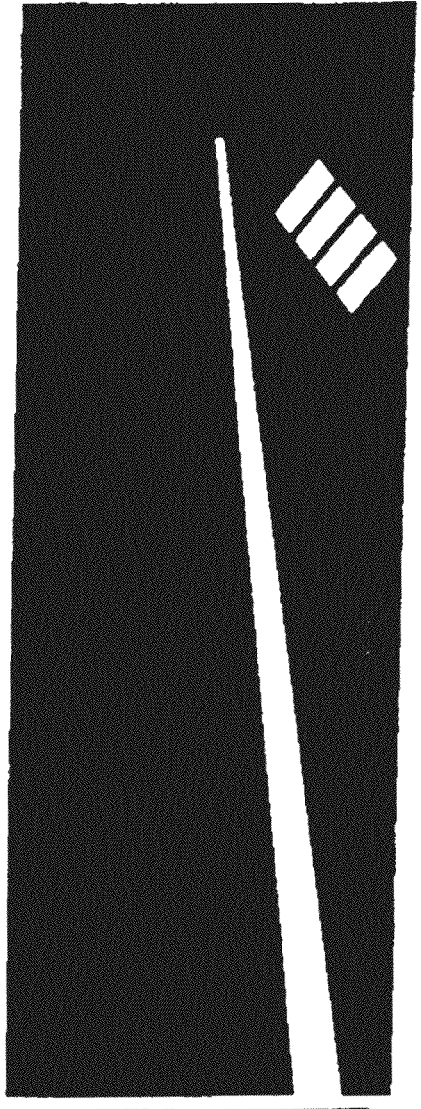

With reference to FIGS. 7a to 7c, the sequence of images shows the effect of background cancellation and integration in the detection of the scattered light. The image intensity has been scaled to allow for better visibility to the eye. The particle obscuration level over the entire beam was approximately 0.15% per meter as measured by a VESDA™ Laser-PLUS™ detector, sold by the applicant. FIG. 7a shows the raw video, FIG. 7b highlights the region of integration, and FIG. 7c the scattered light in the presence of smoke after background cancellation and integration.

Scatter Vs Radius Computation

Figure 8:
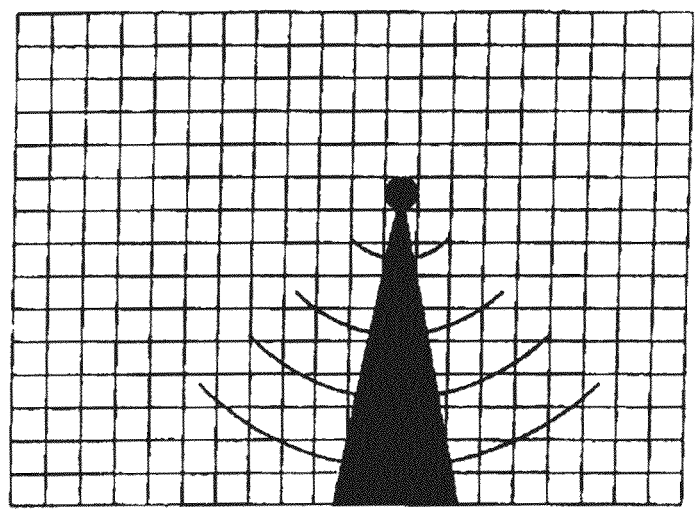
FIG. 8 shows a graphical representation of a method used for calculating pixel radius in an embodiment of the software used in conjunction with the operation of the detector system of FIG. 1.

At step 406 of FIG. 4 computation of the scatter as a function of the radius from the emitter is performed. Variations in intensity along the beam due to system geometry and scattering may be remedied using this method. A data array is calculated containing scattered light levels in the integration region versus radius, for example measured in pixels in the captured image, from the laser source. Since a radius arc covers a number of pixels inside the integration, the intensity of each pixel within a given radius interval is summed together. FIG. 8 is a graphical representation of how the integration region is segmented by arcs centred with respect to the emitter. In FIG. 8, triangle 80 represents the expected integration area and the arcs represent different radii from the laser source. Each portion of the integration area lying between a pair of arcs has its pixels summed and the sum is entered into the scattered light data array. For pixels that are not clearly between two of the arcs, rounding or truncation of the calculated radius corresponding to such pixels can be used to resolve the ambiguity. The contribution of such pixels may also be apportioned to sums corresponding to the adjacent areas, rather than being lumped into one or the other.

Compute Geometry

Figure 12:
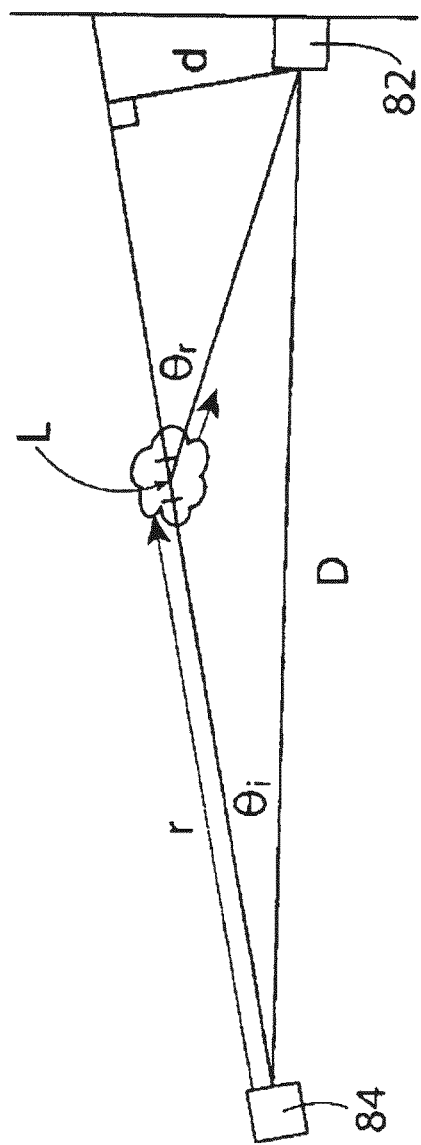
FIG. 12 shows a schematic representation of a part of the detector system of FIG. 1.

At step 408 of FIG. 4, the geometry of the system elements/components is determined. Each pixel as described above (or image point) corresponds to a specific geometric configuration with respect to a scattering volume and the general case of such an image point is shown in FIG. 12. At each such point or pixel, the following parameters can therefore be determined:

1. θ—scattering angle.
2. r—the distance in meters from the laser source.
3. D—distance from camera to laser source.
4. L—physical length viewed by one pixel at a given point along the beam.

A corrected intensity of pixels corresponding to a given radius, r, is then determined for a real world system, in which the intensity of pixels is multiplied by a predetermined scattering gain value, discussed below under Scattering Angle Correction, corresponding to the given radius and a given scattering angle relative to a lossless isotropic scattering calculation. A resultant scattered data array is formed.

Scattering Angle Correction

A correction for scatter angle is logically determined in accordance with step 409 of FIG. 4. As an input, the program requires a scattering data file, which contains for a given material, a set of scattering angles and the corresponding gains. The data in this file is generated by an empirical calibration process, and is intended to contain average values for a variety of smoke types.

At each scattering angle as determined during the above geometry computation, the gain for every scattering angle is derived. The data from the input scattering data file is linearly interpolated so that for every scattering angle an approximation of the forward gain can be calculated.

Compute Smoke Vs Radius

A determination of smoke for a given radius of the beam is performed at step 407 of FIG. 4. To convert the scattered data array to smoke levels on a per pixel basis requires input of data D, d and $\theta_i$, as shown in FIG. 12. Any combination of lengths or angles that constrain the geometry can also be used. D is the distance from the camera 82 to the emitter 84, $\theta_i$ is the angle made between the line from camera 82 and the emitter 84 and the line corresponding to the path of the radiation from the emitter 84, and d is the length of the line perpendicular to the emitted radiation that intersects the camera entrance pupil. From this information, all other necessary information can be determined by trigonometry and geometry. The geometry can be seen in FIG. 12.

For each element in the previously described Scatter vs Radius array, the values of L, $\theta_r$ and r, as shown in FIG. 12, are computed. L is the length of the beam that is visible to one camera pixel.

Integrate Along Beam to Obtain Obscuration

At step 410 of FIG. 4, integration over beam image sectors is performed to obtain the detected obscuration. The beam length is divided into a number of sectors to provide addressability along the beam. In order to distinguish between the laser source and scattering of the laser beam, the pixels around the laser source location cannot be included as part of a sector, as the intensity caused by scattering cannot be resolved, especially for an uncollimated source for which flaring may occur causing residual intensity in the pixels surrounding the source.

Likewise at the camera end, due to the geometry of the set up, the field of view of the camera allows the beam to be viewed to within a few meters of the camera.

In order to provide a smooth transition between sector boundaries, a simple moving average filter is implemented. In fact, the beam is divided into n+1 segments, and then a moving average is applied (of length two segments) resulting in n sectors.

Each pixel along the beam-captured image corresponds to a physical length along the beam see FIGS. 8 and 12. This physical length gets smaller as the beam approaches the camera. So starting at the laser end and ignoring the pixels that are outside the end boundaries, the obscuration for a particular sector is the sum of all the pixel intensities after the application of the correction noted above, which fall into the physical length and position as described by that sector.

For example, to determine the obscuration, O, over the whole beam, given as a sector size in pixel radius, r, as n to m, $$O = \frac{\sum_{r=n}^{m} S(r)L(r)}{\sum_{r=n}^{m} L(r)}$$

where S is scattered light and L is given above.

Figure 13:
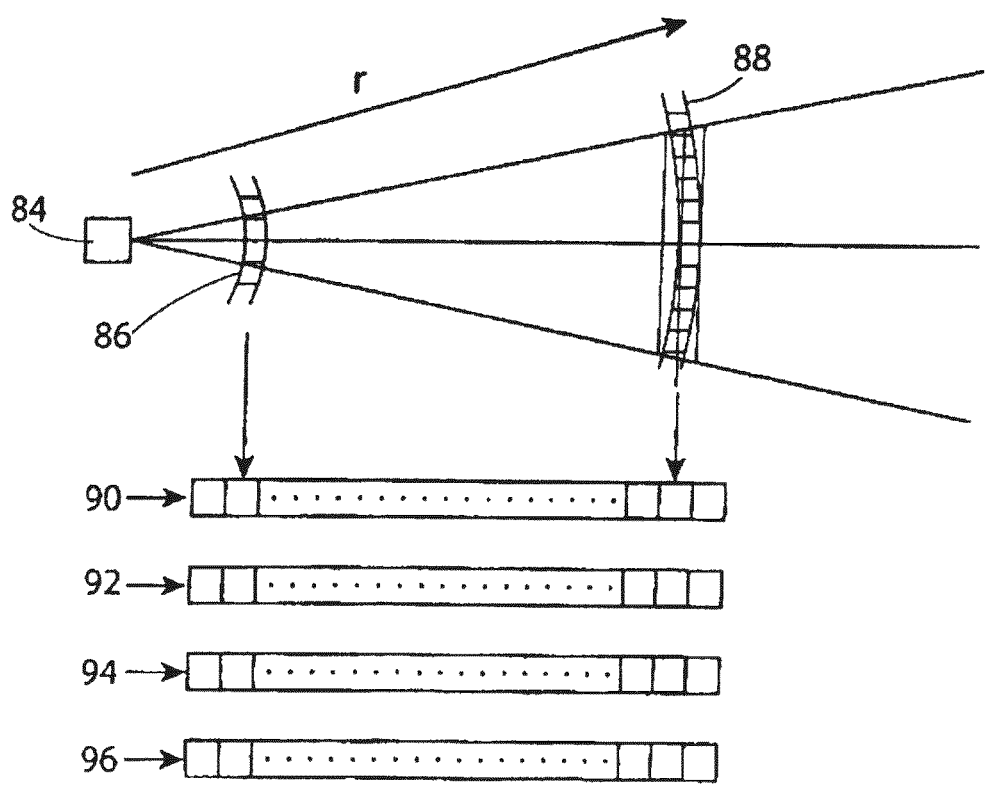
FIG. 13 shows a schematic representation of captured image data from an image capture device of the detector system of FIG. 1.

As noted above, the beam length is divided into a number of segments to determine individual smoke levels for each segment effectively simulating a number of point detectors. The output of these notional point detectors can be provided to a fire panel, which can then display the location of the smoke or fire as it would with normal point-type detectors. The above formula is based on the theory that scattered light emitted from each segment of the emitted radiation will provide a different light output for a given particle density based upon the angle from the radiation path to the camera and the number of pixels per segment. As the path of the emitted radiation comes closer to the camera that is as r increases in FIG. 12 the angle $\theta_r$ increases. The number of pixels that contain scattered light will also increase due to the apparent widening of the beam in the direction towards the camera 82. This increase in width is shown in FIG. 8 and FIG. 13. FIG. 13 shows the emitted radiation from emitter 84. The angle of the radiation spread is amplified for clarity. As the emitted radiation travels further from the emitter (that is as r increases), the number of pixels that coincide with the location of potential scattered radiation increases. At the radius 86, close to the emitter, only two pixels are determined to be within the region of interest covered by the detector, and the light from these pixels is summed and placed into an array 90, being scattered_light(r), which comprises a n times 1 array of information, where n is the number of pixels across the screen. At radius 88, many more pixels are within the area of interest covered by the detector, and they are all summed to obtain the amount of scattering obtained within the covered region of interest. Calculated at array 92 is the scattering radiation angle $\theta_r$, which will be different for each pixel. That is, when r is small, $\theta_r$ will be small, and as r increases, so does $\theta_r$. This information is important, as particles of interest in detecting certain events can have different scattering characteristics based on their size. Very small particles (relative to the wavelength of the emitted radiation) scatter more uniformly regardless of $\theta_r$ (scattering angle), however larger particles scatter more in the forward direction, and reduce intensity as the angle $\theta_r$ increases. Quite often the particles of interest, in this example smoke particles, are relatively small particles and therefore it can be useful to employ a table of effective scaling factors of output of light for given scattering angles θr. Such tables are known m the use of smoke detectors using laser chambers to detect particles.

Array 94 contains the actual radius of the light captured by the pixels. Array 96 comprises the length of the segment of the emitted radiation encompassed by, in this case, one horizontal pixel in the captured image in the frame of the camera. This information is used to ascertain the volume of the emitted radiation and is used to assist in the calculation of the radiation intensity. Also, array 96 contains data on the smoke intensity at each point r, defined as smoke [r].

Alarm State

Finally with reference to FIG. 4, alarm states are calculated. The alarm states for each sector are determined based on thresholds and delays and a priority encoding scheme, as per standard aspirated smoke detectors, or other parameters determined by the user.

The same method is used for the zone alarm level, except that final zone output is the highest sector or the zone level, whichever is higher.

Fault Defection

The system may have provision for the detection of a fault condition, which is essentially the absence of the laser spot in the image. The laser on/off signal duty cycle may be checked to be within 33% to 66% over the number of frames used in one background cancellation cycle.

Alternative Embodiments

A number of alternative embodiments are available, depending on application and desired features. For example, fault detection may be carried out in a number of ways.

In another application, the system described above could be used in applications where measurement of obscuration was important, such as airports where fog may cause planes to divert if visibility falls below a certain level. The system does not require ambient light to operate, and can therefore operate at night without additional lighting. An infrared camera could also be used with an infrared light source, where the light source, if of similar frequency to the detecting light, could be cycled so that the processor ignores frames illuminated for security purposes.

A typical security camera may take 25 images or frames per second. Smoke detection may only require detecting 1 frame per second or less. Therefore the remaining images can be used for security purposes.

To give increased sensitivity, video processing software operating within the detection sub-system (6,7) may be used to eliminate the contribution of nuisance changes in video signals which are not in the location known to be occupied by the light beam. Software based systems which perform a similar function of processing distinct areas of a video image are known, for example in video-based security systems such as Vision Fire & Security Pty Ltd's ADPRO™ products.

The emitter may be a laser, emitting polarised radiation. The laser may emit visible radiation, infrared radiation or ultra violet radiation. Selection of the wavelength of the radiation may be dependent on the characteristics of the particles to be detected, as well as the characteristics of the apparatus and method to be employed in the detection of the particles. Other types of radiation emitter may comprise a xenon flash tube, other gas discharge tubes, or a laser diode or light emitting diode. The light is preferably collimated to at least some degree, but if the optional area segregation using regions of interest is employed, a broader radiation beam may be emitted.

Figure 11C:
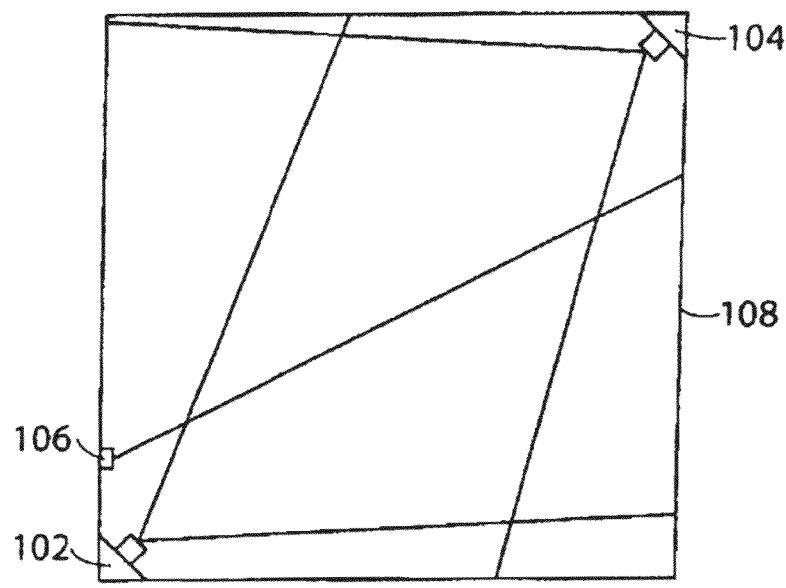

A further embodiment is shown in FIG. 11*c*, which employs two cameras 102 and 104, and a single laser 106. In this embodiment, one camera can view the emitter, and the other the position or target where the radiation hits the wall 108. In such a configuration, it is desirable if the cameras 102, 104 are connected to the same processor or at least communicate with each other. This system provides many advantages, such as confirmation that the radiation is not blocked, and can be used to determine more accurately a position of the emitter radiation with respect to camera 104, which detects the forward scatter of light. As such, the degree of uncertainty of the position of the path of the emitted radiation is reduced, and the regions of interest can be reduced in size, increasing the sensitivity of the detector system.

In one aspect the present invention provides an apparatus and method of detecting particles comprising emitting at least one beam of radiation into a monitored region and detecting a variation in images of the region indicating the presence of the particles wherein the variation in images is detected by at least one or more image capture devices. In particular, use may be made of opposing cameras. More particularly, use may be made of a pair of camera+laser pairs facing each other to:

Monitor each others laser source for integrity (correct operation) and alignment Make alignment easier in the case of infra red (IR) laser (use camera to see the IR dot)

Obtain more uniform coverage in terms of sensitivity and addressability

Obtain backscatter radiation

Figure 14:
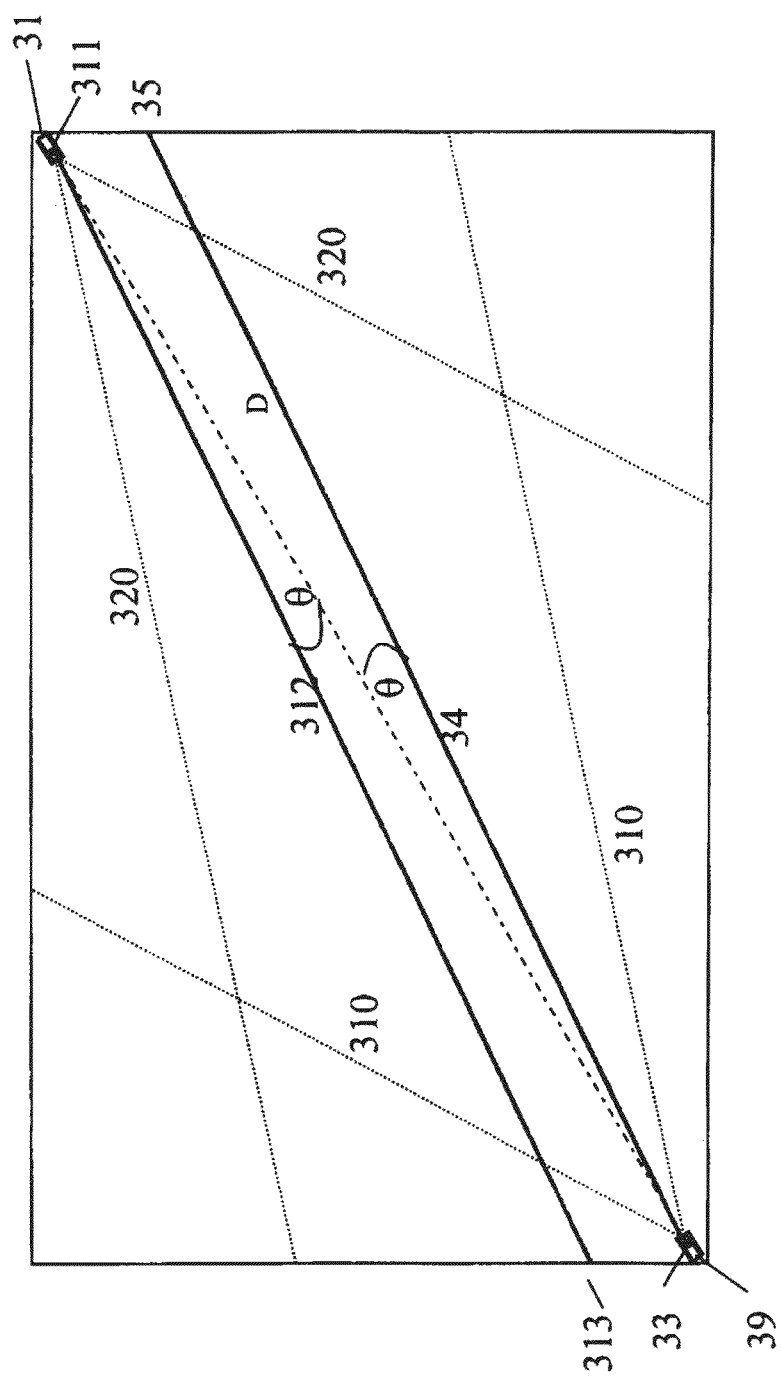
FIG. 14 is a top plan view of another embodiment of the detector system in accordance with the present invention.

In the embodiment shown in FIG. 14 a first camera 31 and a second camera 39 are mounted approximately opposite and facing one another with fields of view 320 and 310, respectively. Laser source 33 is mounted on the same side as camera 39, and in one embodiment may be mounted on the same mount or in the same enclosure to give a cost benefit. Laser source 33 and camera 39 may now be referred to as a "laser/camera pair" 33&39.

Similarly, a second laser source 311 is located on the same side as camera 31 and may also be mounted on the same mount or in the same enclosure to give a cost benefit. So, laser source 311 and camera 31 also constitute a "laser/camera pair" 311&31. Laser sources 33 and 311 provide laser beams 34 and 312, respectively.

Each laser and camera in a pair (33&39 or 311&31) may be pre-aligned at manufacture so that the laser beam emerges at a fixed angle to the centre of view of that camera. This provides the benefit that at installation time the mounting and alignment of each camera simply involves directing the laser beam to point at an approximate predetermined distance from the opposite camera, so reducing installation time and cost.

If the chosen pre-set angle is 8 degrees and the separation between the laser/camera pairs is D meters then the required target-spot to camera separation S is given by $$S = D \tan \theta$$

For example, if θ=2 degrees, and D=50 m, then S is 1.75 meters. In such an example, errors in positioning of for example, +/−100 mm would have an acceptably small effect on the particle density measurement accuracy.

A further benefit of this arrangement is that each laser beam arrival spot indicated in FIG. 14 at 313 & 35 is in the field of view of the opposing camera and can therefore be readily monitored to ensure that the laser source is functioning correctly and the laser beam is unobstructed. This is an alternate form to the 'rear-view' mechanisms as described elsewhere herein.

A further benefit of this arrangement is that it mitigates reduced positional resolution which may be experienced when a single laser beam and one camera is used. In that case the precise position of a particle cloud that is distant from the camera may not be as accurately measured as one that is close to the camera, since its image subtends a smaller angle and therefore fewer pixels in the camera image. With two cameras positional resolution is most accurate at each end of the protected region, and is reduced in the centre by only a much smaller amount. A further benefit of this arrangement is that it permits backscatter from a dense smoke plume to be readily measured. A further benefit of this arrangement is that it facilitates the use of infra-red light, since the camera may be used to image the otherwise invisible target spot when alignment is being performed.

In another aspect the present invention provides an apparatus and method of detecting particles comprising emitting at least one beam of radiation into a monitored region and detecting a variation in images of the region indicating the presence of the particles and further comprising means for determining the position of a given geometric point in space within the monitored region.

It is useful to locate or find the source without the system being "dazzled". In this respect, it is preferable to collimate the laser source using a collimator or like construction with the purpose of shielding the light scattered from the laser aperture from the receiving camera as described elsewhere herein, and use a LED mounted on the laser source to allow an opposing camera to locate the source. The LED may be flashed in synchronism with the laser and its intensity adjusted according to the ambient lighting, either by a photodetector on the source or by feedback from one of the cameras.

It would also be desirable for the system to be autonomously capable of fully checking the optical geometry. This would involve determining the 3D position of both the laser source and a target spot where the laser source arrives relative to the camera location. The minimum requirement for determining the position of a point in space using cameras may be to have either two views from known vantage points of the point in question, or one view of the point and some other means of determining distance, such as angular separation. The physical distances may be provided to the software of the system by the installer one way or another as would be recognised by the person skilled in the art.

By locating another LED at a known position relative to the LED at the source, the angular separation in the images can be measured and the distance from the camera to the LEDs (and therefore the source) can be computed.

Furthermore, by providing two 'rear views' the target spot position may be determined. Thus the system is no longer at the mercy of improper setting of the target spot distance or beam/camera distance. Fully automatic alignment may be possible.

In an alternate form, a camera may capture a view through two pieces of glass or, partially silvered mirrors, or one thick piece. The result is three images superimposed. The first image is the main image of the beam. The second and third images contain the target spot on the wall adjacent the camera. The two spots of the second and third image may not quite coincide. The centre-to-centre distance between the spots combined with the position of each spot in the image, and the known mirror angle and spacing may be sufficient to compute the actual distance to the laser spot in 3D space. The main image may contain some multiple reflections, so the source spot for instance may be seen more than once. The line containing these points provides information as to the orientation of the mirrors in terms of axial rotation. Thus the mirrors may be rotated (axially only) by the installer to allow the target spot to be to the left, right, above or below the camera without the need for any other mechanism to indicate the rotation.

Figure 15:
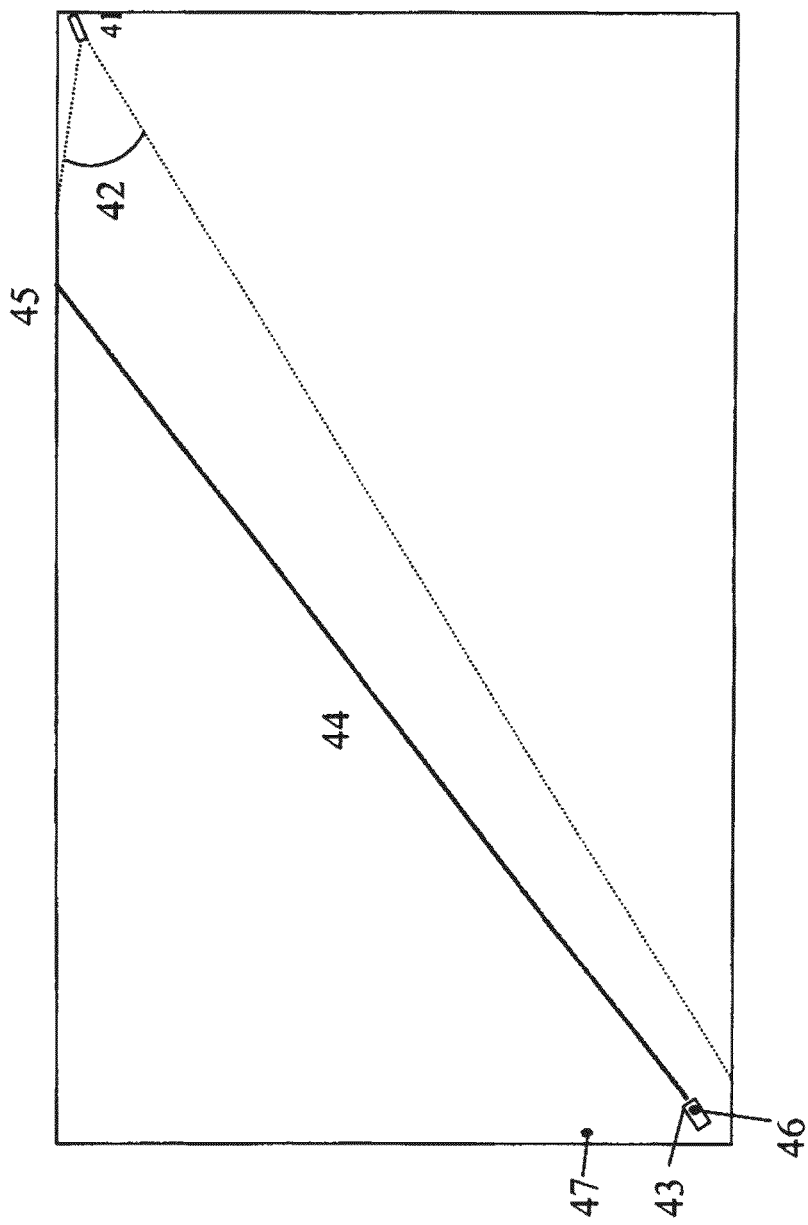
FIG. 15 is a top plan view of a further embodiment of the detector system in accordance with the present invention.

Further description is now provided with reference to FIG. 15. In order to accurately determine the location of any scattering point in the protected space it is necessary for the system to internally model at any time the relative locations and orientations in 3 dimensions of the key optical elements; being a laser source 43, a camera 41 and the laser beam path 44 as shown in FIG. 15.

The laser beam path 44 may be resolved by determining the source 43 location and any other point or, points along the beam, for example the arrival point of the beam indicated by target spot 45 in FIG. 15.

These positions may be determined manually by an installer and provided to the system through a man-machine interface using an arbitrary pre-defined coordinate system. However, it would be preferable for the system to be autonomously capable of fully determining the optical geometry, both for convenience of installation and for ongoing automatic verification that the elements of the system remain properly positioned and aligned. For clarity, the method is described here in reference to FIG. 15 with regard to a single source 43 and a single camera 41, but may equally well be used for multiple sources and cameras.

To determine the source 43 angular position with respect to the camera 41 in its simplest implementation, the light source 43 is in direct view of the camera (indicated by angle 42 in FIG. 15) and the light source output, which may take the form of an aperture, a lens or a transparent window, emits enough off-axis 5 light to allow the camera 41 to identify its position in the image captured by the camera 41. This identification is preferably facilitated by the modulation of the light source 43 in a fashion, which permits image processing software to distinguish the light source 43 from unwanted ambient light sources that do not have this characteristic. However, in practise, it may be desirable that the light source 43 is highly collimated and so there may not be enough off-axis light to allow this. The minimisation of this off-axis light may be deliberately arranged, using field-of-view masks and the like, as it is advantageous to prevent the saturation of the camera image in this region. Consequently, in order to make the position of the laser source 43 distinguishable in the camera image, a further light source 46 with a much less restricted emission pattern may be placed with the source 43 or in close proximity to it. Preferably, a LED 46 of approximately the same emission wavelength as the laser source 43 is used. The LED 46 may be modulated in a fashion which permits image processing software to distinguish the LED emission from unwanted ambient light sources that do not have this characteristic, for example in its simplest implementation it may be flashed in synchronisation with the laser. Further, to minimise the effect of the LED light on the image, and also to minimise any potential nuisance to people present in the room, the intensity of the LED 46 may be adjusted to the minimum level required. This may be variable according to the ambient lighting, as measured by for example a photo-detector at the source 43. Alternatively, the required LED brightness may be adjusted using software processing of image data from one or more cameras 41.

By providing the source 43 with a further LED 47 at a known separation from the first LED 46 the angular spacing between these points may be determined from their respective positions in the camera image and simple geometry may then be used to determine the distance between the camera 41 and the light source 43.

Further, the two LEDs 46, 47 are positioned at a known vertical position, for example, preferably, each LED 46, 47 is installed at the same height so that a line drawn between them is horizontal such that the angular tilt (yaw) of the camera 41 may also be determined. Having established the relative location of the beam source 43 with respect to the camera 41 it is necessary to determine the beam path 44. One or more of the following methods may achieve this:

a) causing the target spot 45 to fall within the direct view of the camera 41;

b) manually or automatically placing a partially scattering medium in the path of the beam 44, either permanently, or as and when it is required, to check the beam position;

c) detecting and recording the scattering caused by airborne dust motes (small particles) that occasionally fall within the beam 44;

d) using a reflecting or refracting device to enable the camera 41 to view a target spot 45 that fails outside its direct field of view;

e) using a further imaging device to monitor the target spot 45 position.

Alternately as noted above, by providing two 'rear views' the target spot 45 position may be determined.

In preferred forms described herein, the present invention provides a method and apparatus for synchronisation between a light source and a camera comprising allowing the source to oscillate on and off at a pre-determined rate, identifying the video image of the source in the camera and then continually modifying the camera frame rate to remain in synchronisation. This has the benefit of reducing cost, for example, of wiring or radio communication between the source and camera. This may also allow for a low cost powering means for the system such that remote positioning of the components is viable by way of using internal battery backup on lasers remote from cameras. Normal power for the laser may be provided from a plug pack or other low cost supply. In other words, a pair of AA NiCad batteries may be sufficient The battery backed power supply should be such as to conform with the requirements for Fire safety systems ie UL approved power supply for fire.

In one particular embodiment the source may fitted with a secondary light source with a wide angle of emission, such as an LED as described with reference to FIG. 15. The LED may flash in synchronisation with the laser light source to facilitate the location of the source in the camera image. Equally, the LED may be turned on and off autonomously, with the camera synchronising to it. While on backup power, the laser could drop the duty cycle to indicate the condition and also to conserve power.

In a preferred embodiment the camera frame rate may be initially controlled to free-run at approximately the same rate as a free-running oscillator in the source. When the flashing source or LED image is subsequently identified, the rate of change of phase between the two oscillators may be identified and a conventional Phase-Locked-Loop feedback method may then be used to adjust the camera frame rate to maintain a fixed phase and so remain in the required synchronisation. Other status info may also be transmitted via the laser modulation or by additional LEDS.

In another embodiment, the source may be arranged to flash not in a simple periodic on-off pattern, but in a more complex, yet predictable, pattern such as a pseudo-random sequence. This permits the source to be more readily distinguished from other nuisance light sources, such as fluorescent lights, which vary in a periodic manner uncorrelated with the source modulation. This benefits both in making initial location of the source in the video image easier and in improving the sensitivity to smoke in the presence of varying ambient light.

In yet another embodiment, the primary frequency of the source oscillator may be altered to be at, or a multiple of, or a sub-multiple of the AC mains electricity frequency (normally 50 Hz or 60 Hz depending on the region) and is synchronised in phase to it. The mains frequency may be sensed directly by a wired input from the mains supply, or may be sensed by an inductive or capacitive coupling, or alternatively may be sensed by a photo-electric detector receiving light from the artificial lighting in the area. Where there is no artificial lighting, then the oscillator may run freely at its default frequency without loss of benefit. In a further embodiment, the primary frequency is set to a frequency very near to that of the AC mains electricity frequency, or a multiple or sub-multiple, but no synchronisation means is provided.

In another preferred aspect the present invention provides an apparatus and method of detecting particles comprising emitting a beam of radiation into a monitored region and detecting a variation in images of the region indicating the presence of the particles wherein the variation in images corresponds to backscattered radiation. In particular, a second laser source may be mounted on a camera, for detecting images of the region, at an angle so that the emitted beam crosses the field of view of the camera, so looking for backscatter at an angle slightly less than 180 degrees to beam direction. In this respect it may be possible to detect backscattered radiation to measure levels of particles that may totally obscure an incoming beam from the first distant laser source. In cases of high smoke levels a beam may be totally obscured from view at a location opposite the smoke event. This aspect is described in more detail elsewhere herein.

Backscatter Geometry

For the purposes of this description "backscatter geometry" may be an arrangement where the scattering angle is greater than 90 degrees. The scattered light may therefore be heading back in the general direction of the source. An embodiment of a backscatter system may have the laser (or other electromagnetic source) built into the same housing as the camera, or alternatively mounted nearby the camera. In a backscatter system, the camera may generally receive much less scattered light than in an otherwise similar forward scatter arrangement. So such a system is generally not preferred for high sensitivity since additional measures may need to be taken to achieve the same performance level as forward scatter detection. However, the backscatter arrangement offers certain advantages, both when used alone and as an adjunct to a forward scatter system.

Figure 16:
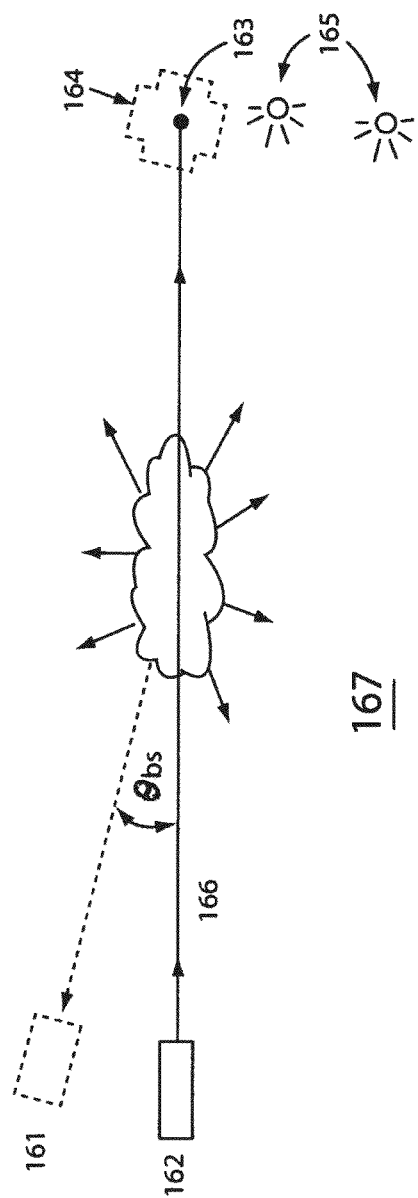
FIG. 16 is a top plan view of a further embodiment of the detector system in accordance with the present invention.

With reference to FIG. 16, there is shown the general physical arrangement comprising a laser 162, camera 161, laser target 164 on which the laser beam may form a target spot 163, and additional light sources 165 as markers. Note that while FIG. 16 shows a number of elements to obtain a specific benefit or function listed below, not all of these elements need exist. The camera 161 and laser 162 may be mounted in the same housing or at least in close proximity. This allows easy installation since there is no need for wiring or power or signals, apart from the light beam 166 itself, to connect the ends of the space being monitored 167. A forward scatter system would require some means of powering the light source 162 that is remote from the camera 161, and also of synchronising the light source 162 to the camera shutter (where correlation techniques are used). A forward scatter system could use a mirror at the far end to allow the laser to be near to the camera, but in this case alignment would be much more critical.

If the laser 162 and camera 161 are either mounted together in the same frame or housing, then they could be factory aligned. This makes installation easier since the installer only has to set the laser's visible spot 163 to fall on the desired target area 164, and the camera 161 will be correctly aligned. If invisible radiation is used, then a monitor showing the image from the camera 161 may be used to assist alignment. The monitor could be a computer with monitor screen connected via a digital data or network connection.

In the case of the factory aligned camera 161 and laser 162 it is not necessary for the distance across the space to be known since the laser video system may measure it itself using the same geometrical techniques as is used for determining the position of smoke particles. Essentially the approach would be to find the laser target spot 163 in the image, using techniques already described, and then convert this image coordinate into a spatial coordinate using the geometric models already described. The advantage here is that there is one less task for the installer to do, or that the installer entered data can be verified by the system.

In any smoke detection system it is desirable to monitor all functions for fault conditions so that the system can be properly maintained. A backscatter system may have the light source target spot 163 in view of the camera 161. Therefore monitoring of the integrity of the light source 162 both in terms of its operation and also for external blockage can be achieved at low cost. The software for determining the presence and position of the spot 163 is likely to be present for reasons mentioned earlier.

A backscatter system is very tolerant of misalignment or alignment drift. This is particularly so if the camera 161 and light source 162 are mounted in the same housing. In fact, it is so tolerant that it may not detect that the camera/laser 161,162 unit has been swung to point in a completely different direction and is thus no longer covering the intended area. There are some techniques for detecting this condition. They are:

1) Use edge detection and correlation to determine whether the scene is substantially the same as when it was originally installed, and raise a fault if it is not.

2) Use a target 164 that is easily recognised using image-processing techniques such as a cross and if the position of the target marker 164 (within the image) moves by more than a threshold amount since the time of installation a fault is raised.

3) Use an additional light source or sources 165 within the field to provide markers. The use of more than one marker 164 allows positive detection of camera rotation. These sources 165 could be synchronised with the main light source 162 to simplify processing. If the position of the source or sources within the image move by more than a threshold amount since the time of installation a fault is raised. These additional light sources 165 could be mounted on other laser/camera 162,161 units mounted in the same general area, thus eliminating the need for extra wiring. The light sources 165 could also be sources that are present primarily for the purpose of particle detection in conjunction with the camera in question or any other camera.

In any scattering based detection system the scattered light is attenuated by further scattering and absorption by intervening particles. In the case of a forward scatter system using shallow scatter angles the path length is substantially the same wherever the scattering occurs. So when the concentration of particulate exceeds a certain value the amount of scattered light received at the camera 161 begins to fall. So forward scatter systems may need an alternative means of measuring particle concentration that is used when high concentrations are experienced. The backscatter system may be used for this purpose since the path length is roughly proportional to the distance from the camera 161 and laser 162. Even when the particle concentration is very high, the scattering that occurs close to the camera 161 can still be received.

In addition to the above, a path loss measurement can be made by observing the intensity of the target spot 163 in the image, compared to the value recorded at the time of installation. This data can be used alone to estimate the average particulate density. The data from this may also be used in conjunction with the scatter information and some corrections to estimate the mean density within segments of the beam 166 despite the particle density having exceeded the turnover point discussed above.

The data from these measurements may also be used in conjunction with the scatter information to discriminate between smoke types and nuisance particles. The technique comprises computing the ratio of scatter to attenuation and comparing this against ratios for known materials. This can be done for the whole beam 166 and also for segments of the beam 166.

In a system comprised of two camera/laser pairs, most of the above benefits can be obtained while maintaining the sensitivity benefits of forward scatter.

In another preferred aspect the present invention provides an apparatus and method of detecting particles comprising emitting a beam of radiation into a monitored region and detecting a variation in images of the region indicating the presence of the particles and further comprising at least one additional beam adjacent the beam for detecting an imminent intrusion into the beam.

Lasers of sufficient power can cause eye damage and even skin damage. It would be undesirable for a system of the present invention to present a safety hazard. The simplest approach to having a safe system is to keep the laser power sufficiently low, but this may compromise the sensitivity of the system. An alternative is to have a scheme to switch the laser off or to a safe power level whenever there is a risk of exposing human tissue or the like. It is also important that such a system does not switch the laser off unnecessarily since continuity of smoke detector operation is also important.

Figure 17:
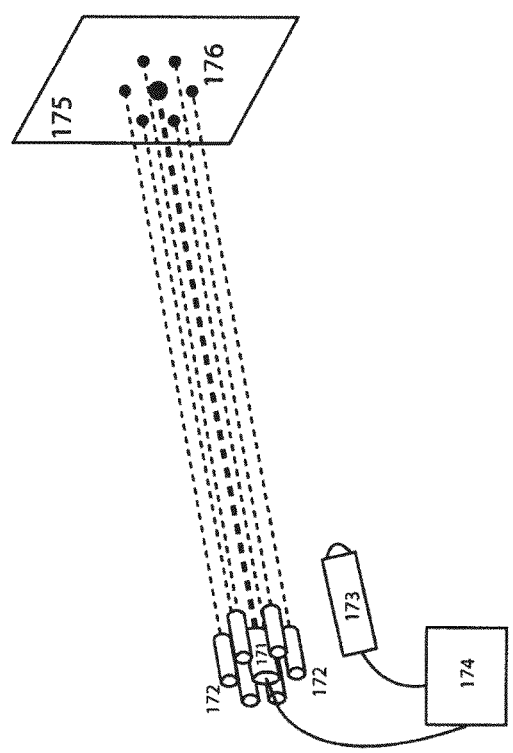
FIG. 17 is a perspective view of a further embodiment of the detector system in accordance with the present invention.

FIG. 17 shows a representation of a laser interlock system where a high power laser 171 is inside a ring of low power eye-safe lasers 172. The outer beams are spaced sufficiently closely (eg 100 mm apart) so that it is impossible for a human eye to be subjected to the laser beam from the main laser 171 without first having blocked one or more of the outer beams. A camera 173 senses the laser light scattered from the target 175. Processing hardware and software 174, process the images to determine the presence or absence of the target spots 176 corresponding to the outer lasers. If one or more of these target spots are absent the processing hardware and software turns off the high power laser. The high power laser is not allowed to operate again until all of the target spots are present in the image.

The spacing of the outer beams is chosen so that at the highest expected velocity of a human head there is insufficient time for the eye to reach the main beam before the camera and processing system has detected the intrusion and turned off the main beam.

Background Cancellation

Techniques for reducing the effects of background light as already described can be used to enhance the Image of the target spots 176. The outer beams may need to be switched on and off for these techniques to work. Depending on the delays in the camera and image acquisition and processing system it is possible to reduce the response time by operating the outer beams in the opposite phase to the main beam.

Alternatively, the outer beams may be left on most of the time, with only occasional image frames taken with the outer lasers off for use in background cancellation processing. If the interlock response time is too long at the time these off frames are being acquired, then the main laser 171 may also be disabled during these periods.

Active Target

Instead of using a camera to collect an image of the target, the target may have photo-detectors mounted on it. Such detectors may already be present for the purposes of maintaining or monitoring system alignment.

Shorter interlock response delays are possible with this arrangement since the camera frame rate limitations are removed.

Cage Propagation Direction

The outer lasers beams do not need to propagate in the same direction as the main laser. These laser sources could be mounted around the main laser target, and propagate towards the main laser source, landing on targets points around the main laser source. The advantage of this arrangement is that the same camera that is used to detect forward scatter from particles in the main beam can also be used to capture images of the outer laser beam target spots.

Camera Laser Pair Configuration

A pair of cameras and lasers can be arranged to provide mutual supervision as described elsewhere herein. In this case they can also perform the image collection, processing and main laser control for the interlock function.

Tube

The protective beams could be a tube of light rather than separate beams. Such a tube of light would appear as, for example, a circle or ellipse at the target. The image processing software would then need to detect interruptions or shadows in the expected ellipse. There are several image processing techniques that could be used as would be appreciated by the person skilled in the art.

Note that the tube does not have to be circular, and it does not even have to be hollow. A solid cylinder will also work. The expected target shape will then be a filled circle, ellipse or other shape. Again, the image processing software would then need to detect interruptions or shadows in the expected ellipse.

Hologram

An interference grating or hologram can be used to create the outer beam or beams from a single laser source. The single laser source could be the main laser 171, or an independent laser.

Virtual Cage

An alternative to an actual cage of lasers is to use a ring of light sources (that are not necessarily tightly collimated) around the main laser. A camera mounted at the main beam target near the axis of the main beam views the light sources. For an intrusion to enter the main beam it must first block the camera view of the outer light sources. Similar processing to that required in the previous arrangements can then provide the interlock function.

Video Motion Detection

In another embodiment image processing techniques such as video motion detection used in security products sold by Vision Fire and Security Pty Ltd may be used to detect an object, such as a person, approaching too closely to the hazardous laser beam. The signal from this may be used to switch off the beam or reduce the laser power to eye safe levels. This technique may not be applicable in darkness, but is nonetheless useful since a high power laser would not generally be required when the ambient lighting is low.

In another preferred aspect the present invention provides an apparatus and method of detecting particles comprising emitting a beam of radiation into a monitored region and detecting a variation in images of the region indicating the presence of the particles wherein at least one of the beam of radiation and a means of detecting the variation in images is adapted to communicate data.

In most fire protection systems, the installation of wiring is a significant contributor to the total system cost. Wireless systems based on radio communication equipment dedicated to data communications provide an added cost to systems.

The following is a list of some of the data that may need to be communicated between different parts of a detector system in accordance with embodiments of the present invention:

1. Camera/Laser synchronisation or timing Information
2. System Configuration Data
3. Laser intensity, duty cycle and camera exposure commands
4. Laser & camera alignment data (for active alignment and/or fault monitoring)
5. Laser enable/disable commands in multi-laser systems
6. Laser marker activation/de-activation/duty cycle/intensity control commands
7. Laser polarisation or wavelength switching commands
8. Fire Alarm status for reporting to the fire panel or other external systems Optical communication may be used in conjunction with radio based communication to improve the overall communication reliability.

In accordance with a preferred form of the invention, the optical transmission of the emitted radiation source(s) may provide a data communications path between all of the data processors within an area to be protected. One of the processors may act as a point for connection to external systems, such as a fire alarm panel. Optionally, two or more such points having independent data paths to the fire alarm panel may be used to provide a fault tolerant reporting path.

The exact needs of a specific system will depend greatly on the complexity and type of system configuration. However, in general, available bandwidth should be the measure used to distinguish the classes of communications solutions and their utility. Solutions that use a camera will be bandwidth limited in some way by the frame rate of the camera, while solutions that use some other photo-sensor will not have this limitation and so should, in principle, be capable of higher bandwidth.

In FIG. 18 there is shown an example system comprised of two cameras 181a & 181b and two lasers 182a & 182b arranged to allow mutual monitoring of the integrity of the laser beams. This concept is discussed more fully elsewhere herein. Two photo-detectors 183a & 183b convert a portion of the incident laser signal into an electrical signal. The received signals are passed to processing electronics within or associated with the cameras 181, which in turn generate control signals that are fed to the lasers 182. To reduce the effect of background light, the photo-detectors 183 may employ an optical band pass filter such as an interference filter or a coloured dye filter. A polarising filter may also be used if the laser is polarised. Linear or circular polarisation may also be used.

The main sources of interference can be expected to be of a DC or low frequency nature from sunlight or man-made light sources. An approach to dealing with this sort of interference is to frequency-shift the data away from the frequencies where interference exists, in this case upwards. FIG. 19 shows such an arrangement where the processor 191 feeds data to a modulator 192 which in turn feeds the frequency shifted data to the laser 193. The laser 193 generates amplitude modulated laser light 194 in accordance with the signal from the modulator 192. Photo-detector 195 converts the received light back into an electrical signal, which is then sent to demodulator 196 before being passed to processor 197.

Many modulation techniques may be employed in accordance with the present invention. Some examples are given below.

One approach is to amplitude-modulate the laser with the serial data stream. If the background light levels are low enough then this will work. The statistics of the data stream may cause some variation in the average laser power. This in turn will affect the sensitivity of the system, although since the effect is calculable it could be corrected for. The data can be encoded to reduce or eliminate the variation in the average power. For example the data can be randomised by an "exclusive or" operation with a pseudo-random sequence. Data compression techniques can also be used since they will tend to randomise the transmitted data stream.

Another scheme is Manchester encoding, since it results in a constant average power and no DC data content.

Pulse position modulation may be used. In this case the pulses could be short periods where the laser is switched off or to a lower power, with much longer intervals in between at the full power. Such a scheme offers near constant average power, and a higher average power to peak power ratio than Manchester encoding.

Pulse width modulation could also be used. Again the case the pulses could be short periods where the laser is switched off or to a lower power, but rather than varying the position in time, the duration or width is varied. Provided that the pulses are short compared to the time in between, then the average power to peak power ratio will be high and the variation in the average will be low. The data can be encoded to reduce or eliminate the variation in the average power. For example the data can be randomised by exclusive or with a pseudo-random sequence or it could be Manchester encoded prior to the pulse width modulator. A variation on pulse width modulation would use absent pulses instead of a non-zero width. In this case the absence of a pulse at the expected time represents a specific data symbol in the same way as a pulse of a particular width represents a specific, but different data symbol.

Also, many of the above techniques can be combined, and some other techniques that could be employed are sub-carrier with frequency shift keying, sub-carrier with phase shift keying, sub-carrier with amplitude shift keying and spread spectrum techniques.

Since a camera may only give an update of the light level falling on a pixel once per frame, the data rate is limited by the frame rate. This would imply a rate of only 30 bits per second with a frame rate of 30 Hz. However, there are techniques that may be used to increase the data rate beyond one bit per frame.

Ambient lighting is a noise source that may interfere with the data communications. Optical filtering as previously described can be employed. Since the camera is primarily present for smoke detection purposes, the filters are likely to be already present.

The methods already described for minimising the effects of background lighting on smoke detection performance are also generally also applicable to data reception, and will not be discussed further here.

Many of the modulation or encoding schemes discussed in the previous section can also be used in the case that the receiver is a camera. In order to mitigate frame rate imposed limitations, data compression is particularly desirable.

Since most cameras will integrate the received photons over a defined exposure period, the emitter duty cycle during the exposure period can be varied to get same result as varying the actual intensity. In some cases this will be a lower cost implementation.

A method that makes use of hardware already present in the example of FIG. 18 is to modulate the intensity of the laser with the data. The laser must be visible within the field of view of the camera, and must have sufficient output directed towards the camera for it to overcome the background lighting variations. These conditions should already be met in many embodiments of the invention as part of the laser beam integrity monitoring.

There are many methods for encoding the data and some examples follow. For the sake of explanation it is assumed that in an system of the invention that does not send data via the laser, the laser is simply driven on and off in alternate frames. The transmission of data is then just a matter of varying the pattern of on and off periods or frames, and/or varying the intensity, and then identifying the variation at the receiving-end camera and processor.

Following a synchronising sequence, the regular laser on-off drive can be exclusive or-ed with the data stream before being applied to the laser modulator. One bit is transmitted per two frames in this method. This method can be regarded as a form of Manchester encoding. The main advantages of this method are simplicity, robustness, and that the average duty cycle of the laser is unchanged by the data. The data rate is however very low. Data compression methods may help recover some bandwidth.

A higher data rate may be achieved by transmitting one bit per frame by applying the data stream directly to the laser modulator. In order to keep the average laser duty cycle within acceptable limits for smoke detection operation, some means are still required limit long runs of the same symbol. Again randomising and/or compression techniques may be used.

It is also possible to increase the date rate further by using multi-level encoding. For example for different laser intensities such as 0%, 33%, 66% and 100% of full power could be used to encode two bits per frame. External optical noise, camera internal noise, and overall system gain stability will limit the number of levels that can be used.

Instead of using the laser alone as the data transmitter, additional light sources that can be modulated may be used, as represented by items 184a and 184b in FIG. 18. If optical filtering is used at the camera, the light source(s) chosen must emit at the corresponding wavelength and polarisation, or be of sufficient intensity to overcome the filter losses. Light emitting diodes (LED) are well suited to the purpose.

For example, an array of 4 LEDs can transmit 4 times as much data as one light source alone. Any of the preceding methods for data encoding can be applied. The LEDs must be sufficiently spaced so that they can be distinguished at the camera as individual sources.

If a colour camera is employed, then the camera can measure the intensity of up to three differently coloured LEDs, even if they appear at the same point in the image. Three separate LEDs can be used, or an RGB LED can be used. In this way, 3 bits of data can be transferred per frame per RGB LED. Again, any of the preceding methods for data encoding can be applied. For example, a four-level encoding scheme with one RGB LED could be used to transfer 6 bits per frame.

In another preferred aspect the present invention provides an apparatus and method of detecting particles comprising emitting a beam of radiation into a monitored region and detecting a variation in images of the region indicating the presence of the particles further comprising means for compensating for distortions in the detected images.

With reference to detecting images, most lenses will produce some degree of image distortion compared to a pinhole lens. Typically the distortion is a radial magnification around a distortion centre that usually is close to, but not necessarily exactly on the optical centre line. The distortion is often termed "pincushion" or "barrel" distortion depending on whether the magnification increases or decreases with radius from the distortion centre.

Lenses with narrow fields of view, for example less than 20 degrees do not generally produce enough distortion to significantly affect the operation of an image capturing device for the purposes of detecting particles. However, wide field of view lenses may produce sufficient distortion that a particle detection system may not operate correctly without some measures being taken to combat the distortion.

Dealing with Lens Distortion

If no attempts are made to correct lens distortion in a particle detection system that uses emitted radiation and image detection in accordance with the present invention, the following effects may occur.

1. Integration Region. The integration region may not properly coincide with the actual position of the beam in the image, since the beam is assumed to be straight, but may actually appear curved.

2. Spatial Accuracy: The computed position in space that corresponds to a particular pixel may be in error.

3. Gain Error: The length of beam that corresponds to a particular pixel may be in error, resulting in a system gain error.

In accordance with a preferred form of the invention, the following techniques may be used to combat some or all of the above effects.

Low Distortion Lens

For a given field of view, a compound lens design can be optimised to give less distortion. With suitable lenses, systems requiring only a narrow field of view may not need any corrections for lens distortion.

Empirical Spatial Calibration

An empirical calibration of the relationship between points in the image and points in space can be performed. This can be done by placing an object that causes some scattering in the beam, and then recording the position of the object in space and also the position as it appears in the image. This process is then repeated for a number of points along the beam.

This empirical calibration can be performed with a device described elsewhere herein as a "commissioning device". Such a device will probably be necessary for the purpose of testing installed systems for correct alignment. In its simplest form it would comprise of a piece of material that scatters some part of the impinging radiation (such as a piece of transparent plastic or glass) mounted on a stick to allow it to be easily place in the beam by an operator or installer.

The minimum number of points required will depend on the degree of distortion and the type of interpolation subsequently used. Points at or near each end of the active portion of the beam should ideally be included. An option is to record a point at the boundary of each intended sector. Each sector may behave as a separate "virtual" detector, with its own alarm logic etc.

The recorded data may then be used in the following ways.

1. The integration area is chosen to include the recorded points. Interpolation or curve fitting is used to estimate the required integration area between the points. The integration area is made sufficiently wide at each point to allow for the beam divergence and any uncertainty in the position of the two points.

2. The recorded points can be used as a lookup table to determine the actual spatial position corresponding to a given pixel or group of pixels. Interpolation is used to estimate values that fall in between the recorded points, or alternatively if the recorded points are the boundaries of each sector, then it is sufficient to use this data to determine which sector each pixel belongs to for use in subsequent received scattered light integration operations.

These methods may address the first two effects mentioned.

The third effect of gain error can either be ignored, since in many cases it will be a relatively small error, or for example by calibrating the camera with a uniformly illuminated scene. This type of calibration or correction may also be needed to correct for other sources of gain error such as camera vignetting anyway. It is worth noting that this sort of correction will be correct for those parts of the image where the laser beam subtends at least one pixel in width, however where the beam is very narrow the correction may be less accurate because the beam is a line source rather than a surface—which was the basis of the correction.

Laser Beam Orientation

The laser beam and camera can be aligned so that the image of the beam passes near the image centre. Since distortion is mostly radial the result will be that the beam still appears as line. This is a measure that allows the integration area to be calculated in a way from knowledge of only two points along the beam by drawing a straight line between the points, and sufficient width to allow for the beam divergence and any uncertainty in the position of the two points.

Model Based Distortion Correction

Modelling

A mathematical model can be used to represent lens distortion. In most cases a radial distortion model is sufficiently accurate. An example of such a model is $$r' = M(|r|) \sim r$$

where:

r is a vector representing the true position of a pixel, r' is the distorted position of the pixel and M is a scaler magnification factor that is a function of the distance of the pixel from the distortion centre, and constrained such that $M(0)=1$ The vector distances are all measured with respect to a point $P=(P_x,P_y)$ that represents the centre of distortion of the lens system.

The model represents a mapping between the distorted image plane and the undistorted image plane.

Various methods for arriving at the function M for a given lens are discussed in literature that would be available to the person skilled in the art.

One approach is to:

Let $M(r)=1+ar+br^2$ (or use a higher/lower order polynomials for improved/reduced accuracy)

Record an image of a scene composed of a uniform array of black dots on a white background Choose one or more rows of dots Determine the co-ordinates of their apparent centres in the image (which is the distorted image plane).

Use a least squares optimisation to determine the best-fit coefficients a, b, $P_x$ and $P_y$ that make the points fail as nearly as possible to a straight line (or lines if more than one row was chosen) when mapped to the undistorted image plane.

This modelling may be carried out at least for each type of lens that is used in a system according to preferred forms of the invention, or preferably for each individual lens at the time of manufacture of the camera unit. The model coefficients are then stored permanently in an associated processing unit or non-volatile memory physically associated with the camera. Other camera related calibrations could be dealt with similarly, for example fixed pattern noise correction data and pixel-by-pixel sensitivity data can factory measured and stored in the camera unit or associated processor.

Correction

The distortion model can be used in several ways. Conceptually one way is to fully "un-distort" entire images as the first processing step after capturing them from the camera.

One method is to set each pixel value (grey level) in the resulting "un-distorted image" to the value of the nearest corresponding point in the original distorted image, using the known model to convert the coordinates.

Since the pixel coordinates after the mapping into the distorted image plane is often fractional, a more accurate method is to use interpolation to obtain an approximation of the pixel value. Bi-linear interpolation yields good results, but a full sin c(x) interpolation may be more useful.

Correcting the whole image is computationally intensive, so it is advantageous to use methods that avoid correcting the entire image.

The preferred method is to do all of the processing as previously described, and apply corrections at the following points in the processing sequence:

1. When computing the integration area, un-distort the coordinates of known points (e.g. laser source spot, target spot if visible, memorised images points obtained with the commissioning device)

2. Compute a set of pixels within an enclosing polygon that makes allowance for beam divergence and uncertainty in the position of the points (same as would be done if there were no lens distortion).

3. Map the co-ordinates of each of the pixels back to the nearest pixel position in the distorted image plane.

4. Repeat above steps for the background cancellation areas

5. All coordinates used in computing the "pixel radius" (distance of a pixel from the apparent position of source in image) should be first mapped to the undistorted image plane.

6. Similarly, coordinates used in computing all geometry related quantities (scatter angles, corresponding position on laser beam etc) should first be mapped to the undistorted image plane.

In this way the integration area takes correct account of the lens distortion, and appropriate corrections are also made for scattering angles and also spatial positions of particles, without the very computationally intensive process of fully correcting entire images.

Note that it may still be desirable for the system of the present invention to be able to correct entire images on occasion for:

1. Visual verification of the distortion model,
2. Delivery of surveillance images to external systems.

In another preferred aspect the present invention provides an apparatus and method of detecting particles comprising emitting a beam of radiation into a monitored region and detecting a variation in images of the region indicating the presence of the particles further comprising means for providing a weighting function to detected images for selectively resolving image portions.

The resolution of the camera limits the resolution or accuracy of the measured position of detected particles. In a system using forward scatter geometry, the position of particles in the beam that are near the camera may be resolved to a high accuracy, however for particles that are more distant the resolution becomes increasingly worse.

Figure 20:
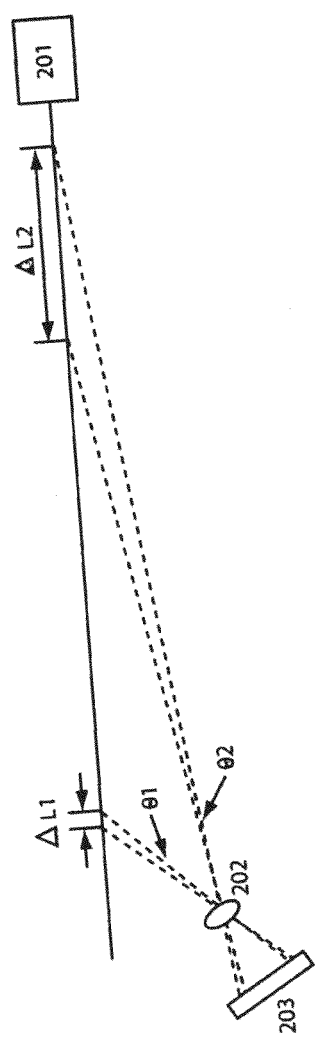
FIG. 20 is an illustration of an optical arrangement in accordance with another preferred embodiment of the present invention.

In FIG. 20, source 201 directs a beam of light in the direction of the camera a camera composed of lens 202 and photosensitive surface 203 such that forward scatter from particles in the beam can enter the camera. The fields of view of two camera pixels are represented by the angles θ1 and θ2. These angles approximately are the same for ordinary lenses. The portions of the beam that are visible in the fields of view of the two pixels are represented by ΔL1 and ΔL1. Even without any calculations it is clear that the length of the beam that corresponds to a single pixel increases dramatically as the distance from the camera is increased. To first approximation, the length ΔL is proportional to the square of the distance of the beam portion to the camera.

In practical terms this means that the minimum required camera resolution for a system is set by the desired performance for determining the position of particles at the far end of the beam. As a consequence there may be far better performance than is needed at the near end.

A lower resolution camera may be used to achieve a given system performance by using a lens system that caused the pixel fields of view to be wider for the pixels viewing nearby parts of the beam, and narrower for those viewing distant parts. Note that when deliberately distorting optics is used, image-processing corrections as described elsewhere herein will generally need to be applied to maintain the correct system operation. The deliberately distorted optics described here cannot be modelled using a simple radial distortion model as is often done for ordinary lenses, however apart from determining the correct distortion model to use, the processing that deals with lens distortion can be the same as that described hereinabove on lens distortion. A compound model may be used, in this case a combination of a radial distortion model and a prism model may be used.

Offset Lens

Figure 21:
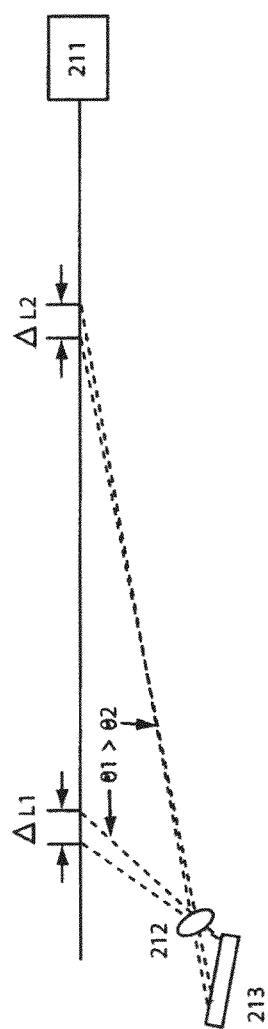
FIG. 21 is an illustration of an optical arrangement in accordance with another preferred embodiment of the present invention.

One technique is known as an offset lens. In FIG. 21, a camera composed of lens 212 and photosensitive surface 213 senses scattered light originating from light source 211. The lens is offset from the centre of the photosensitive surface, and may possibly be also tilted to reduce aberration in the image. The photosensitive surface is arranged to be approximately parallel to the light beam.

Prism

Figure 22:
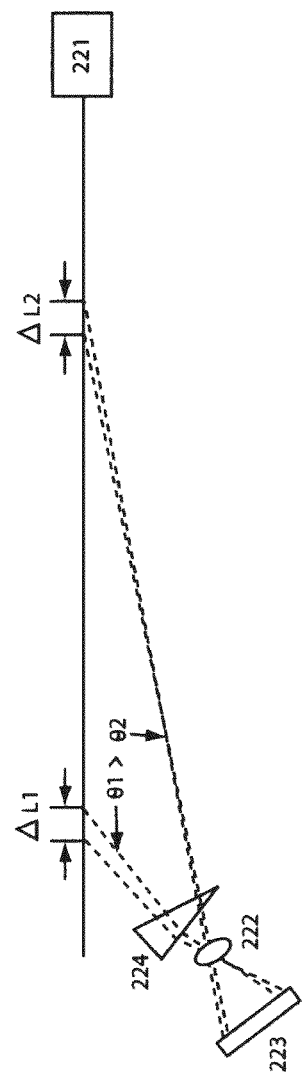
FIG. 22 is an illustration of an optical arrangement in accordance with another preferred embodiment of the present invention.

Another way to achieve a similar effect is to use a prism. An example is shown in FIG. 22 where a camera composed of lens 222 and photosensitive surface 223 senses scattered light originating from light source 221. The scattered light passes through prism 4 before entering the lens. The effect of the prism is to expand or compress the angular subtense of lengths of the beam in a manner that varies depending on the angle of entry to the prism. Prisms with curved surfaces can be also be used to obtain more exaggerated effects than flat-sided prisms. Multiple prisms can also be used to increase the effect.

Curved Mirror

Figure 23:
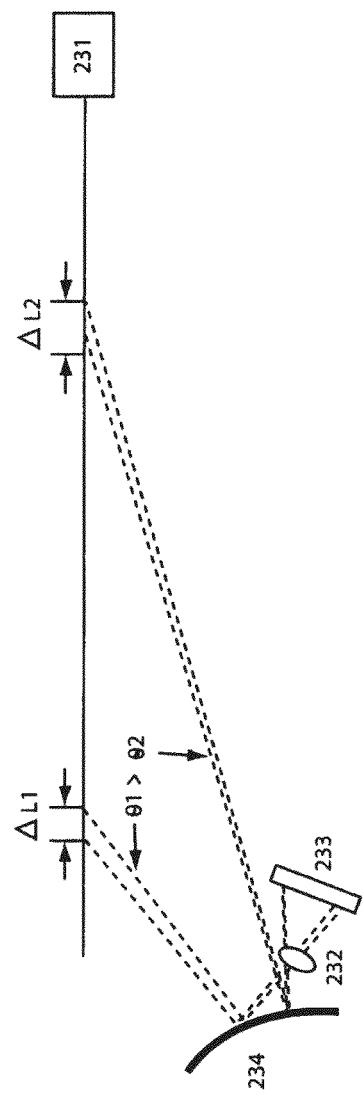
FIG. 23 is an illustration of an optical arrangement in accordance with another preferred embodiment of the present invention.

A further method uses a curved mirror. An example is shown in FIG. 23 where a camera composed of lens 232 and photosensitive surface 233 senses scattered light originating from light source 231. The scattered light is first reflected by curved mirror 234 before entering the lens. The effect of the curved mirror is to expand or compress the angular subtense of lengths of the beam in a manner that varies depending on the angle of incidence to the mirror. Although a convex mirror is shown, concave mirrors or mirrors with convex and concave parts may be used. Generally the mirror would be singly curved, although a doubly curved mirror can also be used.

In another preferred aspect the present invention provides an apparatus and method of detecting particles comprising emitting a plurality of beams of radiation into a monitored region and detecting a variation in images of the region indicating the presence of the particles wherein the beams are adapted to be sequenced in operation.

In a preferred form, the present invention may be made to cover a larger area by adding extra laser beams. If all the beams and the camera lie approximately in a plane, then the beams will approximately overlap from the perspective of the camera. This may result in both a system sensitivity improvement as well as an increase in the area covered by the one camera. The multiple lasers provide a similar sensitivity improvement as an increase in laser power since the camera & background noise contributions are substantially the same as for one beam.

In some forms, it may not be necessary to isolate the position of the particulate down to a single laser beam. However, if required it is still possible to tell where the particulate is located by cycling the laser beams on and off.

A scheme adapted to provide this result would have all the lasers operating one frame on and one frame off as would be done with a single laser. When particulate is detected, the system can then switch to a scanning mode where only one beam is on at a time.

A more elaborate scheme that allows a higher average power while "scanning" is as follows: Every second frame has all the lasers off, while in every other frame all but one laser would operate. In each "laser on" frame a different laser is not operated. Any other linearly independent combinations of laser state could be used. Also, varied laser powers can be used rather than completely turning the lasers off. However, the scheme described here is preferred for its simplicity and the high laser duty cycle that is achieved. Note that lower duty cycles may be preferred in some cases to reduce power consumption and increase laser life.

Figure 24:
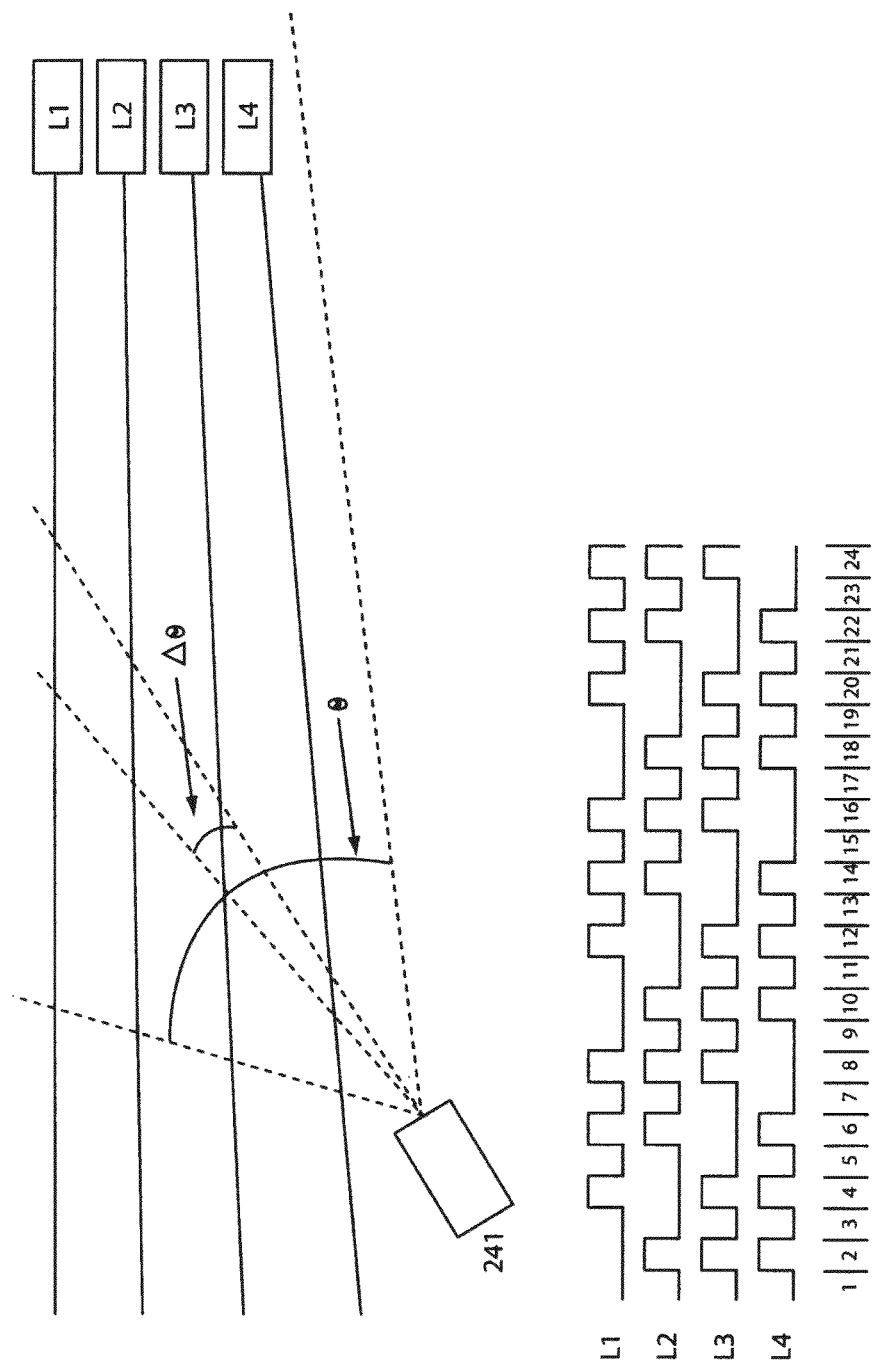
FIG. 24 is a top plan view of another embodiment of the present invention including a timing diagram indication signals in accordance with the operation of a plurality of lasers.

In FIG. 24, camera 241 receives scattered light from laser beams generated by the lasers L1, L2, L3 & L4. The camera field of view is θ. The field of view corresponding to a pixel is Δθ.

The timing diagram of FIG. 24 shows the pattern of operation of the lasers. As noted hereinabove, other patterns can also be used.

The mathematics for converting the camera signals into separate scattering readings for each beam is as follows:

Let:

R be the total received signal at one pixel in the image from the camera, $S_n$ be the contribution from particles illuminated by laser n when laser n is at full power.

$L_n$ be the power of the $n^{th}$ laser where 1 represents full power, and 0 represents a laser off state. (Fractional laser powers $0 < L_n < 1$ also allowed.)

N be the total number of lasers

Then, $$R = \sum_{n=1}^{N} L_n S_n$$

Now if N frames are taken, each with N linearly independent vectors laser states $[L_{11} \ldots L_{1N}] \ldots [L_{N1} \ldots L_{1N}]$ and we assume that the scattering contributions that we seek $[S_{11} \ldots S_{1N}] \ldots [S_{N1} \ldots S_{1N}]$ are constant over the period that the data is collected (i.e. $[S_{m1} \ldots S_{mN}] = [S_1 \ldots S_N]$ for $1 \leq m \leq N$), then the corresponding received signals $R_m$ will be:

$$R_m = \sum_{n=1}^{N} L_{mn} S_n$$

This may be expressed using matrices:

$$\begin{bmatrix} R_1 \\ \vdots \\ \vdots \\ R_N \end{bmatrix} = \begin{bmatrix} L_{11} & \ldots & \ldots & L_{1N} \\ \vdots & \vdots & \vdots & \vdots \\ \vdots & \vdots & \vdots & \vdots \\ L_{N1} & \ldots & \ldots & L_{NN} \end{bmatrix} \bullet \begin{bmatrix} S_1 \\ \vdots \\ \vdots \\ S_N \end{bmatrix}$$

The vector $[S_1 \ldots S_N]$ can be solved for using any of the very well known methods for solving simultaneous equations.

These operations should be done using images that have already had background cancellation performed. Further integration may have been also been performed, or further integration may be performed afterwards.

Also, these operations need to be done for each pixel or group of pixels within the chosen integration area. Subsequent processing is the same as a single laser system, except that N sets of data are processed. The subscript of $S_n$ determines the set to which the particular S value belongs.

A typical system may incorporate laser source spot and target spot monitoring for fault detection and alignment monitoring or feedback. This can still be done even if there is overlap of the spots in the image by using the computations described above on the relevant pixels or groups of pixels, provided that the camera is operating in a sufficiently linear manner, without excessive saturation.

If saturation makes the separation of the contributions from the different laser spots impossible, then an alternative is to occasionally switch only one laser on at a time to confirm the positions of the spots.

In another preferred aspect the present invention provides an apparatus and method of detecting particles comprising emitting a beam of radiation into a monitored region and detecting a variation in images of the region indicating the presence of the particles wherein at least one of a radiation source and a means for detecting the images is adapted to be positioned in a controlled manner.

In a preferred embodiment either one of or, both a light source and a receiver are mounted on position control mechanisms to direct the principal axis of the receiver and light source and their field of view. The advantage of this is that under either manual or automatic control, the system can be made to more closely examine areas of interest in a scene to better supervise critical areas. This may be implemented as a panning or a tilting mechanism or zoom mechanism or any of a combination of the three. For example a panning mechanism allows monitoring of a wide area of interest which may be beyond the field of view of low-cost wide-angle lenses.

Figure 25:
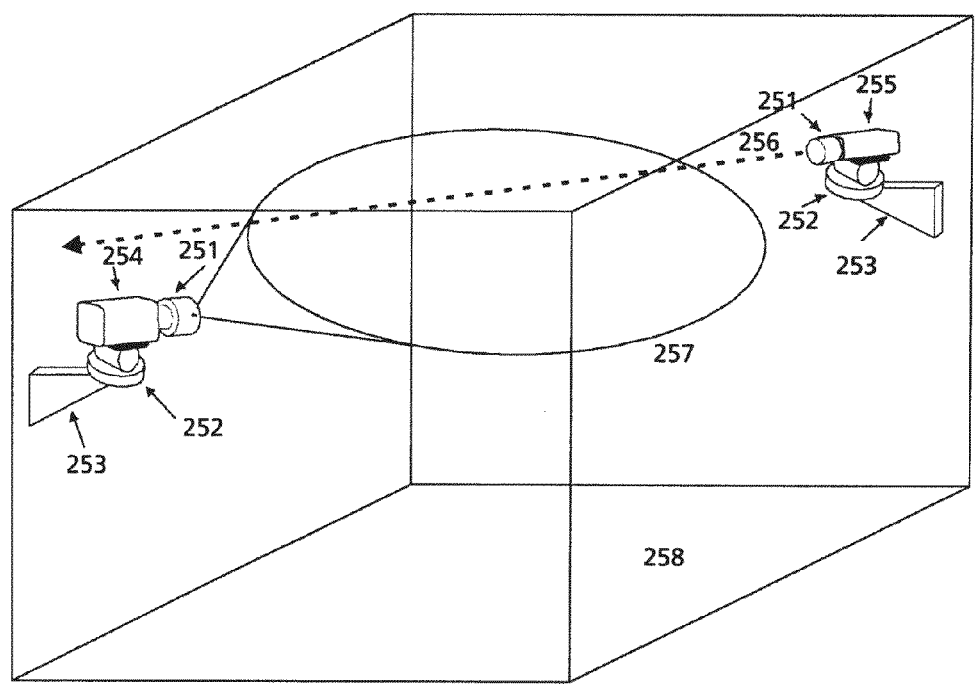
FIG. 25 is a perspective view of another embodiment of the present invention.

FIG. 25 shows an example of a system wherein this pan-tilt-zoom, or PTZ is in operation and set up for normal use. The systems comprises a zoom lens(es) 251, a pan-tilt mechanism(s) 252, mounting brackets 253, receiver(s) 254 (preferably in the form of an image capture device such as a camera), light source(s) 255 (preferably in the form of a laser(s)). Each receiver has a field of view 257 and each source 255 produces a beam 254. The system is used to monitor environment 258.

Figure 26:
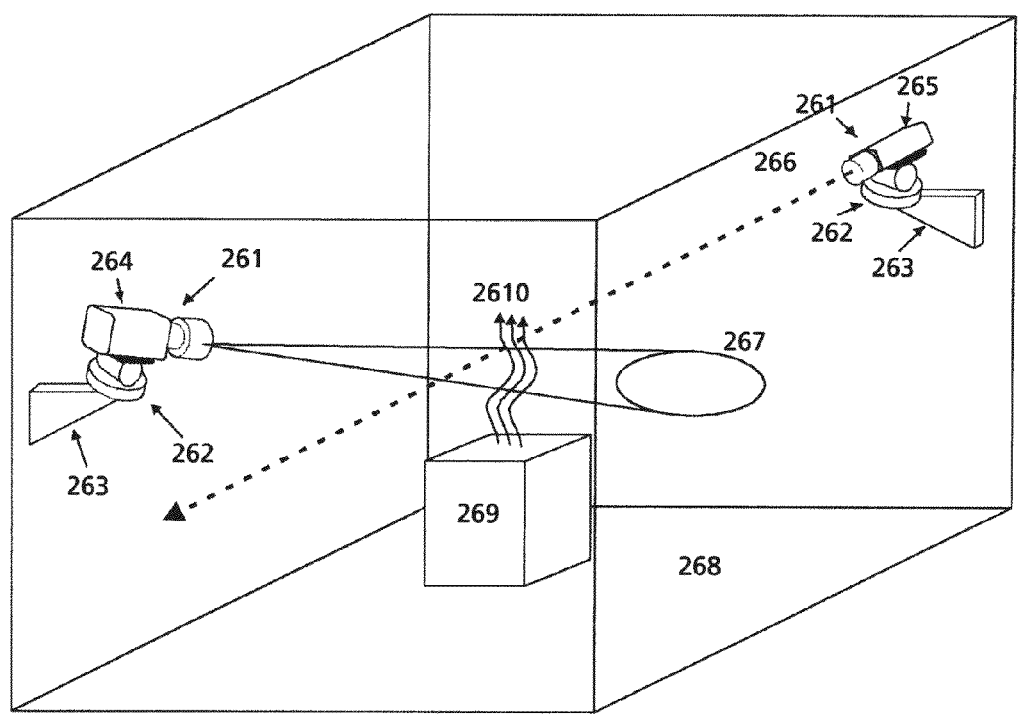
FIG. 26 is a perspective view of another embodiment of the present invention.

FIG. 26 shows the example system of FIG. 25 and how the field of view 267 may be adjusted for close examination of a region of interest, which in this example contains smoke plume 2610.

When the principal axis of either or both of the light source and the receiver is changed, the system calibration is altered and must be accounted for in the measurement process for both the physical location of the region of interest in 3D space as well as the intensity and characteristics of the light scatter measurements. This is readily achieved by either direct calculation or equally by the use of a lookup table.

The PTZ mechanism offers three degrees of freedom for each of the receiver and the light source. There are therefore six degrees of freedom in total which can be expressed as a six-dimensional lookup table. While this is achievable it may be unwieldy in size. For example, allowing for 10 positions in each of the pan, tilt and zoom locations, the possible combinations are 10 to the power 6 or 1 million combinations.

Therefore a preferred implementation can use a table of reduced resolution. For example, for five positions in each of pan tilt and zoom, the combination reduces to 5 to the power 6 or 15,625 possible combinations. If this is insufficient resolution, it is possible to additionally apply interpolation to determine values of position that lie in intermediate points.

Space Calibration

In order to determine the special locations perceived by the system it is necessary to determine the intrinsic and extrinsic parameters of the of the receiver and the light source.

Intrinsic Parameters

In the case where the receiver is a camera using an area array sensor, such as a CCD or CMOS sensor, the important intrinsic parameters are the focal length, x and y pitch of the sensor elements, the coincidence point of the principal axis of the lens and the image array and the radial lens distortion factor. Other parameters such as tilt of the image sensor plane with respect to the lens principal axis and higher order effects such as tangential lens distortion may be accounted for but are generally ignored due to their low significance on measurement results.

Intrinsic parameters may be determined at manufacture and applied in the field.

Extrinsic Parameters

Extrinsic parameters must be calibrated in situ as they depend on the mode of mounting of the light source and receiver. The parameters that need to be measure for full determination of space location are, for each source and receiver, the effective centre of rotation of the source or receiver, X, Y, Z, and the rotation around each of the Cartesian axes, alpha, beta, gamma.

If these are known along with the intrinsic parameters, it is possible for any pixel in the image where the source light beam is visible, to determine within known limits, the X, Y and Z location of the points in space being observed.

In another preferred aspect the present invention provides an apparatus and method of detecting particles comprising emitting a beam of radiation into a monitored region and detecting a variation in images of the region indicating the presence of the particles wherein the images are detected by image detectors located in at least two positions.

Figure 27:
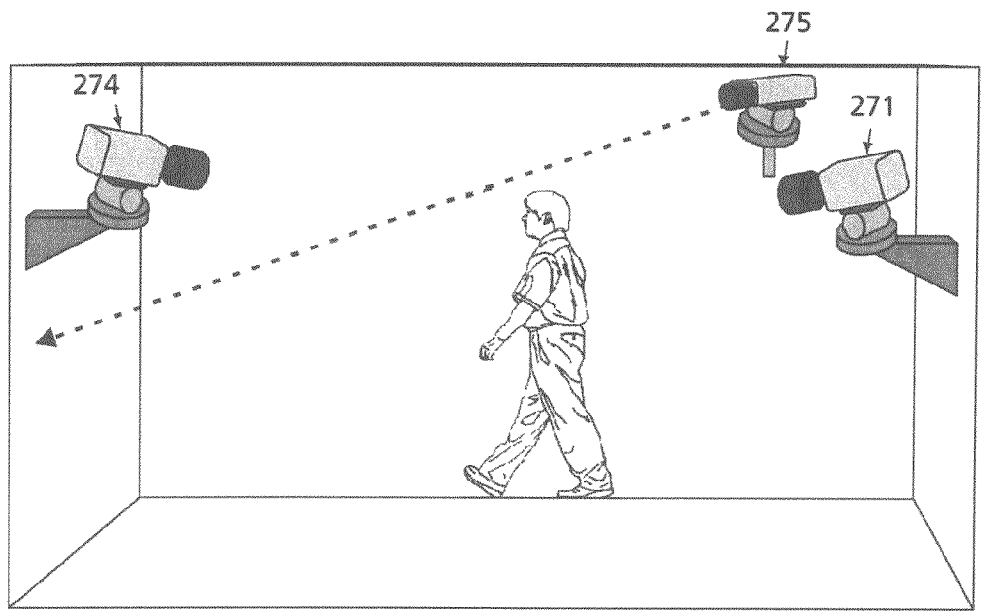
FIG. 27 is a perspective view of another embodiment of the present invention.
Figure 28:
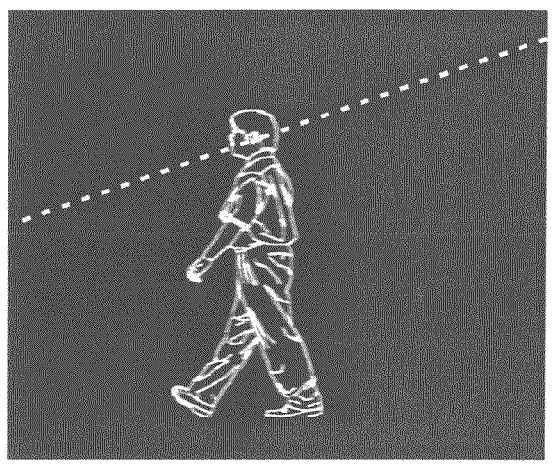
FIG. 28 is an image view taken in accordance with the embodiment of the present invention shown in FIG. 27.

A problem, which may arise in practice, is that the system may misinterpret images and produce an erroneous particle measurement. An example is shown in FIG. 27 in which the monitored environment is indicated by 278. The moving person shown in FIG. 27 may produce image artefacts that may effect the scatter measurements. Receiver 271 views both the scatter from the beam and the person walking in the background. Although image subtraction will reduce the effects of such interference, the resultant image will appear as shown in FIG. 28. In the image of FIG. 28, there are intensity changes in the area of the expected beam location. This may interfere with the measurements at that point and may lead to false alarms.

Figure 29:
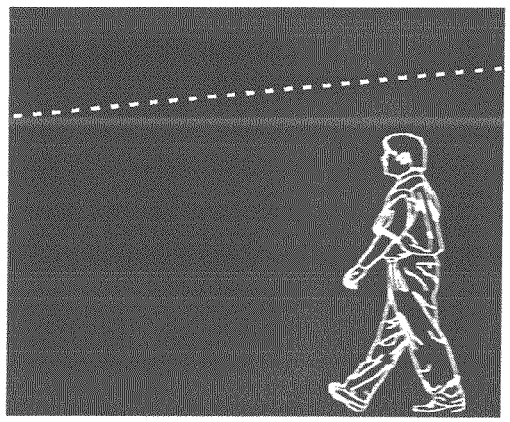
FIG. 29 is another image view taken in accordance with the embodiment of the present invention shown in FIG. 27.

A second camera viewing the same scene but from a different vantage point as shown in FIG. 29, may be used to verify an alarm and to discard interference of the type described above. The interference visible in the second image is clearly not coincident with the expected beam location. Since the system does not perceive scatter activity along the line in both images, then it may discard the false information from the first camera 271 thus avoiding a false alarm.

Figure 30:
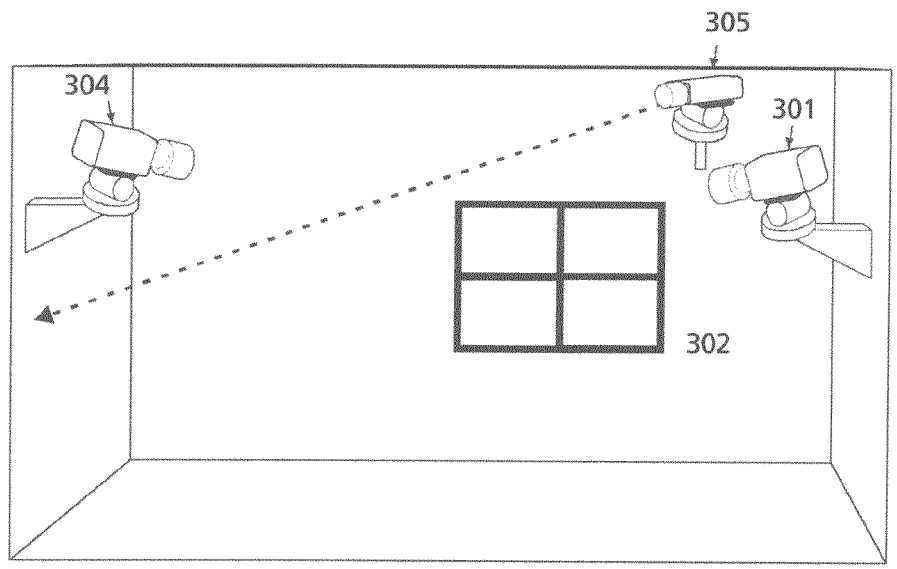
FIG. 30 is a perspective side view of another embodiment of the present invention.
Figure 31:
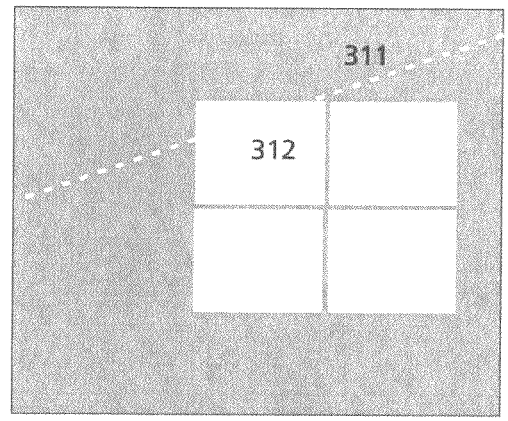
FIG. 31 is an image view taken in accordance with the embodiment of the present invention shown in FIG. 30.
Figure 32:
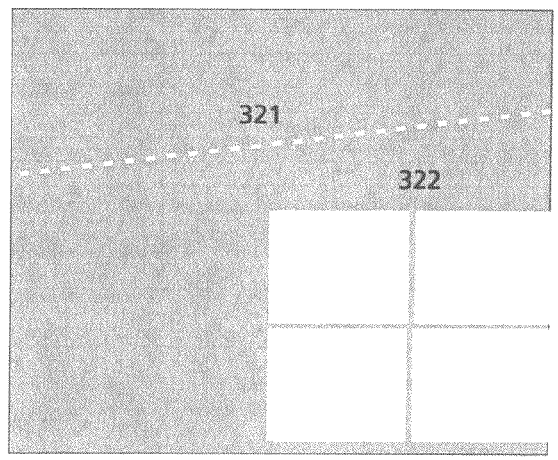
FIG. 32 is another image view taken in accordance with the embodiment of the present invention shown in FIG. 30.

A further problem is that it is possible for a bright background to overwhelm the light scatter from a smoke event causing it to be missed. FIG. 30 illustrates this situation in which environment 308 is monitored. Prior to any processing that may occur, camera 301 is blinded by the bright light from the window 302 along part of the beam path rendering it to be ineffective at picking up scatter over that region. The raw image from camera 301 prior to any processing would appear as shown in FIG. 31. In this image, where the beam 311 passes the window pane 312 the receiver is saturated and therefore unable to detect any additional light scatter which might be caused by smoke particles coincident with the beam at a location where it falls across window pane 312 in the image. The second camera viewing the same scene but from a different vantage point may be used to cover the area missed by the first camera. For example, the second camera image will consist of the image as shown in FIG. 32. In this image the beam path 321 does not overlap the window image 322 so the camera is able to pick up smoke particle events along the length of the beam 321.

As discussed hereinabove, in order to minimise interference effects due to, for example, local changes in lighting conditions, it is desirable to confine the image processing to the region in an image known to be occupied by the light source beam and the region nearby. This also has the advantage of reducing the computational burden on the processing means. It is possible, according a preferred embodiment of the invention, to calibrate the receiver and light source in such a way that, the image region where the beam is visible is known. An alternative approach is to explicitly determine the position of the beam by knowing two points in the beam path. One point can be the light source itself while the other may be a reflective or translucent target or probe disposed in such a manner that it intercepts the path of the beam in space while remaining in the field of view of the receiver. An example of this is shown in FIG. 33 where region 338 is monitored.

Figure 33:
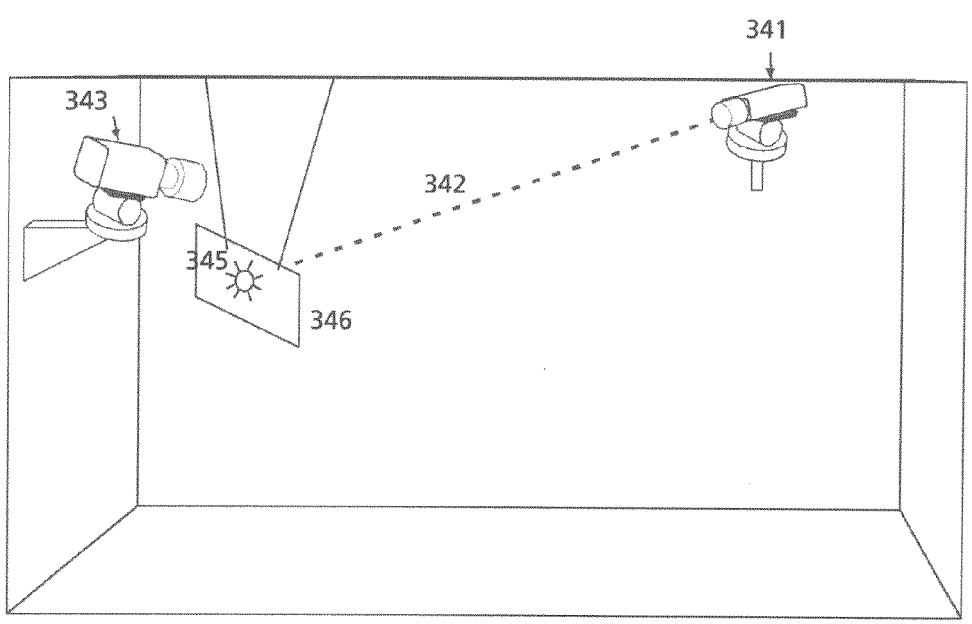
FIG. 33 is a perspective side view of another embodiment of the present invention.
Figure 34:
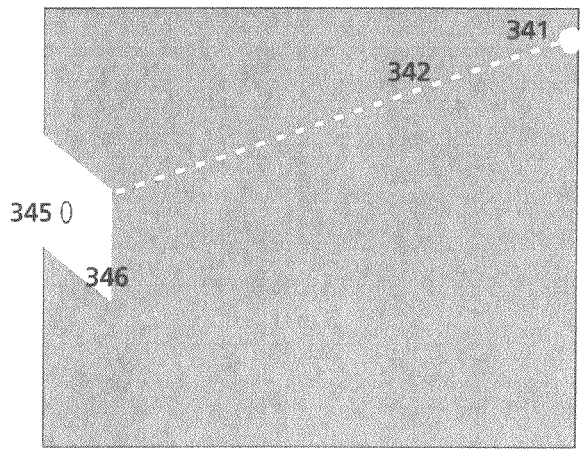
FIG. 34 is an image view taken in accordance with the embodiment of the present invention shown in FIG. 33.

The image captured by receiver 343 of FIG. 33 is shown in FIG. 34. A probe 346 essentially the equivalent of a scattering feature such as a sheet of plastic or glass with suitable scattering characteristics is interposed in the light beam path 342 in such a way that the beam scatter from the projected light spot 345 is visible to the receiver 343. The light source aperture 341 is also visible within the image. Note that the light from light source 341 may be either glare resulting from scatter at the exit pupil of the light source or by a specifically placed light source, such as an LED. It should also be noted that the means of suspension of the scattering means (probe) is unimportant as long as the projected spot 345 remains in the field of view of the camera 343 at all times. Further it should be noted that the projected spot 345 may be used to supervise the beam path 342 since the absence or diminishing of the intensity of the spot 345 may indicate the presence of an obstruction, which in turn may reduce the detection performance of the system.

Where an LED is used as the light source marker, a further feature is that the LED may be flashed on and off in a manner that allows detection of it in conditions of high ambient light For example, subtraction of an "OFF" image from an "ON" image, in whole or in the part of the image containing the LED, will improve the detection of the LED. By determining the source and destination of the light beam and respectively, the area of interest in the image is easily found by linear interpolation. In the case where the receiver lens suffers extreme lens distortion, most commonly radial lens distortion, the interpolation used must be of a higher (general second) order rather than being based on a straight line. Radial distortion can be either of barrel distortion of pincushion distortion as noted hereinabove. In either case, a measure of this value as well as other intrinsic parameters may be required in order to properly determine the path of the beam through the image.

The correction applied for radial lens distortion is of the form:

$$r' = r + nr^2$$

where r' is the corrected radius, r is the observed radius from the projection of the principal point in the uncorrected image and n is a constant found by experiment. In the case of barrel distortion, n is a negative constant. In the case of pincushion distortion, n is a positive constant. Such correction methods would be well known to those skilled in the art of image processing and image acquisition.

Figure 35:
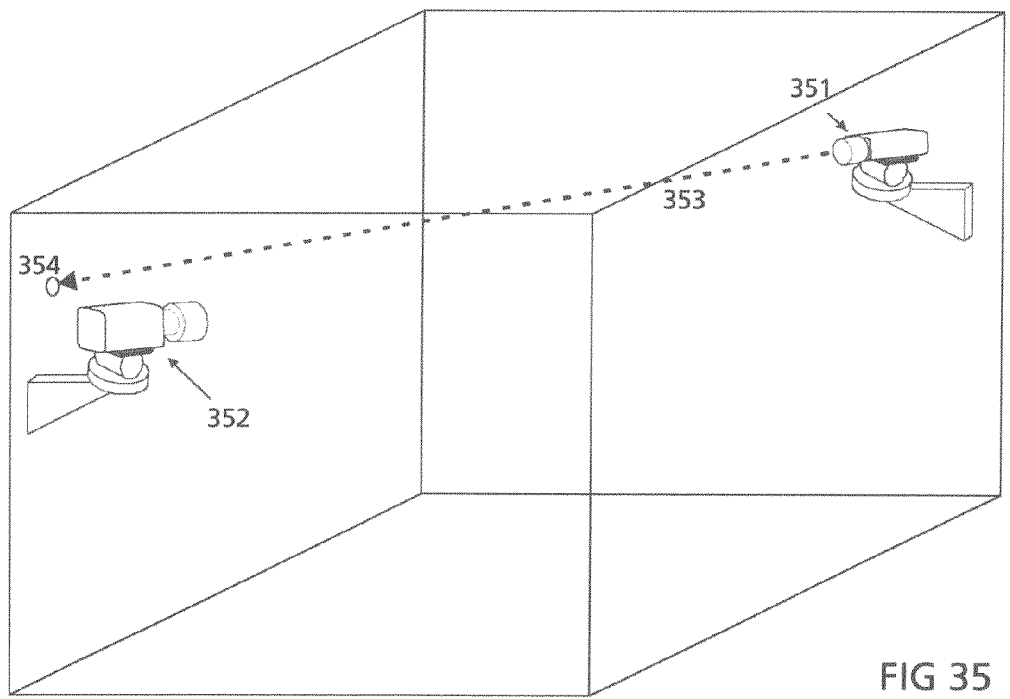
FIG. 35 is a perspective side view of another embodiment of the present invention.

It may be necessary to monitor the direction of the light source beam relative to the receiver in order to be able to calculate the level of smoke based on received illumination. It is also desirable to monitor the light beam arrival to ensure that it is not obstructed. A means of supervising the light beam, in one embodiment is to observe its projection on a surface near the receiver. This was discussed hereinabove and is further elaborated here through the example of an alternative embodiment, illustrated in FIG. 35.

Light source 351 projects a beam of light 353 to an area in proximity to, but not directly at, the receiver 352. The projected light spot 354 on the wall adjacent to the receiver is not visible to the receiver 352. In the above configuration, therefore, the receiver 352 cannot be used to verify that the light beam is unobstructed. There are a number of ways in which the arrival of the beam may be supervised.

Figure 36:
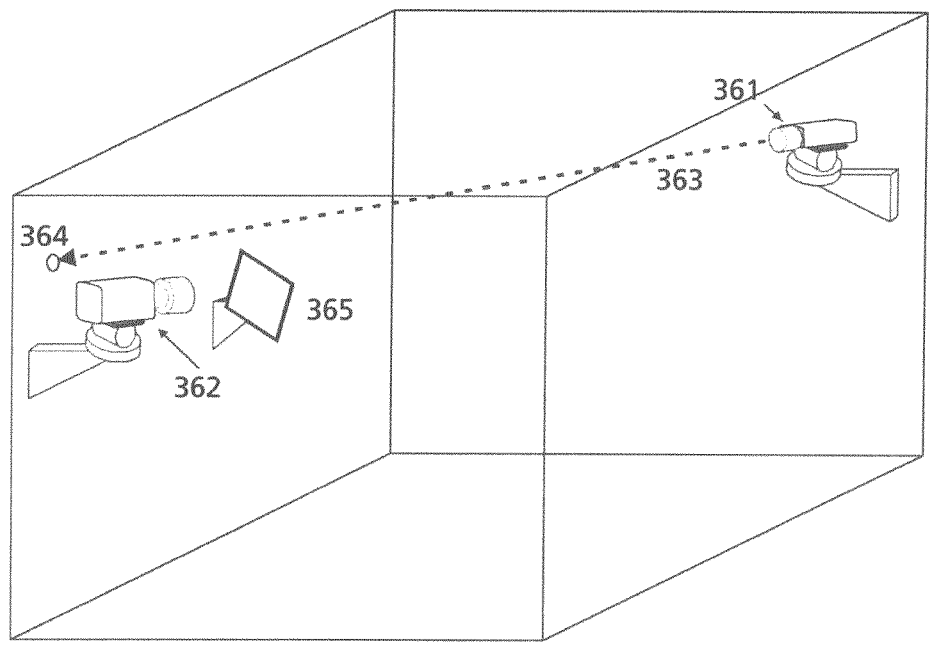
FIG. 36 is a perspective side view of another embodiment of the present invention.
Figure 37:
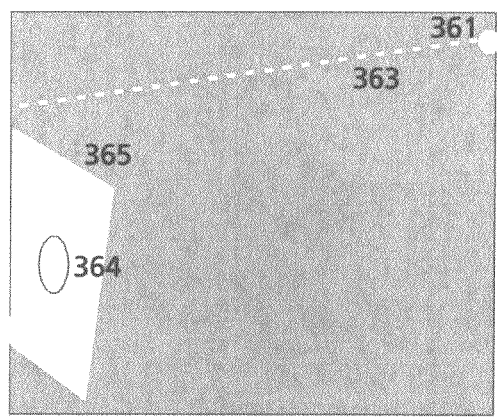
FIG. 37 is an image view taken in accordance with the embodiment of the present invention shown in FIG. 36.
Figure 38:
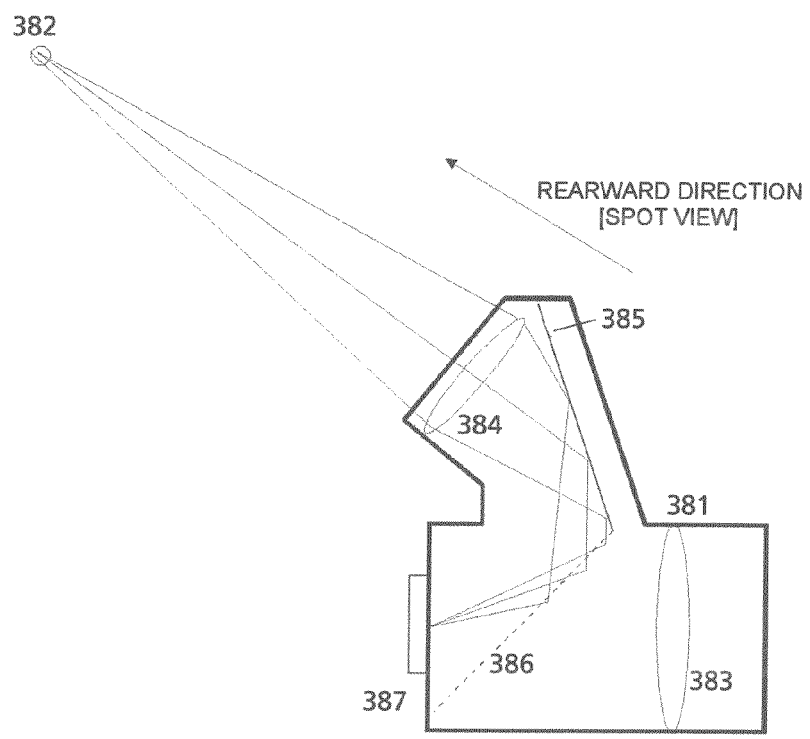
FIG. 38 shows an optical element in accordance with a further embodiment of the present invention.

One embodiment is shown in FIG. 36 where, a rear-view mirror 365 is placed forward of the receiver 362 such that part of its field of view is diverted to be rearward-looking. As before, the light beam projection spot 364 falls to the rear of the receiver 362 but the mirror 365 reflects its image to the receiver 362 so that it is visible. The image captured by the receiver 362 is shown in FIG. 37. The reflection of the projected spot 364 is visible in the mirror 365 as is the light source 361. In an alternate embodiment, the spot 364 may be supervised using a specially designed optical element such as a lens capable of observing the spot image as well as the main forward image. Such a lens is shown FIG. 38. In FIG. 38, the lens housing 381 contains a forward-looking lens 383 and a rearward-looking lens 384. Light, which enters through the forward lens 383, passes through beam splitter 386 and falls upon the image sensor 387. Light entering through rearward-looking lens 384 is reflected by mirror 385 and partially reflected by beam splitter 386 and falls upon image sensor 387. The result is a combined image showing both the spot on the wall to the rear of the receiver and the scene in the forward direction. The beam splitter 386 may take any of a number of well-known forms, such as a prism, but is preferably a section of parallel sided glass. Such glass may be partially silvered if required to better capture light from lens 384 but this is not necessary.

A disadvantage of the above method is that the combination of the two images may cause some interference reducing the sensitivity of the receiver to light scatter in the main direction of view.

Figure 39:
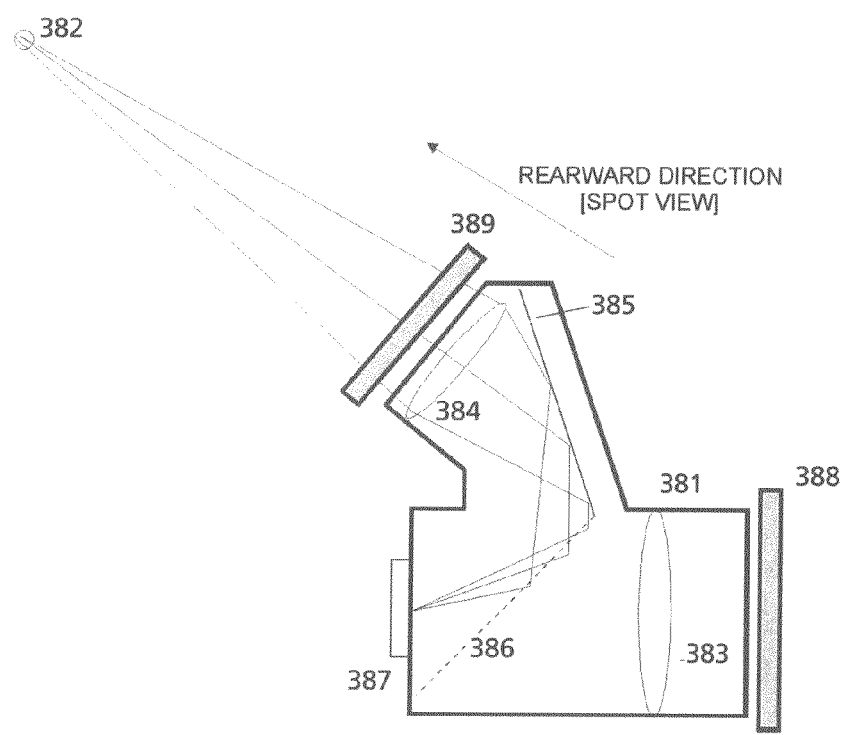
FIG. 39 shows an optical element in accordance with another embodiment of the present invention.

An improvement therefore, is to apply a shutter to either or both the rearward and forward looking apertures do that they may be observed by the same receiver in alternation. An example of this is shown in FIG. 39. The addition of shutters 388 and 389 allows independent viewing of the forward and the rearward scenes. The shutters may be operated mechanically using motors or other physical actuation means, or may be solid state shutters, having no moving parts, such as a Liquid Crystal shutter or Magneto-Optical shutter.

In an alternative embodiment of this principle, the forward-looking shutter 388 may be omitted. When it is desired to observe spot 382 through rearward looking lens 384, shutter 389 is opened allowing light from the spot to fall on the image sensor. Usually the spot will be far more intense than any feature in the forward looking scene and is easy to discriminate.

Figure 40:
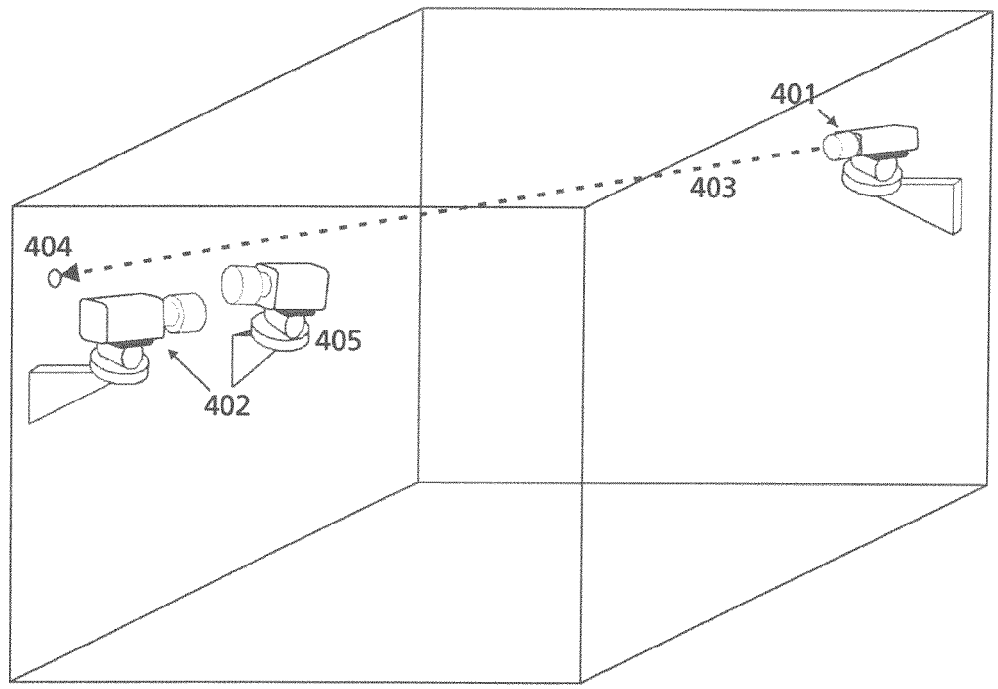
FIG. 40 is beam supervision arrangement in accordance with another embodiment of the present invention.

In yet another embodiment, the beam may be supervised using an active image capture system. For example, a dedicated camera may be used for the sole purpose of determining the position and intensity of the projected spot. This is shown in FIG. 40. Receiver 405 monitors the position and intensity of the projected spot 404. In one such embodiment, the rearward-looking receiver 405 may be camera, such as a CCD or CMOS array camera or equivalent. In another embodiment of this principle, the receiver may be a Position Sensitive Diode (PSD) where the output signal derives from the intensity and position of the spot projected on its surface. In yet another embodiment of this principle, the receiver 405 may be a single photodiode aligned to observe the reflected spot and to provide a signal based on the spot's intensity. The absence or attenuation of the spot giving rise to an alarm signal through the aid of a simple processing means.

In yet another embodiment, the receiver 405 may be an array of two or more photodiodes, the comparative signals of which may be used to indicate the extent of deviation from of the spot from the desired location.

In any of the above embodiments, the rearward-looking receiver 405 and the forward-looking receiver 402 may be combined into one physical structure for ease of mounting and alignment.

Supervision of Beam by Receiver

Figure 41:
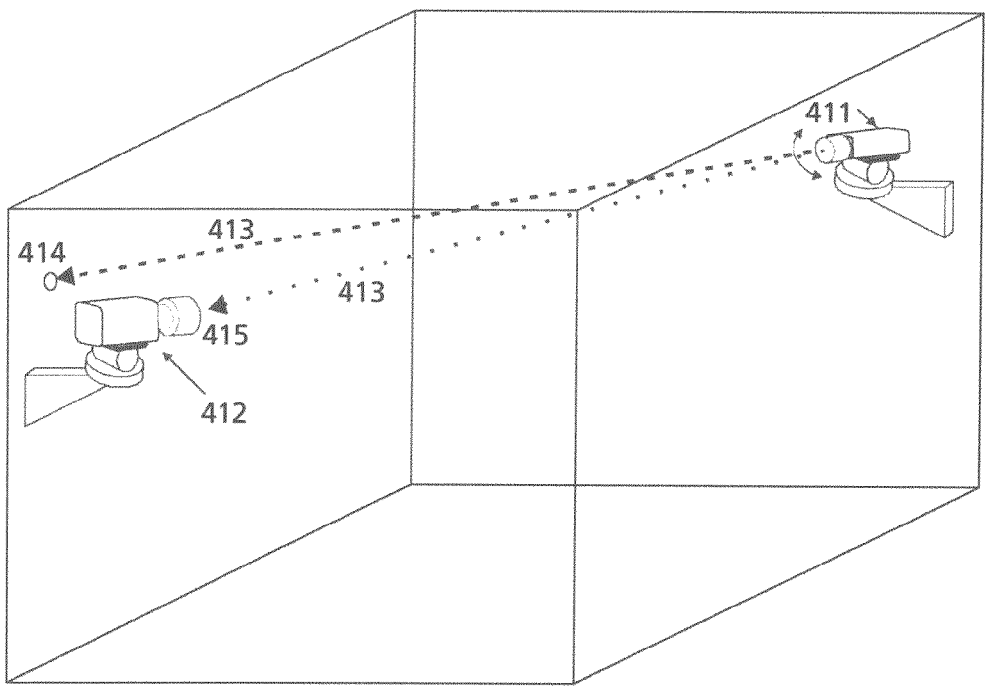
FIG. 41 is a perspective side view of yet a further embodiment of the present invention.

In a further embodiment, the same receiver used for detecting scatter may supervise the beam arrival. This is shown in FIG. 41. In this embodiment of a beam supervisory system, the beam 413 is periodically steered to position 415 directly into or near to the lens of the receiver 412. This may cause a very high signal level, which is used to confirm the arrival of the light beam. After confirmation the beam is steered back to its normal position 414. The advantage of this approach is that it reduces cost by eliminating the need for a separate beam supervisory element.

Figure 42:
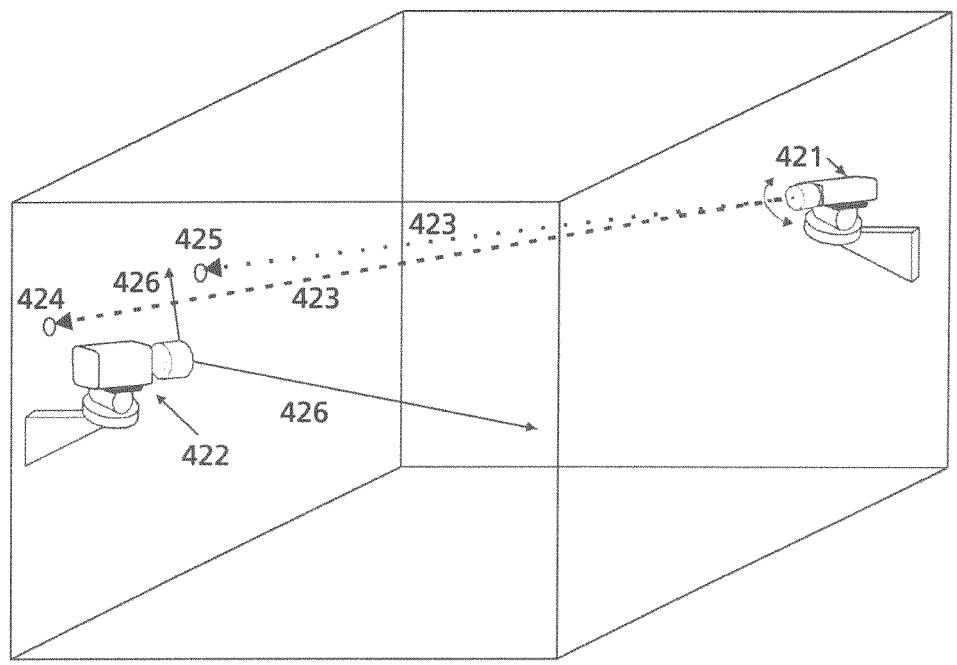
FIG. 42 is a perspective side view of still another embodiment of the present invention.

Yet another means of supervising the arrival of the beam is to periodically direct it to a surface in the field of view of the receiver. In FIG. 42 two lines 426 indicate the limits of the receiver's 422 field of view. In the normal state, the light source 421 directs the beam 423 to a first target position 424. Periodically, the beam is steered to a second target position 425, which is selected so as to be in the field of view of the receiver 422. The projected spot at 425 is detected by the receiver, so confirming the arrival of the beam. The beam is then returned to its normal position 424.

Figure 43:
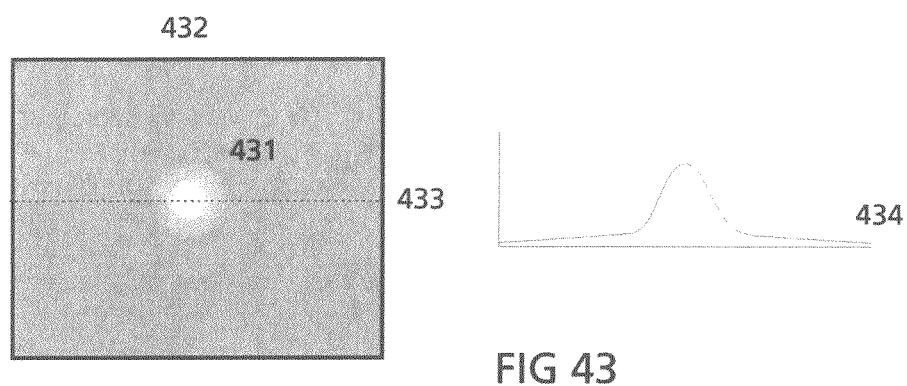
FIGS. 43 and 44 show image and beam profiles for beams used in accordance with embodiments of the present invention.
Figure 44:
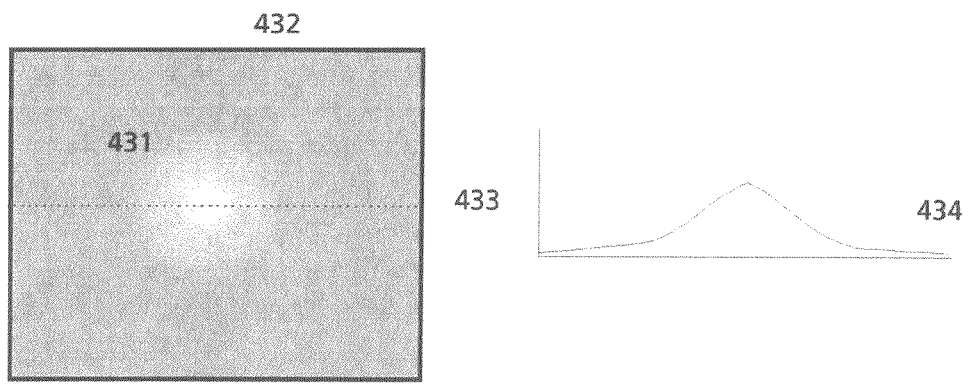

It would be appreciated by those skilled in the art of particle scatter measurement, that a beam of light passing through a cloud of particles is scattered in a manner depending on the light spectrum and the size distribution and absorption characteristics of the particles as previously discussed hereinabove. The diagram of FIG. 43 shows the image and beam profile for a beam with no interfering particles present. In the diagram, the light spot 431 is present on target 432. A profile of intensity taken, for example, along line 433 is shown as relative intensity on graph 434. Where the beam is substantially monochromatic and the particle distribution single-moded where the mode represents large particles compared with the wavelength of the beam, a pattern of fringes is readily observable. In reality, due to inconsistency in the viewing distance and wide distribution of particle sizes, the fringes merge causing an apparent spreading of the beam. Where the beam spot is observed on a wall or other target, the effect is to increase the intensity of light in the region surrounding the beam and to reduce the intensity of the spot itself, which is shown in FIG. 44. By combining the observed intensity distribution measured above with intensity information derived from receivers placed at a number of angles relative to the beam direction it is possible to form an estimate of the particle size distribution and also to more closely emulate the reading that would be obtained from a standard obscurometer in the same environment.

Suppression Disc

Figure 45:
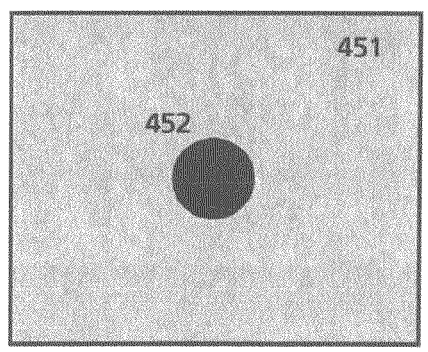
FIG. 45 shows a masking structure in accordance with another embodiment of the present invention.
Figure 46:
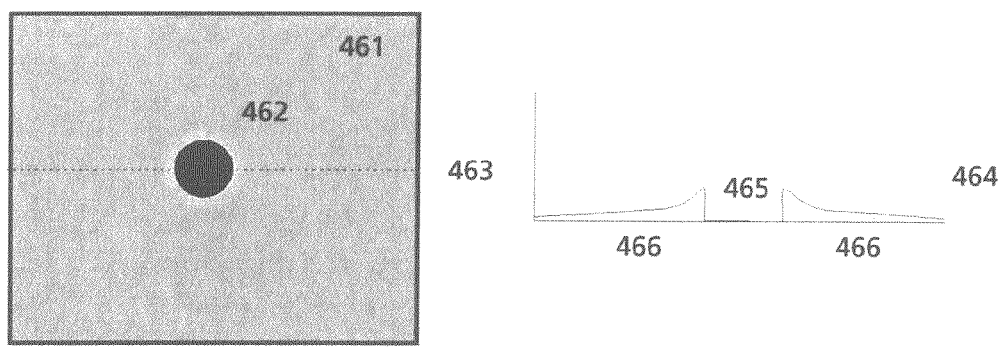
FIG. 46 shows a masking structure in accordance with another embodiment of the present invention and a beam profile in relation to the masking structure.

In order to improve the sensitivity to the beam spreading effect, it is possible to focus the main beam on a light-absorbing structure or surface or masking structure, so as to accentuate the spreading of the beam caused by the scatter of large particles. An example of a suitable target with this characteristic would be as shown in FIG. 45, where 451 is the normal target surface and 452 is a circle of light-absorbing material. Note that equally, 452 may be a cavity structured in such a way as to minimise reflection of light back through the aperture. In FIG. 46, the graph 464 represents the intensity profile observed across line 463. The effect of beam spread is more readily detectable by the receiver due to the suppression 465 of the very bright central spot allowing the detection of the dimmer tails 466.

Test Illuminator to Check Receiver

It may be necessary to ensure that the receiver is operating correctly. Where the receiver is an area array detector, such as a CCD or CMOS camera, defective picture elements (pixels) or excessive dust particles settling on the image array surface may cause the system to miss light scatter events.

In one embodiment, a means of checking the operation of each element is to provide an illumination source to flood the array with light. Each element may be checked against an acceptable standard and a pass/fail assessment made. An improvement to this test is to store a reference image from the receiver with the illuminator active at an early stage of manufacture or installation and use this stored frame for comparison with subsequent illumination test frames eliminating the need to compensate specifically for mirror pixel-to-pixel variations or static spatial variations in illumination during the test.

Figure 47:
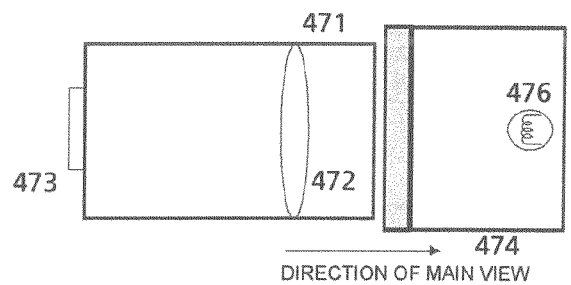
FIGS. 47 and 48 show illuminator means in accordance with respective embodiments of the present invention.

One means of checking the operation of the array is to provide an external light source, which may be periodically disposed in front of the receiver to cast an even glow. In FIG. 47 the illuminator means 474 is temporarily disposed ahead of lens housing 471. Light from an illumination source 476 passes through optional screen 475 which serves to scatter the light from said illumination source which subsequently passes through lens system 472 and on to image sensor 473 where said image sensor is capable of spatially resolving intensity variations over its surface, as for example a CCD or CMOS array. The illuminator means 474 may be implemented in a number of ways using light sources such as electroluminescent panels, LEDs or where there is sufficient environmental illumination, the said means may comprise a simple ground glass screen or equivalent to scatter the illumination already present in the environment surrounding the receiver.

Figure 48:
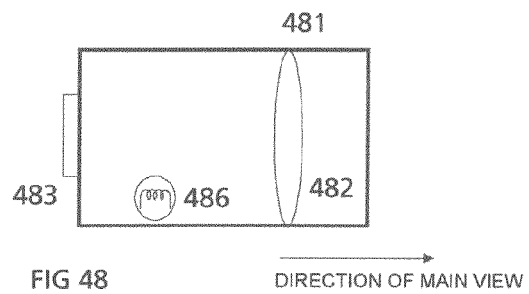

Yet another means of implementing the test illuminator is shown in FIG. 48. In FIG. 48, an illumination source 486 is placed in close proximity to the receiver detector array, in the space between the lens system 482 and the image receiver 483. This illuminator may be activated periodically and the functioning of the image array checked.

Backscatter to Detect Thick Plumes of Smoke

In the event of a sudden thick plume of smoke as may occur in when highly flammable material is ignited, it is possible that the light beam will be so greatly attenuated that the forward scatter will be undetectable. Under these conditions it is possible, according to a further embodiment of the invention, to use the light scattered back toward the source to indicate the location and quantity of smoke in the air as discussed hereinbefore.

Figure 49:
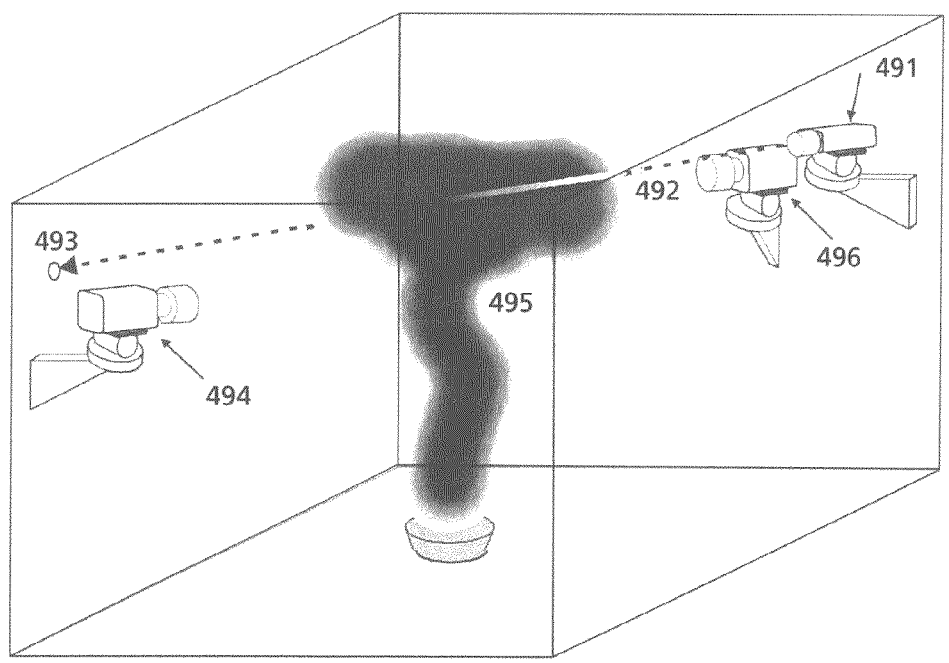
FIGS. 49 and 50 show perspective side views of respective further embodiments of the present invention.

An example of this configuration is shown in FIG. 49. Referring to FIG. 49, a light source 491 projects a beam 492 through space to point 493 located near receiver camera 494. Smoke plume 495 has an optical obscuration so that no significant amount of light from the beam is detectable by the receiver camera 494. However, an additional receiver camera 496 is placed adjacent to light source 491 so as to receive light emanating as backscatter from the dense plume. This allows detection of the plume as smoke and subsequent raising of an alarm.

Figure 50:
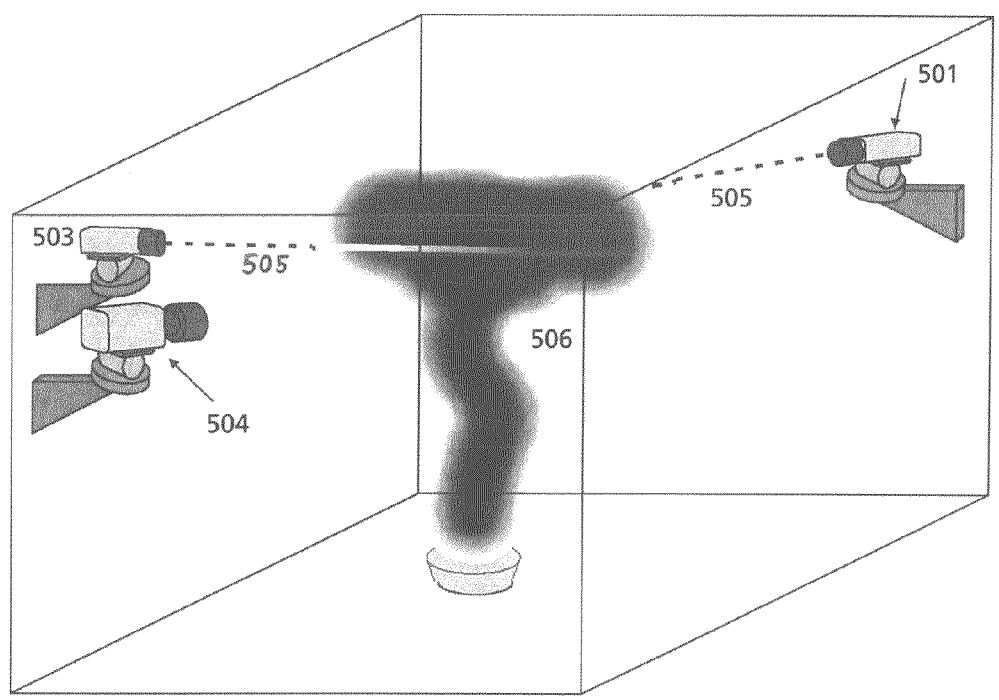

An alternative implementation of the same method is shown in FIG. 50 where, the light beam 502 from source 501 is totally obscured by smoke plume 506. Secondary light source 503 next to receiver 504 is made to project a beam 505, which enters the plume. Backscatter from beam 505 is detected by receiver 504, which is made to raise an alarm.

Figure 51:
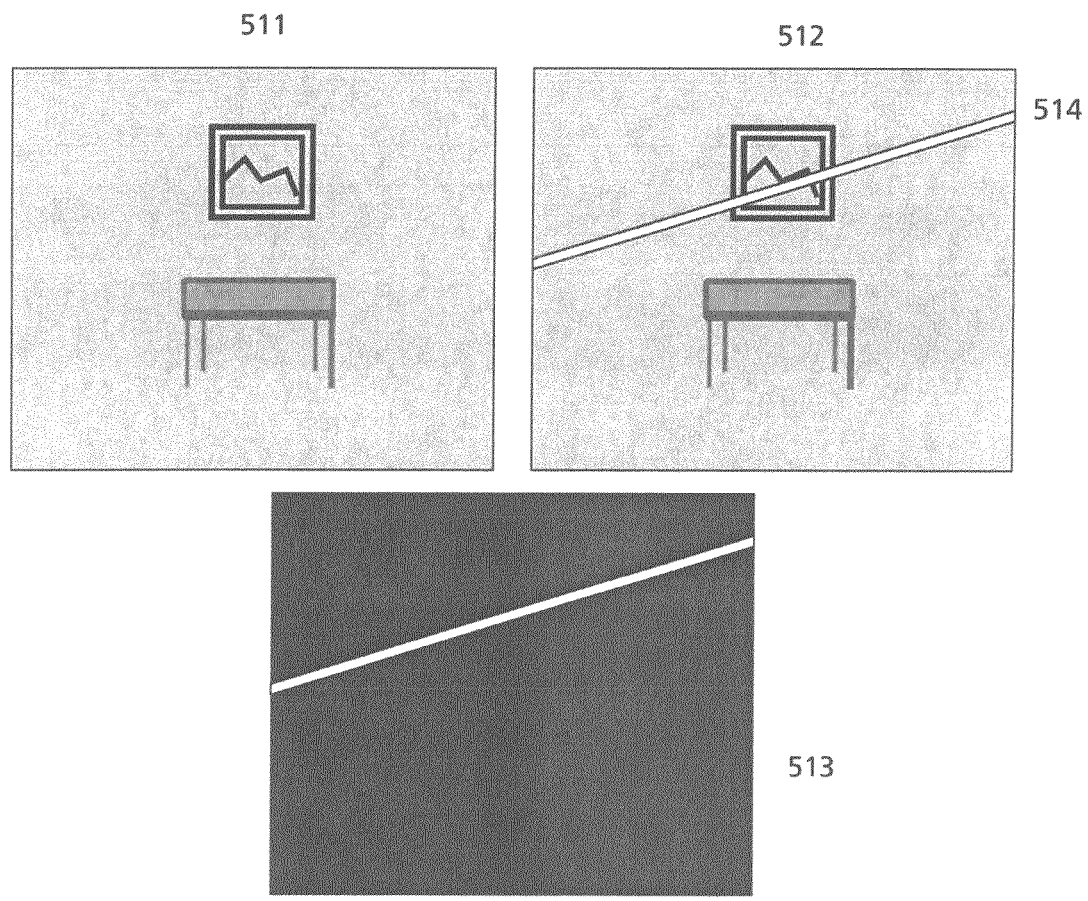
FIGS. 51 and 52 show images taken in accordance with other embodiments of the present invention.
Figure 52:
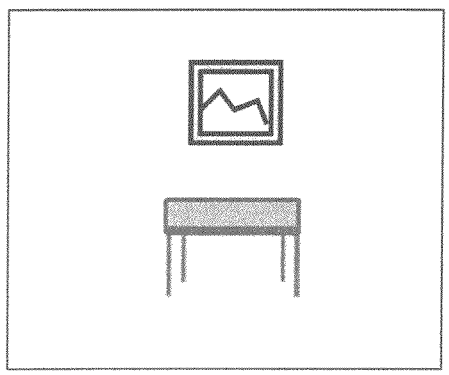
Figure 52:
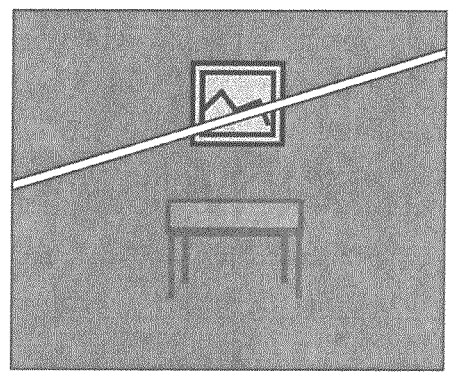
Figure 52:
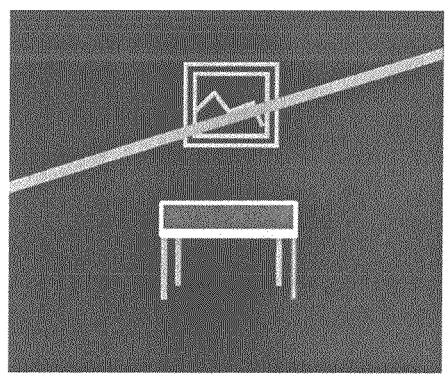

Due to the low levels of scattered light relative to the background in an image, it is necessary to apply algorithms to reduce the effects of image noise thus improving the detection capability of the system. This process may be explained with reference to the FIG. 51. Where no scaling is employed, the first image 511 is captured with the light source off. In the second image 512, the image is captured with the light source 514 on and under identical ambient lighting conditions. The difference image 513 formed by subtracting 511 from 512 shows no background artefacts but allows the light source scatter to be easily detected. The receiving system's sensitivity may ordinarily be adjusted to ensure that the captured images are within its dynamic range. Where interference occurs, the overall background intensity may differ between the laser-on and laser-off images. When the image subtraction is performed, therefore, the background does not cancel out completely and so background artefacts remain in the difference image. In the FIG. 52, image 521 with the light source off has a higher overall intensity due to, for example, fluorescent light flicker. Image 521 with the light source off is subtracted from image 522 with the light source 524 on, revealing resultant image 523. In the resultant image 523 features from the background are not cancelled by the subtraction process. This may lead to erroneous detection events or alternatively may reduce the ability of the system to discern smoke events due to the need to set higher thresholds for detection.

Figure 53:
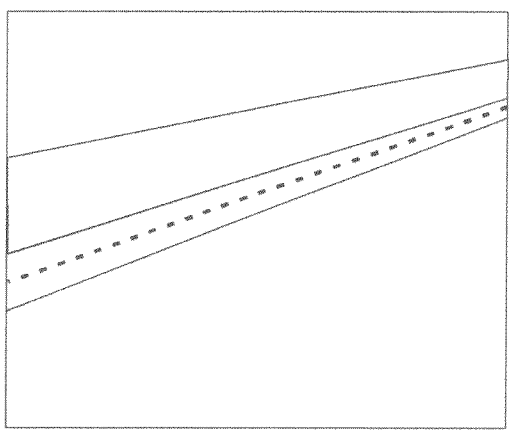
FIGS. 53, 54 and 55 show images of regions of a beam used in accordance with further embodiments of the present invention.

A means of overcoming this is to apply a correction based on the intensity of the images which are known to be equivalent from one image to the next. Comparing the background image (light source is off) with the active image (light source is on) it is clear that there are areas in both images which do not change due to the illumination of the light beam. Therefore, any variation in these areas must be due to interference effects such as fluorescent light flicker. In FIG. 53, the shaded region 531 represents an area known to exclude the area of the beam path 532. Region 531 is called the Background Integration Area, and region 532 is called the Light Beam Integration Area. By evaluating the illumination in 531 in an image it is possible to adjust the whole image so that its intensity is increased or reduced as required to make the reference region 531 have a desired illumination. This may be regarded as a form of automatic gain control. Therefore, when such processed images are used for image subtraction, the resultant image more readily reveals the scatter from the light beam in the area 533.

In an alternate implementation, the images may be adjusted at the time of subtraction without first having to modify the images. This may lead to some economy in arithmetic processing. An example of this is as follows.

Let there be two images, I1 and I2 where I1 is the Image with the light beam off and I2 is the image with the light beam on. Let the reference region of image 531 be R1 and the reference image of I2 be R2. Further, let the average intensity of all of the pixels in R1 be V1 and let the average intensity of all of the pixels in R2 be V2. Then, the difference image $I_{diff}$ may be formed by the calculation $$I_{diff}(x, y) = I_2(x, y) - \frac{V_2 I_1(x, y)}{V_1}$$

for each pixel (x,y)

This step corrects for overall changes in illumination so that the dominant feature in the difference image is the scatter from the light source beam.

A further enhancement of this method is to confine the arithmetic processing to the Light Beam Integration Area. This reduces the computational load permitting a more economical implementation.

Figure 54:
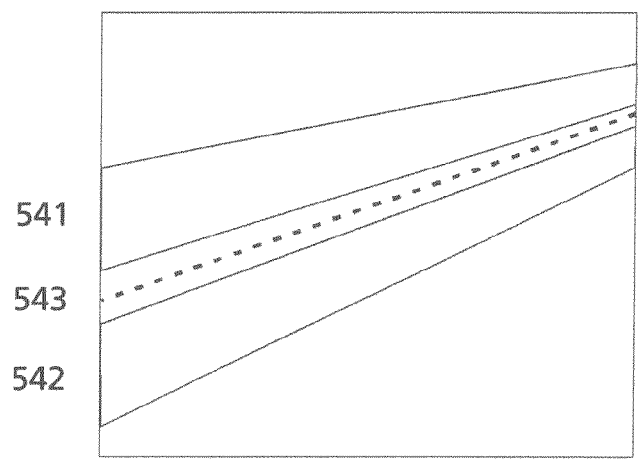

A better measure of variation may be obtained by using reference regions on either side of the light beam position. In FIG. 54, the regions 541 and 542 on either side of the beam region 543 are used to track relative changes between images. Since the detection algorithm preferably compares an image with the beam turned off with an image where the beam is on, this has particular application where there is interference due to external light sources, such interference being unsynchronised with respect to the image capture times. Examples of such interference are fluorescent lights and neon signs. Where these interference sources exist, it is possible to scale images taken with the light source, on and with the light source off, so that subtraction of images will more completely remove image background artefacts.

Where the path of the beam 543 in the detecting image is known, regions 541 and 542 on either side of it may be used as a measure of overall illumination in the image. The correction formula is the same as the correction formula given above.

A further enhancement of this method allows for corrections where the interference is not even over the image area. For example, if there is an interfering light source disposed so as to predominantly illuminate one region of the area being monitored, an overall or global adjustment may not be possible. Therefore, a localised or region-by-region correction is better applied.

Figure 55:
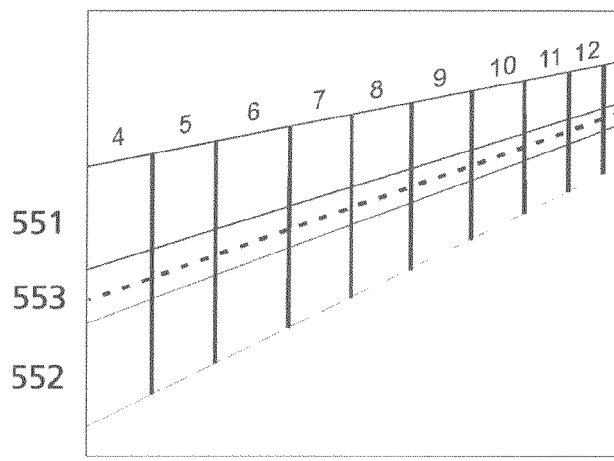

This will be explained with reference to FIG. 55. The images are divided up in to sections above 551 and below 552 the position of the beam 553. Corrections of the type described above are now applied on a region-by-region basis where each region consists of a section of type 551 and a section of type 552 below it. Thus each region [4] to [12] comprises a triplet of a section 551, a section 552 and the region between 551 and 552 where the beam path exists.

The correction formula is then calculated and applied on a region-by-region basis, being applied only to the pixels in the region applicable.

Where ratiometric correction and subsequent background cancellation are applied, there are four elements to the calculation each having an unwanted noise component as well at the wanted signal. The elements are the Light Beam Integration Area with the fight source on, the Light Beam Integration Area with the light source off, the Background Integration Area with the light source on and finally the Background Integration Area with the light source off.

The noise in the system mainly arises from receiver image noise. This may be reduced by capturing and integrating a number of images, by increasing the size of the integration regions or by increasing the duty cycle of the light source on time. These measures may be used individually or in combination to improve the signal with respect to the receiver noise.

In order to achieve optimum noise reduction it is important that the regions selected for calculation are not prone to excessive interference.

Excessive interference could arise from objects in the field of view such as televisions, computer monitors, animated signs and so on. Other objects may also present interference, such as moving machinery, an external window to passing traffic or a walkway in the field of view with regular pedestrian traffic.

During installation or commissioning, it is possible to nominate, manually, areas to exclude from processing. Thereafter the system may ignore data from the excluded regions.

In a preferred implementation, the selection of the excluded regions would be automated removing the need for manual setup of this aspect during installation or commissioning. Each picture element may be characterised by a parameter, which measures its level change over time. Such a measure may be obtained by calculating the standard deviation of the pixel level over a selected period. Where such measure for a given pixel is significantly in excess of the majority of pixels, that pixel would be marked as unsuitable for use in region calculations.

It is desirable to monitor the position of the light beam source in the receiver's field of view in order to be able to be able to predict the beam path in the received image. This may be done as described hereinabove with reference to FIG. 33, where knowing the position of the source beam and at least one other point in the beam path, and area of interest can be identified corresponding to the path of the beam through the image.

Figure 56:
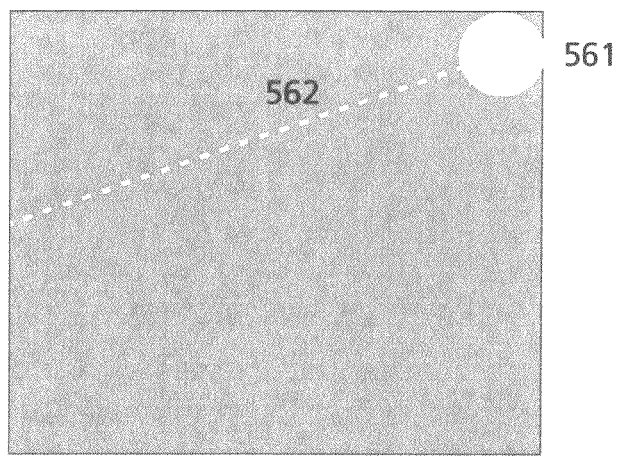
FIG. 56 is an image taken in accordance with another embodiment of the present invention.

A significant problem that arises when viewing the laser source is that the receiver can be overloaded so that the image captured is saturated in the region of the source. The result of this is that the region so effected is not sensitive to scatter information and is therefore unable to detect smoke. In FIG. 56, the light source 561, generating beam 562 overloads a large portion of the received image and this effectively disables smoke detection in that region.

Figure 57:
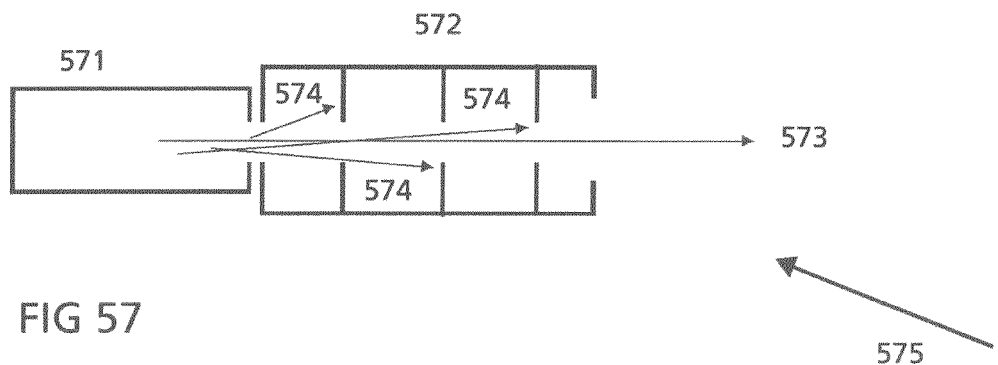
FIGS. 57 and 58 show light source arrangements in accordance with respective further embodiments of the present invention.

The problem can be alleviated by masking the light source in such a way as to shield the receiver from light directly scattered from the source aperture. One method for masking the light source is to apply a series of baffles in line with the light source aperture. With reference to FIG. 57, a system of at least one baffle plate 572 is placed at the aperture of a light beam source 571. The main light beam 573 passes unhindered. Off-axis light scatter 574 is absorbed by the baffle system 572 and is therefore not visible to receiver whose viewing direction is shown by 575.

The use of such a system of baffles greatly reduces or altogether eliminates the image of the light source captured by the receiver.

Figure 58:
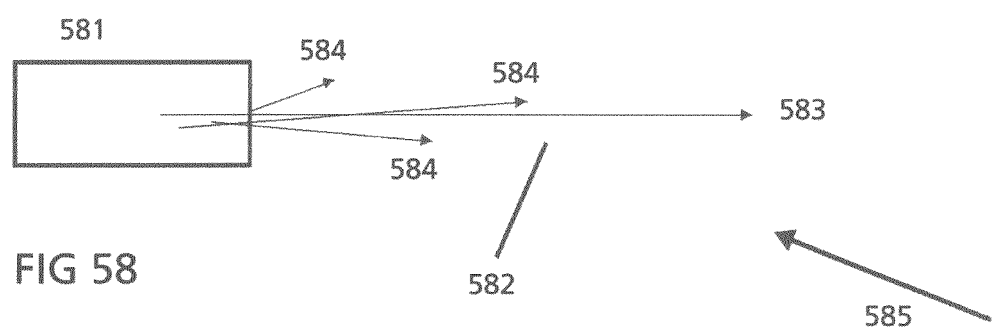

Devices other than a baffle system can be used to achieve an equivalent result. For example a simple opaque or semi-opaque plate can be placed so that it shades the direct view of the light source aperture by the receiver, but does not interfere with the passage of the main beam. This is shown in FIG. 58, where plate 582 intercepts and absorbs and side scatter 534 that would be received along receiver viewing angle 585. The use of a semi-opaque plate has the advantage that the location of the light source can still be identified in the receiver's image due to the light passing through the plate from the light source to the receiver.

While this invention has been described in connection with specific embodiments thereof, it will be understood that it is capable of further modification(s). This application is intended to cover any variations uses or adaptations of the invention following in general, the principles of the invention and comprising such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention as described hereinabove. Therefore, the specific embodiments are to be understood to be illustrative of the many ways in which the principles of the present invention may be practiced. In the description hereinabove, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

"Comprises/comprising" when used in this specification is taken to specify the presence of stated features, integers, steps or components but does not preclude the presence or addition of one or more other features, integers, steps, components or groups thereof.

The invention claimed is:

1. A method performed by a particle detection system, said method being configured to synchronise between a light source of the particle detection system and an image capturing means of the particle detection system, the method comprising:
   allowing the light source to oscillate on and off at a predetermined rate;
   identifying the light source in video images captured by the image capturing means and;
   continually modifying the image capturing means frame rate to remain in synchronisation with the oscillation of the light source.

2. A method as claimed in claim 1 wherein the light source is fitted with a secondary light source having a wide angle of emission wherein the step of identifying the light source comprises identifying the secondary light source.

3. A method as claimed in claim 2 further comprising the step of: flashing the secondary light source in a predetermined timing relationship with the light source to facilitate locating the light source in the image capturing means image.

4. A method as claimed in claim 2, wherein the secondary light source is a LED.

5. A method as claimed in claim 4 wherein the secondary light source flashes in one or more of: a periodic pattern; a pseudorandom sequence.

6. A method as claimed in claim 2, wherein the secondary light source operates in synchronisation with the light source.

7. A method as claimed in claim 1 wherein the image capturing means has an initial frame rate that approximates the rate of an oscillator of the light source, and the method further comprises;
   identifying flashing of the light source; varying the phase of the image capturing means frame rate to maintain a timing relationship between image capturing means exposures and the light source.

8. A method as claimed in claim 7 wherein which includes determining a rate of change of phase between an oscillator of the light source and an oscillator of the image capture means.

9. A method as claimed in claim 8 which includes using a phase locked loop feedback mechanism to adjust a frame rate of the image capturing means to maintain a fixed phase with the light source to remain in synchronisation therewith.

10. A method as claimed in claim 1 wherein a frequency of the light source oscillator is altered to be one of: the same as; a multiple of; a sub multiple of an AC mains electricity supply frequency.

11. A method as claimed in claim 10 which includes:
    sensing the mains electricity supply frequency directly from the mains supply.

12. A method as claimed in claim 10 wherein the step of sensing the mains electricity supply frequency directly from the mains supply comprises:
    sensing the mains electricity supply frequency using an inductive or capacitive coupling.

13. A method as claimed in claim 10 which includes:
    sensing the mains electricity supply frequency using a photoelectric detector arranged to receive light from artificial lighting.

14. A method as claimed in claim 2 which includes:
    providing the light source with a battery backed power supply; and wherein the method further includes;
    dropping the light source duty cycle when operating on backup power to indicate that backup power is being used.

15. A method as claimed in claim 2 wherein status information is transmitted via modulation of the light source or secondary light source.

16. Apparatus adapted to detect particles in a region, said apparatus comprising:
    a light source arranged to emit a beam of light across the region said beam of light oscillating on and off at a predetermined rate,
    image capturing system configured to generate video images of the region;
    a processor configured to:
    identify the light source in one or more video images and to modify the image capturing system's frame rate to remain in synchronisation with the oscillation of the beam of light; and
    detect a variation in the video images to indicate the presence of particles in the region.

17. An apparatus as claimed in claim 16 wherein the light source is fitted with a secondary light source comprising a wide angle of emission.

18. An apparatus as claimed in claim 17, wherein the secondary light source is a LED.

19. A method as claimed in claim 6, wherein he image capturing means has an initial frame rate that approximates the rate of the oscillator of the light source, wherein the method further comprises;
    identifying flashing of the secondary light source;
    varying a phase of the image capturing means frame rate to maintain a timing relationship between image capturing means exposures and the light source.

* * * * *